United States Patent [19]

Kaneko

[11] Patent Number: 4,741,980

[45] Date of Patent: May 3, 1988

[54] METHOD FOR INCREASING COLOR-FASTNESS OF ORGANIC COLORING MATTER

[75] Inventor: Yutaka Kaneko, Sagamihara, Japan

[73] Assignee: Konishiroku Photo Industry Co., Ltd., Tokyo, Japan

[21] Appl. No.: 908,603

[22] Filed: Sep. 18, 1986

[30] Foreign Application Priority Data

Sep. 19, 1985 [JP] Japan .................... 60-207362

[51] Int. Cl.$^4$ .................... G03C 1/84; G03C 1/08
[52] U.S. Cl. .................... 430/17; 430/512; 430/551; 430/931; 430/216; 430/220; 252/400.53
[58] Field of Search ................ 430/17, 512, 551, 931, 430/216, 220; 252/400.53

[56] References Cited

U.S. PATENT DOCUMENTS

| | | | |
|---|---|---|---|
| 2,360,290 | 7/1941 | Vittum | 95/6 |
| 2,418,613 | 7/1945 | Allen | 95/7 |
| 2,675,314 | 4/1951 | Vittum | 95/6 |
| 2,701,197 | 1/1955 | Thirtle et al. | 95/7 |
| 3,069,262 | 12/1962 | Haas | 96/29 |
| 3,215,717 | 11/1965 | Foster | 524/176 |
| 3,432,300 | 3/1969 | Lestina et al. | 430/505 |
| 3,457,079 | 7/1969 | Koda et al. | 430/607 |
| 3,573,050 | 3/1971 | Branrock | 96/84 |
| 3,574,626 | 4/1971 | Kunitz et al. | 430/554 |
| 3,574,627 | 4/1971 | Stern et al. | 96/100 |
| 3,698,909 | 10/1972 | Lestina et al. | 430/551 |
| 3,764,337 | 10/1973 | Arai et al. | 430/551 |
| 3,932,324 | 1/1976 | Stretanski | 252/400.53 |
| 4,015,990 | 4/1977 | Ishida et al. | 96/84 |
| 4,540,653 | 9/1985 | Nishijima et al. | 430/551 |

FOREIGN PATENT DOCUMENTS

| | | |
|---|---|---|
| 0187521 | 7/1986 | European Pat. Off. ......... 430/551 |
| 13496 | 6/1968 | Japan . |
| 99340 | 8/1981 | Japan . |
| 168652 | 12/1981 | Japan . |
| 51834 | 4/1985 | Japan . |

Primary Examiner—Paul R. Michl
Assistant Examiner—Patrick Doody
Attorney, Agent, or Firm—Finnegan, Henderson, Farabow, Garrett & Dunner

[57] ABSTRACT

A method for increasing color-fastness of organic coloring matters against light is disclosed. The color-fastness of the organic coloring matter of which absorption maximum is the region from 400 nm to 700 nm is increased by coexisting with a metal complex represented by the following general formula:

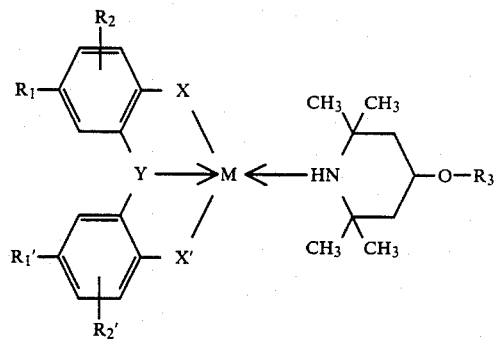

in which $R_1$, $R_2$, $R_1'$ and $R_2'$ are a hydrogen atom or a substituent, X and X' are O or S, Y is O, S, SO or SO$_2$ and M is a metal atom.

The method adapts to improve the fastness of color images of silver halide photographic materials. In this case, the organic coloring matter is a dyestuff formed by coupling a color forming coupler with an oxidation product of a color developing agent in the silver halide color photographic material or a dyestuff diffused to a receiving layer of the diffusion transfer silver halide color photographic material.

10 Claims, No Drawings

METHOD FOR INCREASING COLOR-FASTNESS OF ORGANIC COLORING MATTER

FIELD OF THE INVENTION

The present invention relates to a method for increasing the color-fastness of organic coloring matters against light and more particularly to a method of increasing the color-fastness of colored images against light in the area of photography.

BACKGROUND OF THE INVENTION

It is a widely known fact that compounds of organic coloring matters, such as the coloring matters for forming colored images in the field of photography, the organic dyes for dyeing fibers, and the coloring matters used in the area of printing, are liable to color-fading or discoloration by the effect of light. In view of this situation, various methods have been proposed for improving the color-fastness of such coloring matters against light.

One of such methods consists in a process characterized by the use of a certain kind of compound which improves the color-fastness of such a dye against light. For example, as the compounds which improve the fastness of colored images against light can be pointed out the hydroquinone derivatives mentioned in U.S. Pat. No. 2,360,290, No. 2,418,613, No. 2,675,314, No. 2,701,197, and so forth, the derivatives, such as chroman and chraman, which are mentioned in U.S. Pat. No. 3,432,300, No. 3,573,050, No. 3,574,627, No. 3,764,337, No. 3,574,626, No. 3,698,909, and No. 4,015,990, and the p-alkoxyphenols which are mentioned in U.S. Pat. No. 3,457,079 and No. 3,069,262, Japanese Patent Examined Publication No. 13496/1968, and so on.

Those compounds, however, were not necessarily satisfactory in terms of their effect. In the meanwhile, a technique for improving color-fastness against light by the use of a metallic complex is described in Japanese Patent Pulbication Open to Public Inspection Nos. 99340/1981, 168652/1981 and 51834/1985. (hereinafter referred to as Japanese Patent O.P.I. Publication). Among these metallic complexes, however, some had to be used in large quantities because their light-resisting effect was small. Some other such complexes were effective as a color-fastness improving agent working against light, and yet some of those had the shortcoming that the coloration of the metallic complexes themselves was so intense that they produce an effect of yellowish, yellowgreenish, or greenish coloring.

Above all, in case any such agent is used for photosensitive material for photography, any coloring of white areas will give considerable damages to aesthetic features, and such coloration will be a cause of a deterioration of the merchandise value.

Moreover, among such metallic complexes, there are some which causes an increase of fogging or staining by the effect of heat if such a complex is used for any silver halide photosensitive material for photography.

While conducting experiments up to the present time with respect to the metallic complexes hitherto known as such, we found that many of them were effective as color-fastness improving agents, but, as the coloration of such a metallic complex itself and an increase of fogging gave rise to a decrease of lightness, a change in hue, or a deterioration of the white-color areas in consequence of the occurrence of stain by the effect of heat, none of those complexes could be used with any satisfactory result unless some measure was taken for the settlement of the problem.

In view of these circumstances, we have been in continuous pursuit of a metallic complex which has a great color-fastness effect for organic coloring matter compounds, does not give any adverse effect to pictures, even if the complex is used as a color-fastness improving agent for colored images, because of the slightness of coloration in the metallic complex itself, or does not give any unfavorable influence resulting from an increase of fogging or the occurrence of stain even in case the complex is used for any silver halide photosensitive material for photography.

SUMMARY OF THE INVENTION

The primary object of the present invention is to provide an excellent method for improving the color-fastness to light of organic coloring matter compounds.

The second object of the present invention is to provide an excellent method for improving the color-fastness to light of colored images which does not give any adverse influence to such images because of the coloration of the metallic complex itself.

The third object of the present invention is to provide an excellent method for improving the color-fastness to light of colored images which does not give any adverse influence to colored images because of the coloration of the metallic complex itself or give rise to any increase of fogging or any occurrence of stain by the effect of heat, either, even when the metallic complex is applied to any silver halide photosensitive material for photography.

The above-mentioned objects have been accomplished by a method for increasing fastness of an organic coloring matter, which making coexist the organic coloring matter having the absorption maximum within the wavelength region from 400 nm to 700 nm together with a compound represented by the following general formula in a medium:

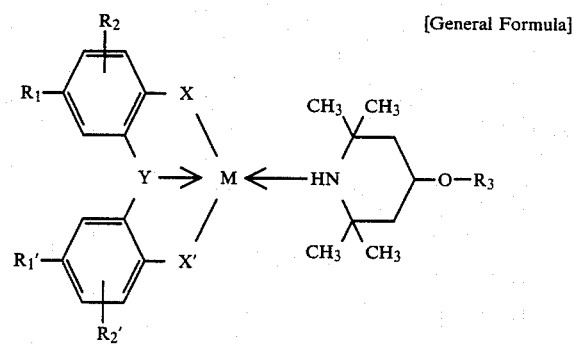

[General Formula]

wherein $R_1$ and $R_1'$ are independently selected from a hydrogen atom, an alkyl group, a cycloalkyl group, a halogen atom, an alkoxy group, an aryloxy group, —CO—O—$R_4$,

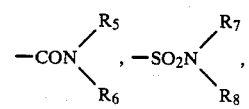

—NHCOR$_9$ and —NHSO$_2$R$_{13}$, $R_4$ is selected from an alkyl group and a cycloalkyl group, $R_5$ and $R_6$ are independently selected from a hydrogen atom, an alkyl group, an aryl group and a cycloalkyl group, and $R_5$ and $R_6$ may be bonded to form a five to seven membered ring, $R_7$ and $R_8$ are the same as $R_5$ and $R_6$, $R_9$ is selected from an alkyl group, an aryl group —$OR_{10}$ and

$R_{10}$ is selected from an alkyl group and a cycloalkyl group, $R_{11}$ and $R_{12}$ are the same as $R_5$ and $R_6$, $R_{13}$ is selected from an alkyl group, an aryl group and

$R_{14}$ and $R_{15}$ are the same as $R_5$ and $R_6$.

$R_2$ and $R_2'$ are independently selected from a hydrogen atom, a halogen atom, an alkyl group, an alkoxy group, an alkoxycarbonyl group, an alkenyl group and a cycloalkyl group, and $R_1$ and $R_2$, or $R_1'$ and $R_2'$ may be bonded to form a condensed benzene ring, respectively, M is a metal atom, X and X' is independently selected from an oxygen atom and a sulfur atom, Y is selected from an oxygen atom, a sulfur atom, —SO and —SO$_2$, and $R_3$ is selected from a hydrogen atom, an alkyl group, an aryl group, a cycloalkyl group, —CO—$R_{16}$,

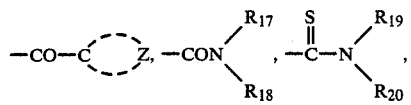

—SO—$R_{21}$ and —SO$_2R_{22}$, $R_{16}$ is selected from an alkyl group, an alkenyl group, an aryl group and a cycloalkyl group, Z is a group of atoms necessary to complete five or six membered heterocyclic ring, $R_{17}$ and $R_{18}$ are independently selected from a hydrogen atom, an alkyl group, an aryl group and a cycloalkyl group, $R_{17}$ and $R_{18}$ may be bonded to form a five to seven membered ring, $R_{19}$ and $R_{20}$ are the same as $R_{17}$ and $R_{18}$, $R_{21}$ is selected from an alkyl group and an aryl group and $R_{22}$ is the same as $R_{21}$.

The compounds expressed by the general formula given above are called "metallic complexes relevant to the present invention" in the subsequent part of the present specification.

DETAILED DESCRIPTION OF THE INVENTION

A description is given hereinbelow of the metallic complexes relevant to the present invention.

In the general formula, $R_1$ and $R_1'$ respectively expresses a hydrogen atom, an alkyl group (including such a group which contains a substituent—for example, a methyl group, a butyl group, a t-octyl group, an n-dodecyl group, a phenethyl group, a cumyl group, an octylcarbonyloxyethyl group, and a 2-ethoxyhexyl group), a cycloalkyl group (including such a group which contains a substituent—for example, a cyclohexyl group), a cycloalkyl group (including such a group which contains a substituent—for example, a cyclohexyl group), a halogen atom (for example, a chlorine atom), an alkoxy group (including such a group which contains a substituent—for example, a butoxy group, an octoxy group, and a benziloxy group), an allyloxy group (including such a group which contains a substituent—for example, a phenoxy group, a naphtoxy group, and 2,4-di-t-butylphenoxy group), —CO—O—$R_4$ (including such a group which contains a substituent—for example, a butoxycarbonyl, group, a pentyloxycarbonyl group, and a cyclohexyloxycarbonyl group), and

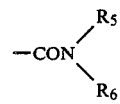

(including such a group which contains a substituent—for example, a carbamoyl group, dibutylcarbamoyl group, a diphenylcarbamoyl group, and an N-butyl-N-phenylcarbamoyl group). Moveover, $R_5$ and $R_6$ may form a bond with each other to make a five- to seven-membered ring—for example, pyridyl),

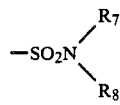

(including such a group which contains a substituent. As examples, a sulfamoyl group, a dimethylsulfamoyl group, and an N-butyl-N-phenylsufamoyl group can be listed. Furthermore, $R_7$ and $R_8$ may form a bond with each other to make a five- to seven-membered ring—for example, pyridyl), —NHCOR$_9$ (including such a group which contains a substituent—for example, a butanecarbonamido group, a benzenecarbonamino group, a p-methylphenylcarbonylamino group, an octyloxycarbonylamino group, a cyclohexyloxycarbonylamino group, a carbamide group, and N,N-dimethylcarbamide group), or —NHSO$_2R_{13}$ (including such a group which contains a substituent—for example, a butanesulfonamido group, a benzenesulfonamido group, a dibutylaminosulfonylamino group, a diphenylaminosulfonylamino group, and a ditolylaminosulfonylamino group). Of $R_1$ and $R_1'$, the more preferable group is an alkyl group.

In the general formula, $R_2$ and $R_2'$ respectively express a hydrogen atom, a halogen atom (for example, a chlorine atom), an alkyl group (including such a group which contains a substituent—for example, a methyl group, an ethyl group, an octyl group, a dodecyl group, and a cumyl group), an alkoxy group (including such a group which contains a substituent—for example, a butoxy group, and an octyloxy group), alkoxycarbonyl group (including such a group which contains a substituent—for example, a pentyloxycarbonyl group), an alkenyl group (including such a group which contains a propenyl group), or a cycloalkyl group (including such a group which contains a substituent—for example, a cyclohexyl group).

The preferable group in $R_2$ and $R_2'$ is a hydrogen atom or an alkyl group.

Moreover, $R_1$ and $R_2$ and/or $R_1'$ and $R_2'$ may form a condensed benzene ring through their formation of a bond with each other.

In the general formula, $R_3$ expresses a hydrogen atom, an alkyl group (including such a group which contains a substituent—for example, a methyl group, an ethyl group, an octyl group, a dodecyl group, and a phenetyl group), an aryl group (including such a group which contains a substituent—for example, a phenyl group, a 2,4-di-t-butylphenyl group), a cycloalkyl group (including such a group which contains a substituent—for example, a cyclohexyl group), —CO—$R_{16}$ (including such a group which contains a substituent—for example, an ethylcarbonyl group, a phenylcarbonyl group, a cyclohexylcarbonyl group, and a p-methylphenylcarbonyl group),

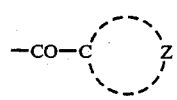

(including such a group which contains a substituent, Z expresses a group of atoms which form a five- to six-membered ring containing hetero-atoms—for example, pyridyl and furyl),

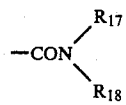

(including such a group which contains a substituent—as examples, a carbamoyl group, a dibutylcarbamoyl group, a diphenylcarbamoyl group, and an N-butyl-N-phenylcarbamoyl group can be listed. Also, $R_{17}$ and $R_{18}$ may make a bond with each other to form a five- to seven-membered ring—for example, pyridyl),

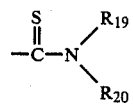

(including such a group which contains a substituent—as examples, an aminothiocarbonyl group, dibutylaminothiocarbonyl group, a dephenylaminothiocarbonyl group, an N-butyl-N-phenylaminothiocarbonyl, and so forth can be cited. Moreover, $R_{19}$ and $R_{20}$ may make a bond with each other to form a five- to seven-membered ring—for example, pyridyl), —SO—$R_{21}$ (including such a group which contains a substituent—for example, an ethylsulfinyl group, a butylsulfinyl group, a phenylsulfinyl group, and a p-methylphenylsulfinyl group), or —SO$_2$R$_{22}$ (including such a radical which contains a substituent—for example, an ethylsulfonyl group, a butylsulfonyl group, a phenylsulfonyl group, and a p-methylphenylsulfonyl group).

The preferable group in $R_3$ is —CO—$R_{16}$. Here, it is preferable that the sum total of the numbers of carbons in $R_1$, $R'_1$, $R_2$, $R'_2$ and $R_3$ is 10 or more but 50 or less.

M expresses a metal atom, and, more preferably, a transition metal atom. Of such transition metal atoms, the more preferable ones are the atoms of Fe, Ni, Co, Pd, Pt, and Cu, and the most preferable one is the atom of Ni.

X and X' respectively express an oxygen atom or a sulfur atom, but, more preferably, it is an oxygen atom. Y expresses a sulfur atom, an oxygen atom, SO or SO$_2$, but, more preferably, it is a sulfur atom.

The metal complex relevant to the present invention is preferably a compound which is represented by the general formula given below.

General formula

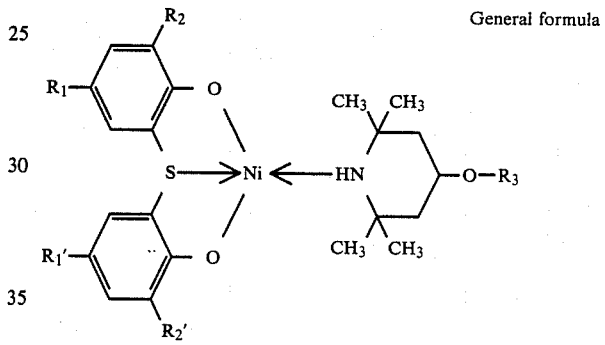

In this general formula, $R_1$, $R'_1$, $R_2$, $R'_2$, and $R_3$ are synonymous with those expressed by the afore-mentioned general formula. In the general formula given above, a preferable case is one in which the sum total of the numbers of carbons in $R_1$, $R'_1$, $R_2$, and $R'_2$ is 16 or more, $R_1$ and $R'_1$ being alkyl groups and $R_2$ and $R'_2$ being hydrogen atoms or alkyl groups. Moreover, it is preferable that $R_3$ is —CO—$R_{16}$ and that $R_{16}$ is an alkyl group.

In the following are given concrete examples of metal complexes relevant to the present invention, but this invention is not limited to these.

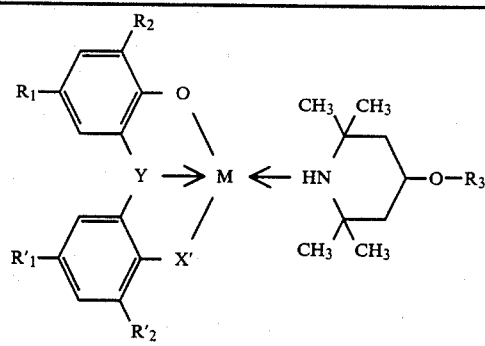

| No. | $R_1$ | $R'_1$ | $R_2$ | $R'_2$ | X | X' | Y | M | $R_3$ |
|-----|-------|--------|-------|--------|---|----|----|----|-------|
| 1 | —$C_8H_{17}$(t) | —$C_8H_{17}$(t) | H | H | O | O | S | Ni | —CO—$C_{17}H_{35}$ |
| 2 | —$C_8H_{17}$(t) | —$C_8H_{17}$(t) | H | H | O | O | S | Ni | —CO—$C_2H_5$ |

-continued

| # | | | | | | | | | |
|---|---|---|---|---|---|---|---|---|---|
| 3 | $-C_8H_{17}(t)$ | $-C_8H_{17}(t)$ | H | H | O | O | S | Ni |  $-CO-\phantom{x}-CH_3$ |
| 4 | $-C_8H_{17}(t)$ | $-C_8H_{17}(t)$ | H | H | O | O | SO | Ni | $-CO-C_{11}H_{23}$ |
| 5 | $-C_8H_{17}(t)$ | $-C_8H_{17}(t)$ | H | H | O | O | S | Ni | $-CO-C_{11}H_{23}$ |
| 6 | $-C_8H_{17}(t)$ | $-C_8H_{17}(t)$ | H | H | O | O | S | Ni |  $-CO-\phantom{x}$ |
| 7 | $-C_8H_{17}(t)$ | $-C_8H_{17}(t)$ | H | H | O | O | S | Ni | 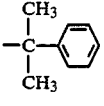 $-CO-$ naphthyl |
| 8 | $-C_8H_{17}(t)$ | $-C_8H_{17}(t)$ | H | H | O | O | $SO_2$ | Ni | $-CO-C_{11}H_{23}$ |
| 9 | $-C_8H_{17}(t)$ | $-C_8H_{17}(t)$ | H | H | O | O | O | Ni | $-CO-C_{11}H_{23}$ |
| 10 | $-C_8H_{17}(t)$ | $-C_8H_{17}(t)$ | H | H | S | S | S | Ni | $-CO-C_{11}H_{23}$ |
| 11 | $-C_8H_{17}(t)$ | $-C_8H_{17}(t)$ | H | H | S | S | O | Ni | $-CO-C_{11}H_{23}$ |
| 12 | $-C_8H_{17}(t)$ | $-C_8H_{17}(t)$ | Cl | Cl | O | O | S | Ni | $-CO-C_{11}H_{23}$ |
| 13 | cyclohexyl | cyclohexyl | Cl | Cl | O | O | SO | Ni | $-CO-C_{11}H_{23}$ |
| 14 | $-C_5H_{11}(t)$ | $-C_5H_{11}(t)$ | $-C_5H_{11}(t)$ | $-C_5H_{11}(t)$ | O | O | S | Ni | $-CO-C_{11}H_{23}$ |
| 15 | $-C_8H_{17}(t)$ | $-C_8H_{17}(t)$ | $-C_8H_{17}(t)$ | $-C_8H_{17}(t)$ | O | O | S | Ni | $-CO-C_{11}H_{23}$ |
| 16 | $-C_8H_{17}(t)$ | $-C_8H_{17}(t)$ | H | H | O | O | S | Cu | $-CO-C_{17}H_{35}$ |
| 17 | $-C_8H_{17}(t)$ | $-C_8H_{17}(t)$ | H | H | O | O | S | Pd | $-CO-C_{17}H_{35}$ |
| 18 | $-C_8H_{17}(t)$ | $-C_8H_{17}(t)$ | H | H | O | O | S | Pt | $-CO-C_{17}H_{35}$ |
| 19 | $-C_8H_{17}(t)$ | $-C_8H_{17}(t)$ | H | H | O | O | S | Ni | $-C_8H_{17}$ |
| 20 | $-C_5H_{11}(t)$ | $-C_5H_{11}(t)$ | $-C_5H_{11}(t)$ | $-C_5H_{11}(t)$ | O | O | S | Ni | $-C_8H_{17}$ |
| 21 | $-C_5H_{11}(t)$ | $-C_5H_{11}(t)$ | $-C_5H_{11}(t)$ | $-C_5H_{11}(t)$ | O | O | S | Ni | 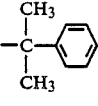 $-CO-\phantom{x}$ |
| 22 | $-C_5H_{11}(t)$ | $-C_5H_{11}(t)$ | $-C_5H_{11}(t)$ | $-C_5H_{11}(t)$ | O | O | S | Ni | 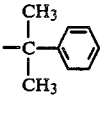 $-CO-\phantom{x}-CH_3$ |
| 23 | $-C_5H_{11}(t)$ | $-C_5H_{11}(t)$ | $-C_5H_{11}(t)$ | $-C_5H_{11}(t)$ | O | O | S | Ni | $-CO-CH_3$ |
| 24 | $-C_5H_{11}(t)$ | $-C_5H_{11}(t)$ | $-C_5H_{11}(t)$ | $-C_5H_{11}(t)$ | O | O | S | Ni | $-CO-CH=CH_2$ |
| 25 | $-C_5H_{11}(t)$ | $-C_5H_{11}(t)$ | $-C_5H_{11}(t)$ | $-C_5H_{11}(t)$ | O | O | S | Ni | H |
| 26 | $-O(CH_2)_3CH_3$ | $-O(CH_2)_3CH_3$ | H | H | O | O | S | Ni | $-CO-C_{11}H_{23}$ |
| 27 | $-OC_4H_9$ | $-OC_4H_9$ | $-CH_2-C(CH_3)=CH_2$ | $-CH_2-C(CH_3)=CH_2$ | O | O | S | Ni | $-CO-C_{11}H_{23}$ |
| 28 | $-CO-N(C_4H_9)_2$ | $-CO-N(C_4H_9)_2$ | H | H | O | O | S | Ni | $-CO-C_{17}H_{35}$ |
| 29 | $-C_4H_9(t)$ | $-C_4H_9(t)$ | $-COO-C_2H_4-CH(CH_3)_2$ | $-COO-C_2H_4-CH(CH_3)_2$ | O | O | SO | Ni | $-CO-C_{17}H_{35}$ |
| 30 | $-C(CH_3)_2-C_6H_5$ | $-C(CH_3)_2-C_6H_5$ | H | H | O | O | S | Ni | H |
| 31 | $-C(CH_3)_2-C_6H_5$ | $-C(CH_3)_2-C_6H_5$ | H | H | O | O | S | Ni | $-CO-C_{17}H_{35}$ |
| 32 | $-CH_3$ | $-CH_3$ | $-C_4H_9(t)$ | $-C_4H_9(t)$ | O | O | S | Ni | H |
| 33 | $CH_3$ | $CH_3$ | $-C_4H_9(t)$ | $C_4H_9(t)$ | O | O | S | Ni | $-CO-CH_3$ |
| 34 | $-CH_3$ | $-CH_3$ | $-C_4H_9(t)$ | $-C_4H_9(t)$ | O | O | S | Ni | $-C_2H_5$ |

NO. 35

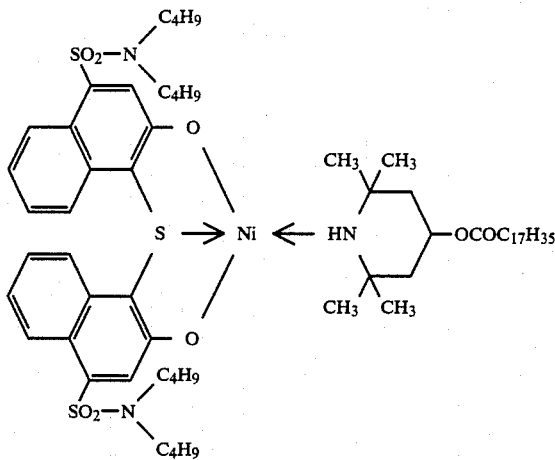

NO. 36

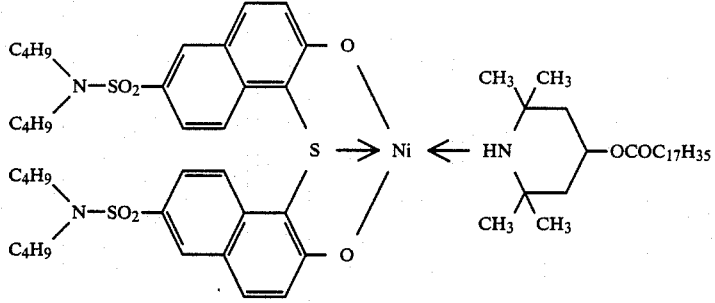

NO. 37

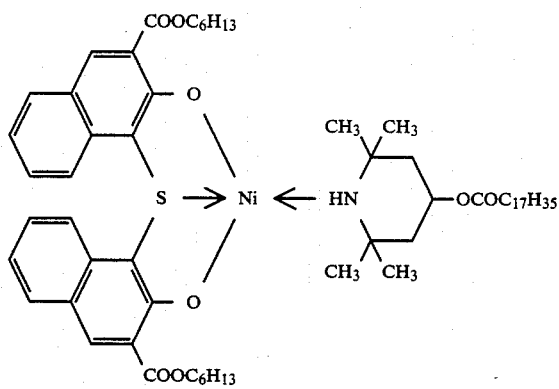

The organic coloring matter compounds of the present invention with the maximum absorption in the wave length region ranging at least from 400 nm to 700 nm include each and all, for example, of azo dye, diphenylmethane dye, triphenylmethane dye, hormazane dye, indophenol dye, indoamine dye, indigoid dye, an oxazine dye, thiazine dye, cyanine dye, azometine dye, or any dye that is used in the field of photography (for example, a dye formed by the reaction between a coupler and an oxidized product of a color developing agent, and a dye donated by a dye donating substance used for instant photography).

Here, the maximum absorption by an organic coloring matter compound is what is observed in the mode in which the particular organic coloring matter compound is used.

The metallic complex relevant to the present invention will be used in its coexistence with an organic coloring matter compound, but the amount of such a complex used will be different, depending on the kind of the metallic complex relevant to the present invention and the kind of organic coloring matter compound which are used in any given instance, and it is not possible to make any sweeping statement. However, such a complex is to be generally used in the ratio of 0.01 to 1 mol for one mol of an organic coloring matter compound and is preferably used in the ratio of 0.05 to 0.5 mol.

As regards the method of having a metallic complex relevant to the present invention coexist with an organic coloring matter compound, there is, for example, a method consisting in impregnating in advance a metallic complex relevant to the present invention into the fiber to be dyed with an organic dye.

The metallic complex relevant to the present invention works to improve the fastness of an organic coloring matter compound against light, and, for example, in a case in which a colored image is formed with an organic coloring matter compound, it is possible to improve the fastness of the colored image against light by having a metallic complex relevant to the present invention exist in the inside of the layer in which the colored image is sustained. As regards the concrete modes in which the colored image is formed, such instances as the case in which a colored image is formed by the reaction between the coupler and an oxidized product of the color developing agent, for example, in a silver halide color photosensitive material having a silver halide emulsion layer provided on a support which contains a coupler to be described later, or the case in which the dye donated from a dye donating substance present in the photosensitive layer of a diffusion transfer photosensitive material is diffused and transferred to an image-receiving layer provided in a unified structure with or separately from the photosensitive layer, and the colored image held on the image-receiving layer being ultimately formed in the image-receiving layer, in the diffusion transfer type photosensitive material used for instant photography can be cited.

The coloring matter donating substances which can be used for the diffusion transfer type photosensitive material are described, for example, in U.S. Pat. No. 2,983,606, No. 3,345,163, No. 3,265,001, No. 3,218,164, No. 3,453,107, No. 3,651,406, No. 3,135,605, No. 3,421,892, No. 3,563,789, No. 3,482,972, No. 3,415,644, No. 3,594,165, No. 3,227,550, No. 3,880,658, No. 3,765,686, British Pat. No. 840,731, No. 904,364, No. 904,365, No. 1,033,331, Japanese Patent Examined Publication No. 15471/1970, Japanese Patent Application No. 133879/1975, No. 318480/1975, U.S. Pat. No. 3,725,052, No. 3,698,897, No. 3,728,113, No. 3,828,817, No. 3,844,785, No. 3,942,987, No. 3,932,380, No. 3,932,381, No. 3,937,144, No. 3,929,760, No. 3,245,709, French Pat. No. 2,284,140, Japanese Patent O.P.I. Publication No. 118723/1975, No. 104343/1976, No. 7727/1977, No. 8827/1977, No. 113624/1976, No. 116528/1975, No. 114930/1976, Japanese Patent Application No. 78057/1976, No. 125867/1976, No. 78423/1976, No. 78777/1976, No. 125860/1976, and so forth.

In the diffusion transfer type photosensitive material mentioned above, the color-fastness to light of a colored image formed in the image-receiving layer is improved by having a metallic complex relevant to the present invention contained in the image receiving layer. In this case, the amount used of the metallic complex relevant to the present invention is 0.1 mg/cm$^2$~10 mg/cm$^2$ in the image-receiving layer.

For the methods of having the metallic complex relevant to the present invention contained in the image-receiving layer, various methods, such as an alkali aqueous solution dispersion method, a solid dispersion method, a latex dispersion method, and an oil-drop-in-water type emulsion dispersion method, can be employed.

Furthermore, the color-fastness to light of a colored image formed by the reaction between a coupler and an oxidized product of the color-developing agent can be improved by having the metallic complex relevant to the present invention contained in the silver halide photosensitive material for photography which comprises a support and, provided thereon, a silver halide emulsion layer containing a coupler as mentioned above.

In case the metallic complex relevant to the present invention is caused to be contained in silver halide photosensitive material for photography, a coupler-containing layer is preferable, and, in particular, a magenta-coupler-containing layer is preferable.

The metallic complex relevant to the present invention is to be used preferably in the ratio of 0.01~1 mol for one mol of the coupler, and, more preferably, it is to be used in the ratio of 0.05~0.5 mol.

As for the methods of adding the metallic complex relevant to the present invention to the silver halide photosensitive material for photography, the complex can be dispersed by using various methods, such as a solid dispersion method, a latex dispersion method, and an oil-drop-in-water type dispersion method, can be employed in the same way as the methods of adding hydrophobic compounds, and such a method can be selected as appropriate for the chemical structure, etc. of the metallic complex relevant to the present invention. The oil-drop-in-water type emulsion dispersion method enables it to apply a method of dispersing a hydrophobic compound of a coupler or the like, and, ordinarily, the complex can be added to the hydrophilic colloid layer which is taken as the object, after the complex is dissolved into a high-boiling-point organic solvent the boiling point of which is approximately 150° C. or higher, with a low-boiling-point solvent and/or a water-soluble organic solvent being used together as necessary, the complex being emulsified in a hydrophilic binder, such as an aqueous solution of gelatin by using a surface active agent and by such a dispersing means as an agitator, a homogenizer, a colloid mill, a flowsit mixer, or an ultrasonic equipment. It is feasible also to include a work process for removing the low-boiling-point organic solvent after or at the same time as dispersion.

For the high-boiling-point solvent are used any such organic solvents as a phenol derivative, phethalate, phosphate, citrate, benzoate, alkyl amide, fatty acid ester, and trimeciate, which have a boiling point not lower than 150° C.

The high-boiling-point organic solvents which can be preferably used in the present invention are such compounds with a dielectric constant of 6.0 or less, which, for example, are such ester varieties as phthatates and phosphate, organic acid amides, ketones, and hydrocarbon compounds. Preferably, such solvents are high-boiling-point organic solvents with a dielectric constant not more than 6.0 but not less than 1.9 and with a vapor pressure of 0.5 mmHg or less. Also, more preferably, such solvents are phthalate or phosphate among the high-boiling-point organic solvents. Furthermore, the high-boiling-point organic solvent may be a mixture of two or more kinds of such solvents.

Moreover, the term, "dielectric constant", as used in the present invention indicates the dielectric constant at 30° C.

As the phthalates which can be used advantageously in the present invention, the compound which is expressed by the general formula [a] given in the following can be mentioned.

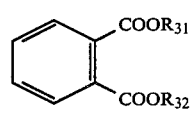

General formula [a]

In this formula, $R_{31}$ and $R_{32}$ respectively express an alkyl group, an alkenyl group, or an aryl group. However, the sum total of the carbon atoms of the group expressed by $R_{31}$ and $R_{32}$ is 8 to 32. Also, more preferably, the sum total of the carbon atoms is 16 to 24.

In the present invention, the alkyl group which is expressed by $R_{31}$ and $R_{32}$ in the general formula [a] given above may be such a group with either a normal chain or branched chain, and, for example, it is a butyl group, a pentyl group, a hexyl group, a heptyl group, an octyl group, a nonyl group, a decyl group, an undecyl group, a dedecyl group, a tridecyl group, a teltradecyl group, a pentadecyl group, a hexadecyl group, a heptadecyl group, an octadecyl group, and so forth. The aryl group which is expressed by $R_{31}$ and $R_{32}$ is, for example, a phenyl group, a naphthyl group, and so on, and the alkenyl group is, for example, a hexenyl group, a heptenyl group, an octadecenyl group, etc. These alkyl groups, alkenyl groups, and anyl groups may have a single or plural number of substituents, and, as the substituents for the alkyl group or the alkenyl group, a halogen atom, an alkoxy group, an aryl group, an aryloxy group, an alkenyl group, an alkoxycarbonyl group, and so on, for example, can be cited, and, as the substituents for the aryl group, a halogen atom, an alkyl group, an alkoxy group, an aryl group, an aryloxy group, an alkenyl group, an alkoxycarbonyl group, and so on, for example, can be mentioned.

As the phosphates which can be used advantageously in the present invention, the compound expressed by the general formula [b] mentioned in the following can be cited:

$$R_{35}O-\overset{\overset{O}{\|}}{\underset{OR_{34}}{P}}-OR_{33}$$ General formula [b]

In this formula, $R_{33}$, $R_{34}$, and $R_{35}$ respectively express an alkyl group, an alkenyl group, or an aryl group. However, the sum total of the carbon atoms expressed by $R_{33}$, $R_{34}$, and $R_{35}$ is 24 to 54.

The alkyl groups which are expressed by $R_{33}$, $R_{34}$, and $R_{35}$ in the general formula [b] are, for example, a butyl group, a pentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, and so forth, and an aryl group is, for example, a phenyl group, a naphthyl group, etc., and an alkenyl group is, for example, a hexenyl group, a heptenyl group, and octadecenyl group, and so forth.

These alkyl group, alkenyl group, and aryl group may have a single or plural number of substituents. Preferably, $R_{33}$, $R_{34}$, and $R_{35}$ are an alkyl group. For example, a 2-ethylhexyl group, an n-octyl group, a 3,5,5-trimethylhexyl group, an n-nonyl group, an n-decyl group, a sec-decyl group, a sec-dodecyl group, a t-octyl group, and so on can be cited.

In the following part, representative examples of embodiments of the organic solvents used for the present invention are given, but they shall not be limited to these.

Examples of Organic Solvent

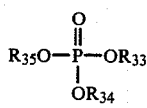

S-1

-continued
Examples of Organic Solvent

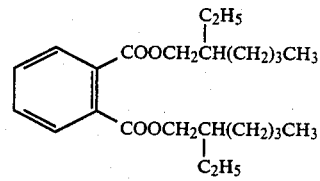

S-2

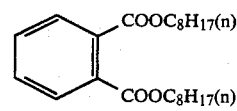

S-3

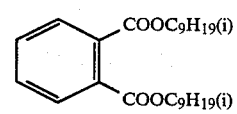

S-4

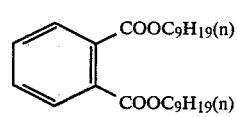

S-5

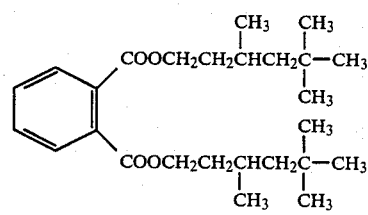

S-6

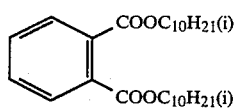

S-7

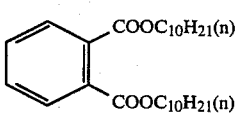

S-8

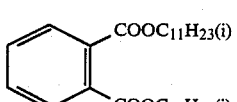

S-9

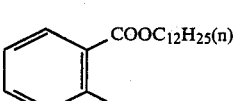

S-10

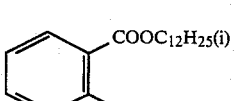

S-11

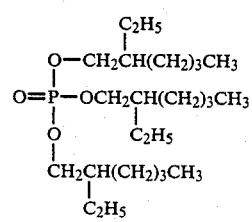

S-12

-continued
Examples of Organic Solvent

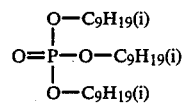
S-13

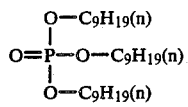
S-14

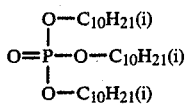
S-15

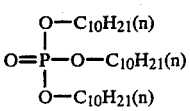
S-16

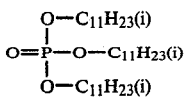
S-17

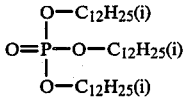
S-18

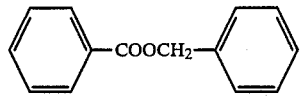
S-19

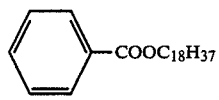
S-20

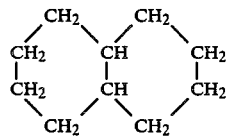
S-21

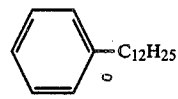
S-22

Next, an explanation is given with respect to the coupler to be used for the silver halide photosensitive material for photography.

For couplers, yellow, magenta, and cyan couplers are ordinarily used.

For the magenta coupler, such couplers as those of the 5-pyrazolone type, the cyanoacetophenone type, the indazolone type, the pyrazolinobenzimidazole type, and the pyrazolotriazole type are employed.

For magenta coupler which is to be preferably used in the present invention is the magenta coupler expressed by the general formula [I] or the general formula [XIV] given below and, specially preferably, is the magenta coupler expressed by the general formula [I].

General formula [I]

General formula [I]

[In this formula, $Z_1$ expresses a non-metal atom group which is necessary for the formation of a nitrogen-containing heterocyclic ring, and the ring which is formed with the $Z_1$ may have a substituent.

$X_2$ expresses a hydrogen atom or a group which is, upon reaction with an oxidation product of a color developing agent, capable of being released from the coupler residue. $R_{41}$ expresses a hydrogen atom or a substituent.

As the substituents which are expressed by the above-mentioned $R_{41}$, a halogen atom, an alkyl group, a cycloalkyl group, an alkenyl group, a cycloalkenyl group, an alkinyl group, an aryl group, a heterocyclic group, an acyl group, a sulfonyl group, a sulfinyl group, a phosphonyl group, a carbamoyl group, a sulphamoyl group, a cyano-group, a spiro-compound residue, a bridged hydrocarbon compound residue, an alkoxy group, an aryloxy group, a heterocyclicoxy group, a silocy group, an acyloxy group, a carbamoyloxy group, an amino group, an acylamino group, a sulfonamido group, an imido group, an ureido group, a sulfamoylamino group, an alkoxycarbonylamino group, an aryloxycarbonylamino group, an alkoxycarbonyl group, an aryloxycarbonyl group, an alkylthio group, an arylthio group, and a heterocyclicthio group, for example, can be given.

As halogen atoms, an chlorine atom and a bromine atom, for example, can be cited, and particularly a chlorine atom is desirable.

For the alkyl group expressed by $R_{41}$, a group with a number of carbon atoms ranging from 1 to 32 is preferable, and, for the alkenyl group and the alkinyl group, one with a number of carbon atoms in the range from 2 to 32 is preferable, and, for the cycloalkyl group and the cycloalkenyl group, one with a number of carbon atoms in the range from 3 to 12—particularly one with a number of carbon atoms in the range from 5 to 7 is preferable. The alkyl group, the alkenyl group, and the alkinyl group may be one with either a straight chain or branched chain.

Also, these alkyl group, alkenyl group, alkinyl group, cycloalkyl group, and cycloalkenyl group may have substituents (for example, in addition to those with aryl, cyano, halogen atom, heterocyclic, cycloalkyl, cycloalkenyl, spiro-compound residue, bridged hydrocarbon compound residue, those sustituents which perform their substitution by way of a carbonyl group, such as acyl, carboxy, carbomoyl, alkoxycarbonyl, and aryloxycarbonyl, and, moreover, those which perform their substitution by way of a hetero-atom {specifically, those which perform their substitution by way of an oxygen atom, such as hydroxy, alkoxy, allyloxy, heterocyclicoxy, cyloxy, acyloxy, and carbamoyl, those which perform their substitution by way of a nitrogen atom, such as nitro, amino (including dialkylamino, etc.), sulfamoyl amino, alkoxycarbonyl amino, aryloxycarbonylamino, acylamino, sulfonamide, imide, and ureide, those which perform their substitution by way of a sulfur atom, such as alkylthio, sulfinyl, and sulfamoyl, and those which perform their substitution by way of phosphor atom, such as phosphonyl}].

In concrete terms, a methyl group, an ethyl group, an isopropyl group, a t-butyl group, a pentadecyl group, a heptadecyl group, a 1-hexylnonyl group, a 1,1'-dibenzylnonyl group, a 2-chlor-t-butyl group, a trifluoromethyl group, a 1-ethoxytridecyl group, a 1-methoxyisopropyl group, a methanesulfonylethyl group, a 2,4-di-t-amylphenoxymethyl group, an anilino group, a 1-phenylisopropyl group, a 3-m-butanesulfonaminophenoxypropyl group, a 3-4'-{a-[4"(p-hydroxybenzenesulfonyl)phenoxy]dodecanoylamino}phenylpropyl group, 3-{4'-[α-(2",4"-di-t-amylphenoxy)butaneamido]-phenyl}-propyl group, a 4-[α-(0)-chlorophenoxy)tetradecanamidephenoxy]propyl group, an aryl group, a cyclobenzyl group, a cyclohexyl group, and so forth, for example, can be mentioned.

As an aryl group which is expressed by $R_{41}$, a phenyl group is preferable, and this group may have a substituent (for example, an alkyl group, an alkoxy group, an acylamino group, etc.).

In concrete terms, a phenyl group, a 4-t-butyl-phenyl group, a 2,4-di-t-amylphenyl group, a 4-tetradecanamidophenyl group, a hexadesiloxyphenyl group, a 4'-[α-(4"-t-butylphenoxy)tetradecanamido]-phenyl group, and so on can be mentioned.

As the heterocyclic group which is expressed by $R_{41}$, one with five to seven members is preferable, and such a group may have a substitution or a condensation in it. Specifically, a 2-furyl group, a 2-thienyl group, a 2-pyrimidinyl group, a 2-benzothiazolyl group, etc. can be cited.

As the acyl group which is expressed by $R_{41}$, alkylcarbonyl groups, such as an acetyl group, a phenyl acetyl group, a dodecanoyl group, a α-2,4-di-t-amylphenoxybutanoyl group, etc. and arylcarbonyl groups, such as a benzoyl group, a 3-pentadecyloxybenzoyl group, a p-chlorbenzoyl group, etc., for example, may be mentioned.

As the sulfonyl group which is expressed by $R_{41}$, alkylsulfonyl groups, such as a methylsulfonyl group and a dodecylsulfonyl group, and arylsulfonyl groups, such as a benzenesulfonyl group and a p-toluenesulfonyl group, and so on can be cited.

As the sulfinyl group which is expressed by $R_{41}$, alkylsulfinyl groups, such as an ethylsulfinyl group, an octylsulfinyl group, and a 3-phenoxybutylsulfinyl group, and arylsulfinyl groups, such as a phenylsulfinyl group and an m-pentadecylphenylsulfinyl group, and so forth can be cited.

As the phosphonyl group which is expressed by $R_{41}$, alkylphosphonyl groups, such as a butyloctylphosphonyl group, alkoxyphosphonyl groups, such as an octyloxyphosphonyl group, aryloxyphosphonyl groups, such as a phenoxyphosphonyl group, arylphosphonyl groups, such as a phenylphosphonyl group, and so on can be cited.

For the carbamoyl group which is expressed by $R_{41}$, the alkyl group, the aryl group, prefarably a pheny group, etc. may have a substituent For example, an N-metnylcarbamoyl group, an N,N-dibutylcarbamoyl group, an N-(2-pentadecyloctylethyl) carbamoyl group, an N-ethyl-N-dodecylcarbamoyl group, an N-{3-(2,4-di-t-amylphenoxy)propyl}carbamoyl group, and so forth can be cited.

The sulfamoyl group which is expressed by $R_{41}$ may have an alkyl group, an aryl group (preferably a phenyl group), etc. by substituent and, for example, an N-propylsulfamoyl group, an N,N-diethylsulfamoyl group, an N-(2-pentadecyloyethyl) sulfamoyl group, an N-ethyl-N-dodecylsulfamoyl group, an N-phenylsulfamoyl group and so forth can be mentioned.

As the spiro-compound residue which is expressed by $R_{41}$, a spiro-[3.3]-heptane-1-yl, etc. can be cited.

As the bridged hydrocarbon residue which is expressed by $R_{41}$, a bicyclo [2.2.1]heptane-1-yl, a tricyclo[3.3.1.1$^{3,7}$]decan-1-yl, a 7,7-dimethyl-bicyclo-[2.2.1]-heptane-1-yl, and so forth can be cited.

The alkoxy group which is expressed by $R_{41}$ may have by substitution any group out of those cited as substituents for the alkyl group as mentioned above, and, for example, a methoxy group, a propoxy group, a 2-ethoxyethoxy group, a pentadecyloxy group, a 2-dodecyloxyethoxy group, a phenethyloxyethoxy group, and so on can be cited.

As the aryloxy group which is expressed by $R_{41}$, phenyloxy is preferable, and the aryl nucleus, moreover, may be substitution have any of the groups listed as substituents or atoms for the above-mentioned aryl group, and, for example, a phenoxy group, a p-t-butyl-phenoxy group, an m-pentadecylphenoxy group, etc. can be cited.

As the heterocyclicoxy group which is expressed by $R_{41}$, such a group having a five- to seven-membered ring is preferable, and the said heterocycle may moreover have a substituent, for which a 3,4,5,6-tetrahydropyranyl-2-oxy group, and a 1-phenyltetrazole-5-oxy group may be cited.

The siloxy group which is expressed by $R_{41}$ may moreover have such a group as an alkyl group by substitution, and, for example, a trimethylsiloxy group, a triethylsiloxy group, a dimethylbutylsiloxy group, and so forth can be mentioned.

As the acyloxy group which is expressed by $R_{41}$, an alkylcarbonyloxy group, an arylcarbonyloxy group, and so on, for example, can be cited. Furthermore, such a group may have a substituent. Specifically, an acetyloxy group, an α-chlorocetyloxy group, a benzoyloxy group, and so on can be cited.

The carbamoyloxy group which is expressed by $R_{41}$ may have any of an alkyl group, an aryl group, and so on by substitution. For example, an N-ethylcarbamoyloxy group, an N,N-diethylcarbamoyloxy group, an N-phenylcarbamoyloxy group, and so forth can be cited.

The amino group which is expressed by $R_{41}$ may have an alkyl group, an aryl group (preferably a phenyl group), and so forth by substitution, and, for example, an ethylamino group, an anilino group, an m-chloranilino group, a 3-pentadecyloxycarbonylanilino group, a 2-chlor-5-hexadecaneamidoanilino group, etc. can eb cited.

As the acylamino group expressed by $R_{41}$, an alkylcarbonylamino group, an arylcarbonylamino group (preferably a phenylcarbonylamino group), and so on can be mentioned. It may moreover have a substituent. In concrete terms, an acetoamido group, an α-ethylpropaneamido group, an N-phenylacetoamido group, and a dodecaneamido group, a 2,4-di-t-amylphenoxyacetoamido group, an α-3-t-butyl 4-hydroxyphenoxybutaneamido group, etc. can be cited.

As the sulfonamido which is expressed by $R_{41}$, an alkyl sulfonylamino group, an arylsulfonylamino group, and so forth can be mentioned, and any such group, moreover, may have a substituent. In concrete terms, a methylsulfonylamino group, a pentadecylsulfonylamino group, a benzenesulfonamido group, a p-toluenesulfonamido group, a 2-methoxy-5-t-amylbenzenesulfonamido group, and so forth can be cited.

The imide group which is expressed by $R_{41}$ may be either an open chain group or a cyclic one, and any such group may have a substituent, for which a succinic acid imido group, a 3-heptadecyl succinic acid imido group, a phthalimido group, and a glutaric imido group, and so forth can be cited.

The ureido group which is expressed by $R_{41}$ may have an alkyl group, an aryl group (preferably a phenyl group), etc. by substitution, and, for example, an N-ethylureido group, an N-methyl-N-decylureido group, an N-phenylureido group, an N-p-tolylureido group, and so forth can be cited.

The sulfamoylamino group which is expressed by $R_{41}$ may have an alkyl group, an aryl group (preferably a phenyl group), and so forth by substitution, and, for example, an N,N-dibutylsulfamoylamino group, an N-methylsulfamoylamino group, an N-phenylsulfamoylamino group, and so forth can be cited.

The alkoxycarbonylamino group which is expressed by $R_{41}$ may moreover have a substituent, and, for example, a methoxycarbonylamino group, a methoxyethoxycarbonylamino group, an otadecyloxycarbonylamino group, and so forth can be mentioned.

The aryloxy carbonylamino group, which is expressed by $R_{41}$ may have a substituent, and, for example, a phenoxycarbonylamino group, a 4-methylphenoxycarbonylamino group can be given.

The alkoxycarbonyl group which is expressed by $R_{41}$ may moreover have a substituent, and a methoxycarbonyl group, a butyloxycarbonyl group, and a dodecyloxycarbonyl group, and an octadecyloxycarbonyl group, an ethoxymethoxycarbonyloxy group, a benzyloxycarbonyl group, etc. can be mentioned.

The aryloxycarbonyl group which is expressed by $R_{41}$ may moreover have a substituent, and, for example, a phenoxycarbonyl group, a p-chlorophenoxycarbonyl group, an m-pentadecyloxyphenoxycarbonyl group, and so on may be given.

The alkylthio group which is expressed $R_{41}$ may moreover have a substituent, and, for example, an ethylthio group, a dodecylthio group, an octadecylthio group, a phenethylthio group, and a 3-phenoxypropylthio group can be cited.

For the arylthio group which is expressed by $R_{41}$, a phenylthio group is preferable, and, moreover, the group may have a substituent, for which a phenylthio group, a p-methoxyphenylthio group, a 2-t-octylphenylthio group, a 3-octadecylphenylthio group, a 2-carboxyphenylthio group, a p-acetoaminophenylthio group, and so forth, for example, can be mentioned.

For the heterocyclic thio group which is expressed by $R_{41}$, a heterocyclic thio group with five to seven members is preferable, and it may moreover have a condensed ring or may have a substituent. For example, a 2-pyridylthio group, a 2-benzothiazolylthio group, a 2,4-diphenoxy-1,3,5-thoriazole-6-thio group can be mentioned.

As the substituents which can detach themselves by a reaction with an oxidized product of the color developing agent as expressed by $X_1$, those groups which performs their substitution by way of a carbon atom, an oxygen atom, a sulfur atom, or a nitrogen atom, in addition to a halogen atom (a chlorine atom, a bromine atom, a fluorine atom, etc.) can be cited.

As the groups which perform their substitution by way of a carbon atom, those groups which are expressed by the general formula given below (in which $R_{41}'$ is synonymous with the above-mentioned $R_{41}$, $Z_1'$ is synonymous with the above-mentioned $Z_1$, and $R_{42}'$ and $R_{43}'$ express a hydrogen atom, an aryl group, an alkyl group, or a heterocylic group), a hydroxymethyl group, and a triphenylmethyl group, for example, can be cited, in addition to a carboxyl group.

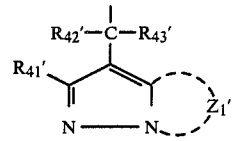

As the groups which perform their substitution by way of an oxygen atom, an alkoxy group, an aryloxy group, a heterocyclicoxy group, an acyloxy group, a sulfonyloxy group, a sulfonyloxy group, an alkoxycarbonyloxy group, an aryloxycarbonyloxy group, an alkyloxalyloxy group, an alkoxyoxallyloxy group, and so forth, for example, can be mentioned.

The alkoxy group may moreover have a substituent, and, for example, such groups as an ethoxy group, a 2-phenoxyethoxy group, a 2-cyanoethoxy group, a phenethloxy group, and a p-chlorbenzyloxy group can be cited.

For the aryloxy group, a phenoxy group is preferable, and the aryl group, moreover, may have a substituent. In concrete terms, a phenoxy group, a 3-methylphenoxy group, a 3-dodecylphenoxy group, a 4-methanesulfonamidophenoxy group, a 4-[α-(3'-pentadecilphenoxy)butaneamido]phenoxy group, a hexadecylcarbamoilmethoxy group, a 4-cyanophenoxy group, a 4-methanesulfonylphenoxy group, a 1-naphthyloxy group, a p-methoxyphenoxy group, and so forth can be cited.

For the heterocyclicoxy group, a five- to seven-membered heterocyclicoxy group is preferable, and such a group may also be a condensed ring and may also have a substituent. Specifically, a 1-phenyltetrazolyloxy group, a 2-benzothiazolyloxy group, and so forth can be cited.

As the acyloxy group, such alkylcarbonyloxy groups as an acetoxy group and a butanoloxy group, such alkenylcarbonyloxy groups as a cinnamoyloxy group, and such arylcarbonyloxy groups as a benzoyloxy group, for example, can be cited.

As the sulfonyloxy group, a butanesulfonyloxy group and a methanesulfonyloxy group, for example, can be cited.

As the alkoxycarbonyloxy group, an ethoxycarbonyloxy group and a benzyloxycarbonyloxy group, for example, can be cited.

As the aryloxycarbonyl group, a phenoxycarbonyloxy group, etc., for example, can be cited.

As the alkyloxalyloxy group, a methyloxalyloxy group, for example, can be cited.

As the alkoxyoxalyloxy group, an ethoxyoxalyloxy group and so forth can be cited.

As the groups which perform their substitution by way of a sulfur atom, an alkylthio group, an arylthio group, a heterocyclic thio group, and an alkyloxythiocarbonylthio group for example, can be mentioned.

As the alkylthio group, a butylthio group, a 2-cyanoethylthio group, a phenethlthio group, a benzylthio group, and so on can be cited.

As the arylthio group, a phenylthio group, a 4-methanesulfonamidophenylthio group, a 4-dodecylphenetylthio group, a 4-nonafluoropentaneamidophenetylthio group, 4-carboxyphenylthio group, a 2-ethoxy-5-t-butylphenylthio group, and so forth can be cited.

As the heterocyclic thio group, a 1-phenyl-1,2,3,4-tetrazolyl-5-thio group, 2-benzothiazolylthio group, and so on, for example, can be cited.

As the alkyloxythiocarbonylthio group, a dodecyloxythiocarbonylthio group, and so on can be cited.

As the groups which perform their substitution by way of a nitrogen atom as mentioned above, those groups which are indicated by the general formula,

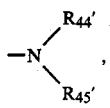

can for example, be cited. Here, $R_{44}'$ and $R_{45}'$ express a hydrogen atom, an alkyl group, an aryl group, a heterocyclic group, a sulfamoyl group, a carbamoyl group, an acyl group, a sulfonyl group, an aryloxycarbonyl group, and an alkoxycarbonyl group, and $R_{44}'$ and $R_{45}'$ may form a heterocyclic ring by forming a bond with each other. However, it never occurs that both $R_{44}'$ and $R_{45}'$ are hydrogen atoms.

The alkyl group may be either a straight chain or a branched chain, and it is preferably such a group with a number of carbon atoms in the range from one to 22. Furthermore, the alkyl group may have a substituent, and, as such a substituent, an aryl group, an alkoxy group, an aryloxy group, an alkylthio group, an arylthio group, an alkylamino group, an arylamino group, an acylamino group, a sulfonamido group, an imino group, an acyl group, an alkylsulfonyl group, an arylsulfonyl group, a carbamoyl group, a sulfamoyl group, an alkoxycarbonyl group, an aryloxycarbonyl group, an alkyloxycarbonylamino group, an aryloxycarbonylamino group, a hydroxyl group, a carboxyl group, a cyano group, a halogen atom, for example, can be mentioned. As specific ones of the said alkyl group, an ethyl group, an octyl group, and a 2-ethylhexyl group, a 2-chloroethyl group, for example, can be mentioned.

As the aryl group which is expressed by $R_{44}'$ or $R_{45}'$, those groups which have a number of carbon atoms in the range from six to 32—above all, a phenyl group and a naphthyl group—are preferable, and the aryl group may have a substituent. For such substituents, those which are given as substituents for the alkyl group expressed by $R_{44}'$ and $R_{45}'$ mentioned above and also an alkyl group can be cited. As specific ones of the aryl group, a phenyl group, a 1-naphthyl group, and a 4-methylsulfonylphenyl group, for example, can be cited.

As the heterocyclic group which is expressed by $R_{44}'$ or $R_{45}'$, such a group with five to six members is preferable, and it may have a condensed ring and may have a substituent. As specific examples, a 2-furyl group, a 2-quinolyl group, a 2-pyrimidyl group, a 2-benzothiazolyl group, a 2-pyridyl group, etc. may be mentioned.

As the sulfamoyl group which is expressed by $R_{44}'$ or $R_{45}'$, an N-alkylsulfamoyl group, an N,N-dialkylsulfamoyl group, an N-arylsulfamoyl group, an N,N-diarylsulfamoyl group, and so on can be cited, and these alkyl groups and these aryl groups may have any of the substituents given with regard to the alkyl groups and aryl groups mentioned above. As specific examples of the sulfamoyl group, an N,N-dimethylsulfamoyl group, an N-methylsulfamoyl group, an N-dodecylsulfamoyl group, and an N-p-tolysulfamoyl group can be mentioned.

As the carbamoyl group which is expressed by $R_{44}'$ or $R_{45}'$, an N-alkylcarbamoyl group, and N,N-dialkylcarbamoyl group, an N,N-dialkylcarbamoyl group, an N-arylcarbamoyl group, an N,N-diarylcarbamoyl group, and so forth can be cited, and these alkyl groups and aryl groups may have any of the substituents given with respect to the alkyl groups and aryl groups mentioned above. As specific examples of the carbamoyl group, an N,N-diethylcarbamoyl group, an N-methylcarbamoyl group, an N-dodecylcarbamoyl group, and N-p-cyanophenylcarbamoyl group, and an N-p-tolycarbamoyl group, for instance, can be given.

As the acyl group which is expressed by $R_{44}'$, or $R_{45}'$, an alkylcarbonyl group, an arylcarbonyl group, and a heterocycliccarbonyl group, for example, can be mentioned, and the said alkyl group, the said aryl group, and the said heterocyclic group may have a substituent. As specific groups in the acyl group, a hexafluorobutanoyl group, a 2,3,4,5,6-pentafluorobenzoyl group, an acetyl group, a benzoyl group, a naphthoyl group, a 2-furylcarbonyl group, and so forth can be mentioned.

As the sulfonyl group which is expressed by $R_{44}'$ or $R_{45}'$, an alkylsulfonyl group, an arylsulfonyl group, and a heterocyclic-sulfonyl group can be mentioned. Such a group may have a substituent, and, as specific ones of such groups, an ethanesulfonyl group, a benzenesulfonyl group, an octanesulfonyl group, a nephthalenesulfonyl group, a p-chlorobenzenesulfonyl group, and so forth can be cited.

The aryloxycarbonyl group which is expressed by $R_{44}'$ or $R_{45}'$ may have as its substituent any of the substituents given as such for the aryl group mentioned above, and, as specific substituents, a phenoxycarbonyl group, etc. can be cited.

The alkoxycarbonyl group which is expressed by $R_{44}'$ or $R_{45}'$ may have any of the substituents given as such for the alkyl group mentioned above, and, as specific substituents, a methoxycarbonyl group, a dedecyloxycarbonyl groups, a benzyloxycarbonyl group, and so forth can be cited.

For a heterocycle formed by the bonding of $R_{44}'$ and $R_{45}'$, such a cycle with five to six memebrs is preferable, and it may be either saturated or unsaturated, and it may either be aromatic or non-aromatic, and it may comprise a condensed ring. As the heterocyclic group, an N-phthalimido group, an N-succinicimido group, a 4-N-urazolyl group, a 1-N-hydantoinyl group, a 3-N-2,4-dioxooxazolydinyl group, a 2-N-1, 1-dioxo-3-(2H)-oxso-1,2-benzthiazolyl group, a 1-pyrolyl group, a 1-pyrolydinyl group, a 1-pyrazolyl group, a 1-pyrazolydinyl group, a 1-piperidinyl group, a 1-pyrolynyl group, a 1-imidazolyl group, a 1-imidazolynil group, a 1-indolyl group, a 1-isoindolynil group, a 2-isoindolyl group, a 2-indolynil group, a 1-benzotolyazolyl group, a 1-benzoimidazolyl group, a 1-(1,2,4-triazolyl) group, a 1-(1,2,3-triazolyl) group, 1-(1,2,3,4-tetrazolyl) group, a N-morpholinyl group, a 1,2,3,4-tetrahydroquinolyl group, a 2-oxo-1-pyrolidinyl group, a 2-1H-pyridone group, a phthalazione group, a 2-oxo-1-pyperidinyl group, and so forth may be cited, and any of these heterocyclic groups are may be substituted with an alkyl group, an aryl group, an alkyloxy group, an aryloxy group, an acyl group, a sulfonyl group, an alkylamino group, an arylamino group, an acylamino group, a sulfonamino group, a carbamoyl group, a sulfamoyl group, an alkylthio group, an arylthio group, a ureido group, an alkoxycarbonyl group, an aryloxycarbonyl group, an imido group, a nitro group, a cyano group, a carboxy group, a halogen atom, and so forth.

Furthermore, as nitrogen-containing heterocyclic rings formed by Z or Z', a pyrazole ring, an imidazole ring, a triazol ring, or a tetrazole ring, etc. can be cited, and, as the susbtituents which the above-mentioned rings may have, those which have been mentioned with regard to the above-mentioned R can be cited.

Furthermore, in case the substituent (for example, $R_{41}$, or any of $R_{42} \sim R_{48}$) on a heterocycle in the general formula [I] and in any of the general formula [II]~[VII] mentioned below has a part (here, $R_{41}''$, X and $Z_1''$ are synonymous with the $R_{41}$, $X_2$, and $Z_1$ in the general formula [II], such a substituent forms what is generally known as a bis-form type

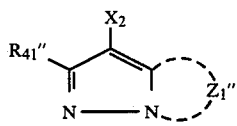

coupler, and such substituents are, of course, included in the present invention. Moreover, the rings which are formed by $Z_1$, $Z_1'$, and $Z_1''$ and $Z_2$ mentioned later may further be a product of condensation of another ring (for example, five- to seven-membered cycloalkene). For example, $R_{45}$ and $R_{46}$ in the general formula [V], or $R_{47}$ and $R_{48}$ in the general formula [V], may make a bond with each other to form a ring (for example, a five- to seven-membered cycloalkene or benzene ring).

What is expressed by the general equation [I] may be expressed more specifically in the general formulae [II]~[VII] given in the following:

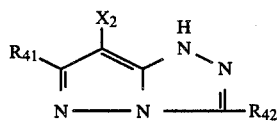

General formula [II]

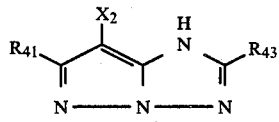

General formula [III]

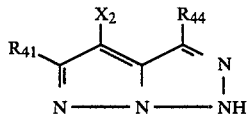

General formula [IV]

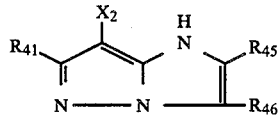

General formula [V]

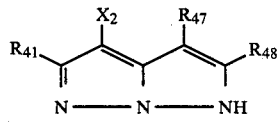

General formula [VI]

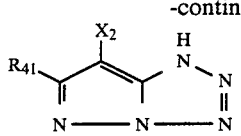

General formula [VII]

In the above-mentioned general formulae [II]~[VII], $R_{41} \sim R_{48}$ and X are synonymous with the above-mentioned R and X.

Moreover, what is more preferable of those expressed in the general formula [I] is that which is expressed by the general formula [VIII] given in the following:

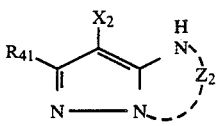

General formula [VIII]

In this formula, $R_{41}$, $X_2$, and $Z_2$ are synonymous with $R_{41}$, $X_2$, and $Z_1$ in the general formula [I].

The coupler particularly preferable among those magenta couplers which are expressed in the general formula [II]~[VII] given above is the magenta coupler expressed in the general formula [II].

Furthermore, speaking of the substituents on the heterocycles in the general formulae [I]~[VIII], $R_{41}$ in the general formulae [I]~[VIII], satisfies the condition 1 mentioned below is preferable, and what is more preferable is the case in which $R_{41}$, as the case may be, satisfies the conditions 1 and 2 mentioned below, and what is specially preferable is the case in which $R_{41}$, satisfies the condtiions 1, 2, and 3 mentioned in the following:

Condition 1: The atoms bonded directly to the heterocycle are carbon atoms.

Condition 2: Only one hydrogen atom is bonded to the carbon atom, or no hydrogen atom at all is so bonded.

Condition 3: All the bonds between the carbon atoms and the adjacent atoms are single bonds.

What is most desirable as the substituents $R_{41}$ on the heterocycle mentioned above is that which is expressed in the general equation [IX] given in the following:

In this formula, $R_{49}$, $R_{50}$, and $R_{51}$ respectively express a hydrogen atom, a halogen atom, an alkyl group, a cycloalkyl group, an alkenyl group, a cycloalkenyl group, an alkinyl group, an aryl group, a heterocyclic group, an acryl group, a sulfonyl group, a sulfinyl group, a phosphonyl group, a carbamoyl group, a sulfamoyl group, a cyano group, a spiro compound residue, a bridged hydrocarbon compound residue, an alkoxy group, an aryloxy group, a heterocyclic-oxy group, a siloxy group, an acyloxy group, a carbamoyloxy group, an amino group, an acylamino group, a sulfonamido group, an imido group, an ureido group, a sulfamoylamino group, an alkoxycarbonylamino group, an arylocycarbonylamino group, an alkoxycarbonyl group, an aryloxycarbonyl group, an alkylthio group, and an arylthio group, a heterocyclicthio group, and at least two of $R_9$, $R_{50}$, and $R_{51}$ are not hydrogen atoms.

Furthermore, two out of $R_{49}$, $R_{50}$, and $R_{51}$ given above—for example, $R_{49}$ and $R_{50}$—may form a bond with each other to develop a saturated or unsaturated ring (for example, a cycloalkane ring, cycloalkene ring, and heterocyclic ring), and may furthermore, form a bridged hydrocarbon compound residue by the bonding of $R_{11}$ with the ring.

The groups which are expressed by $R_{49} \sim R_{51}$ may have substituents, and, as the examples specific embodiments of the groups which are expressed by $R_{49} \sim R_{51}$ and, as the substituents which the groups may have, those specific examples and those substituents for the groups which $R_{41}$ expresses can be cited.

Moreover, as concrete examples of the ring formed by the bonding of $R_{49}$ and $R_{50}$ and the bridged hydrocarbon compound residue formed by $R_{49} \sim R_{51}$, for example, and the substituents which such a ring or residue may have, the concrete examples of the cycloalkyl ring, cycloalkenyl ring, heterocyclic ring, and bridged hydrocarbon compound residue which are expressed by $R_{41}$ in the general formula [I] mentioned above and their respective substituents can be cited.

The preferable ones even out of the substituents expressed in the general formula [IX] are those which come under the following:

(i) Two out of $R_{49} \sim R_{51}$ are alkyl groups.
(ii) One out of $R_{49} \sim R_{51}$—for example, $R_{51}$—is a hydrogen atom, and other two, $R_{49}$ and $R_{50}$, make a bond with each other to form cycloalkyl together with the radical carbon atom.

Moreover, what is more preferable of the substituents coming under (i) is in the one in which two out of $R_{49} \sim R_{51}$ are alkyl groups while another of them is a hydrogen atom or an alkyl group.

Here, the alkyl group and the cycloalkyl group may further have a substituent, and, as concrete exampels of the alkyl group, the cycloalkyl group, and their substitutes, those concrete exmpels of the alkyl group, cycloalkyl group, and their substitues as expressed by $R_{41}$ in the above-mentioned general formula [I] can be cited.

Furthermore, as the substituents of which the rings formed by $Z_1$ in the general formula [I] and by $Z_2$ in the general formula [VII] may have and as $R_{42} \sim R_{48}$ in the general formulae [II] $\sim$ [VI] those which are expressed by the general formula [X] given below are preferable.

General formula [X]

$$-R_{52}-SO_2-R_{53}$$

In this formula, $R_{52}$ expresses alkylene, and $R_{53}$ expresses alkyl, cycloalkyl, or aryl.

The alkylene which is indicated by $R_{52}$ should preferably have a number of carbon atoms 2 or more, and, more preferably, in the range from 3 to 6, in the straight chain part, and the chain may be either a straight chain or a branched chain. Also, this alkylene may have a substituent.

As examples of the substituents, those indicated as the substituents which the alkyl group may have, in case $R_{41}$ in the above-mentioned general formula [I] is an alkyl group, can be cited.

As a group which is preferable as substituent, phenyl can be mentioned.

Preferable concrete examples of the alkylene indicated by $R_{52}$ are given in the following:

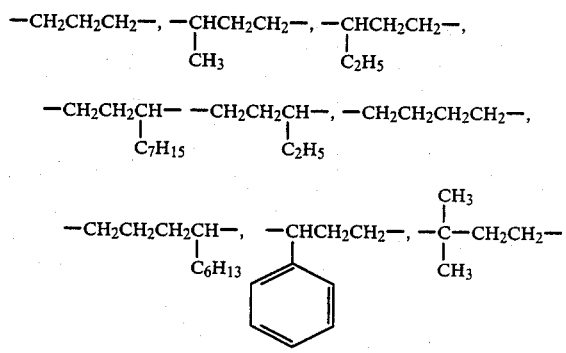

The alkyl group which is expressed by $R_{53}$ may have either a straight chain or a branched one.

Specifically, methyl, ethyl, propyl, iso-propyl, butyl, 2-ethylhexyl, octayl, dodecyl, tetradecyl, hexadecyl, octadecyl, 2-hexyldecyl, and so forth can be cited.

As the cycloalkyl group which is expressed by $R_{53}$, those with five to seven members are preferable, and, for example, cyclohexyl can be cited.

The alkyl and cycloalkyl which are expressed by $R_{53}$ may have a substitute, and, as examples of such substitutes, those cited as exampels for the substitutes for $R_{52}$ mentioned above may be cited.

Specifically as the aryl which is expressed by $R_{53}$, phenyl and naphthyl can be mentioned. The aryl group may have a substituent. As the substituents, those cited as examples of the substituents for $R_{52}$ mentioned above, for example, can be cited, in addition to alkyl groups either with a straight chain or with a branched chain.

Moreover, in case there are two or more substituents, such substituents may be either identical or different.

The specially preferable compounds even among those which are expressed by the general formula [I] are those expressed by the general formula given in the following:

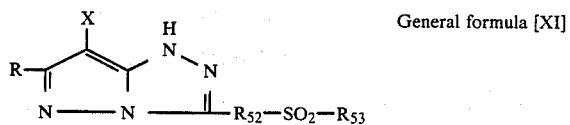

General formula [XI]

In this formula, R and X are synonymous with the R and X in the general formula [I], and $R_{52}$ and $R_{53}$ are synonymous with the $R_{52}$ and $R_{53}$ in the general formula [X].

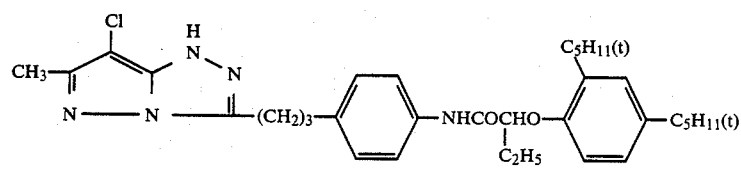

1

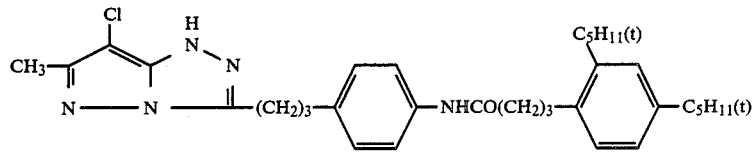
2
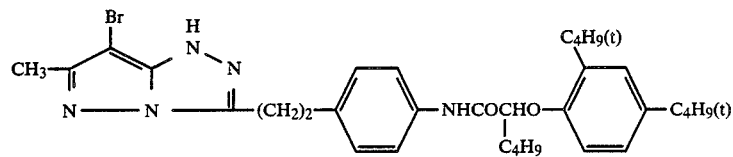
3
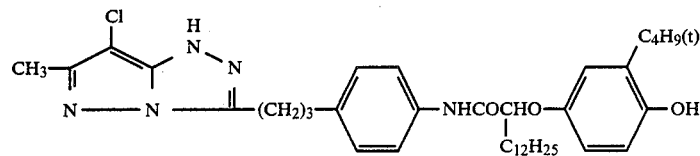
4
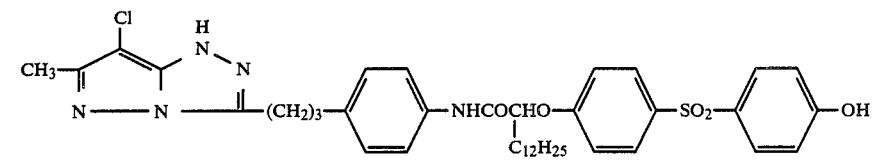
5
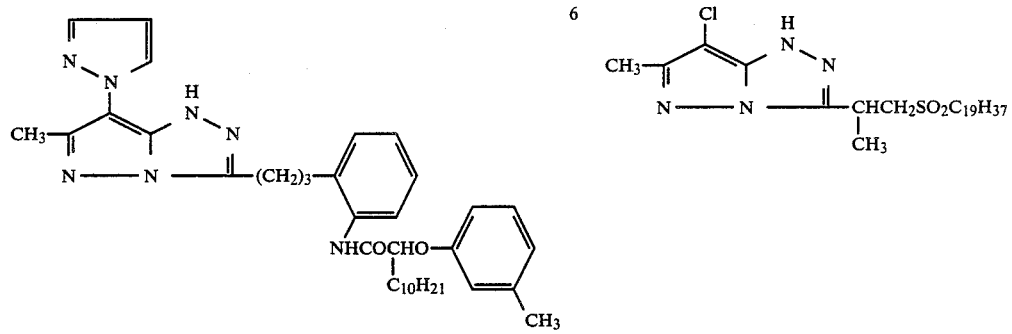
6
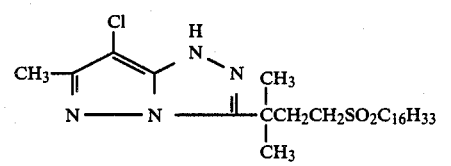
7
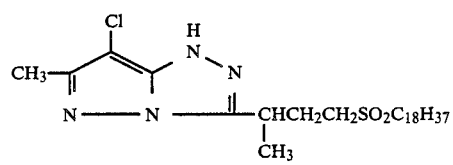
8
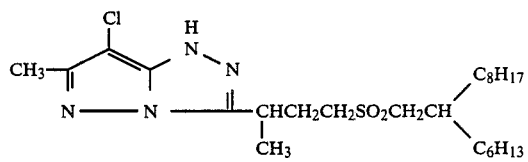
9
10
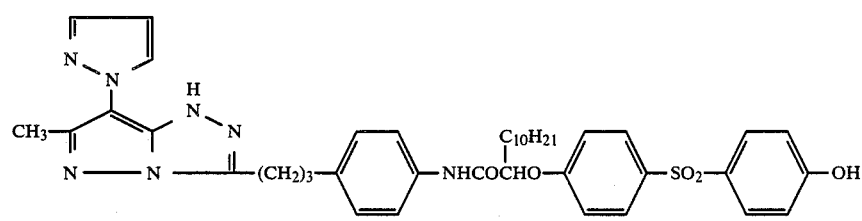
11

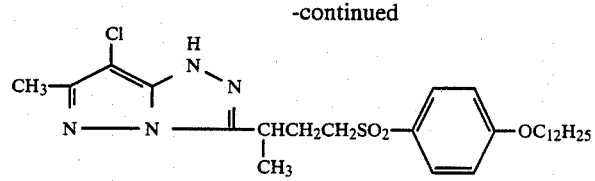
12
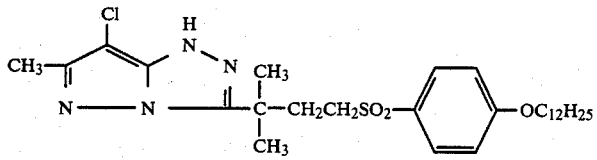
13
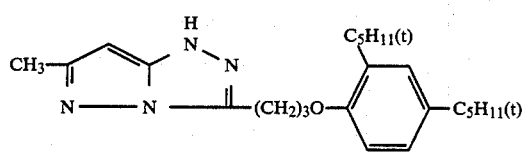
14
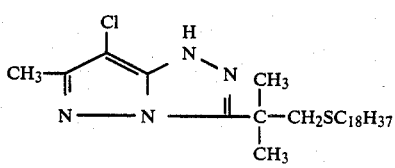
15
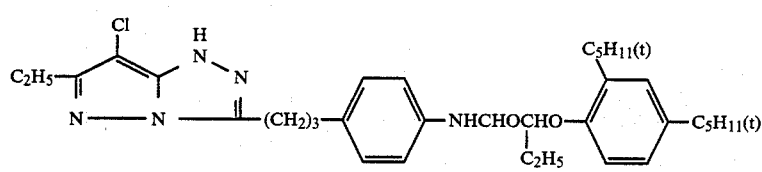
16
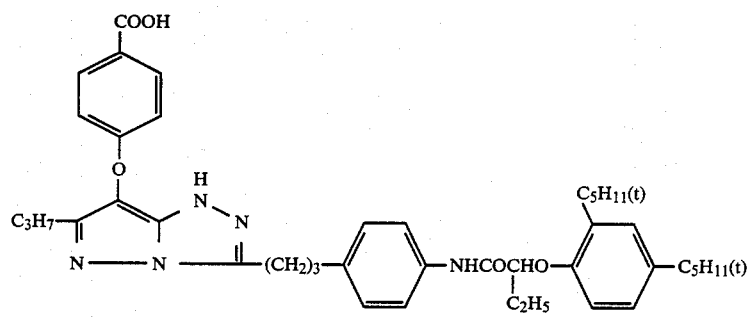
17
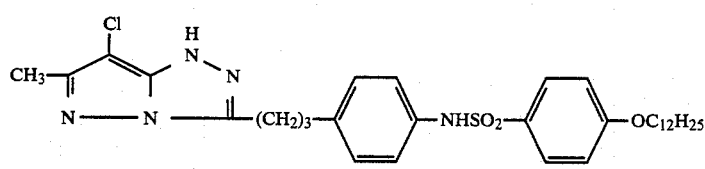
18
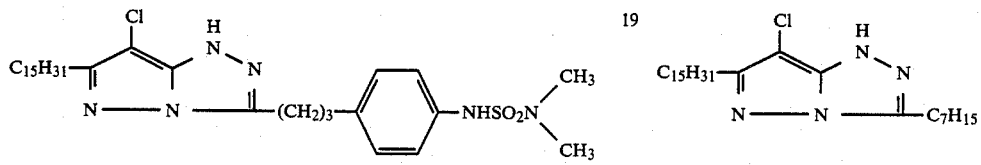
19 20
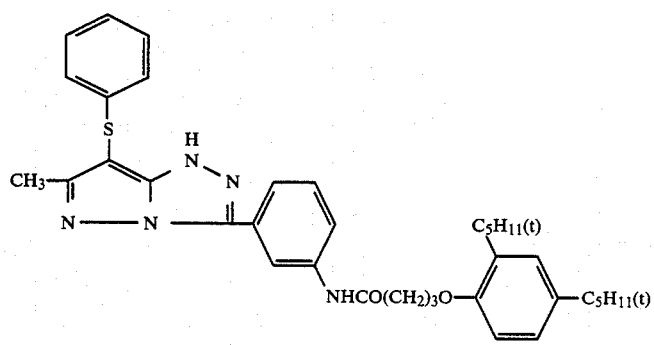
21

-continued
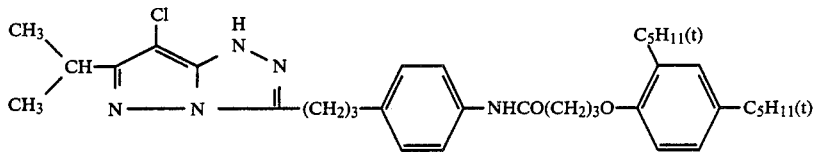
22
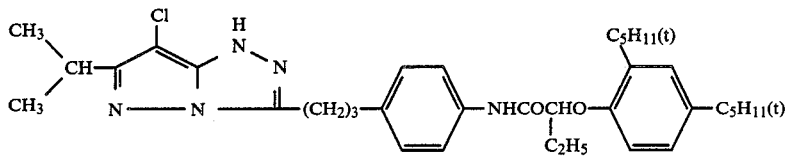
23
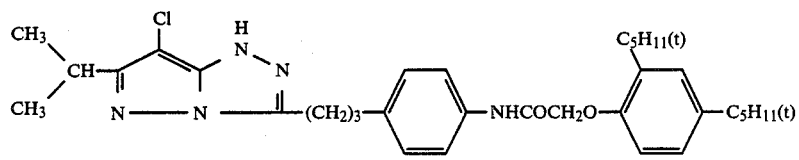
24
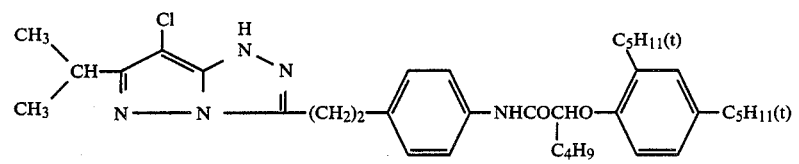
25
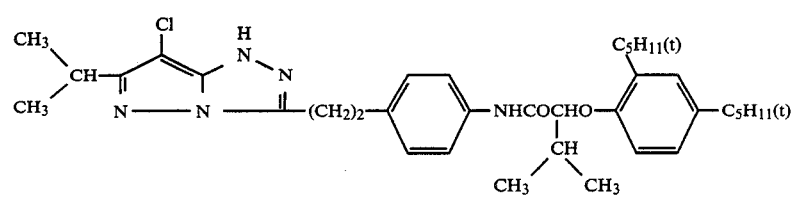
26
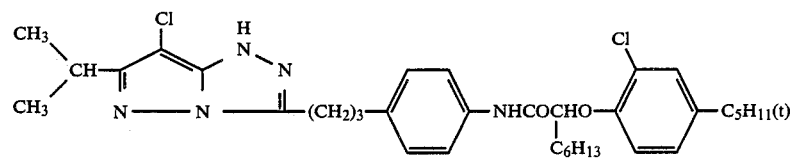
27
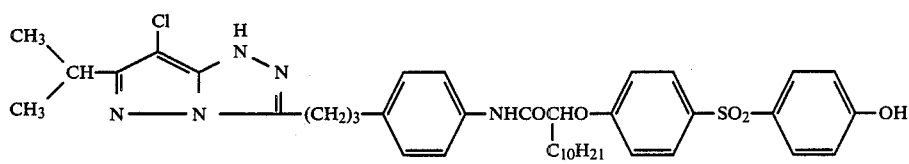
28
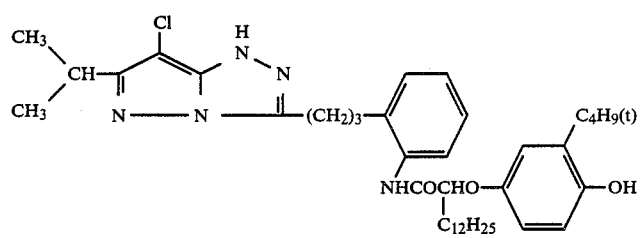
29
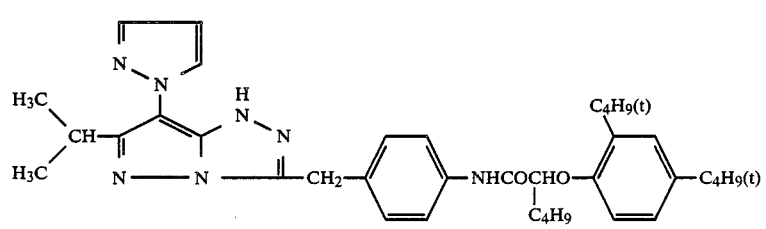
30

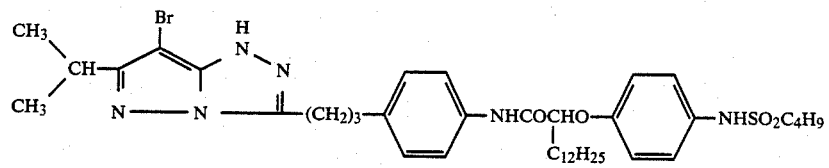
31
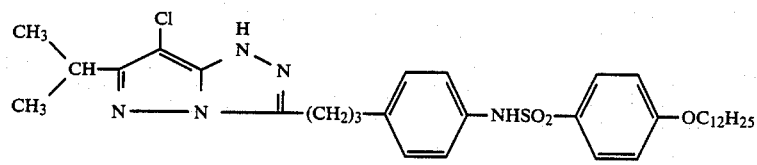
32
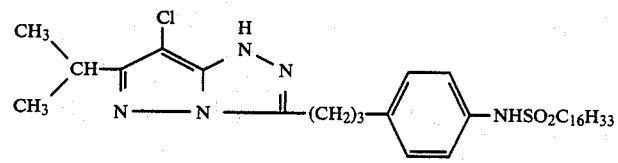
33
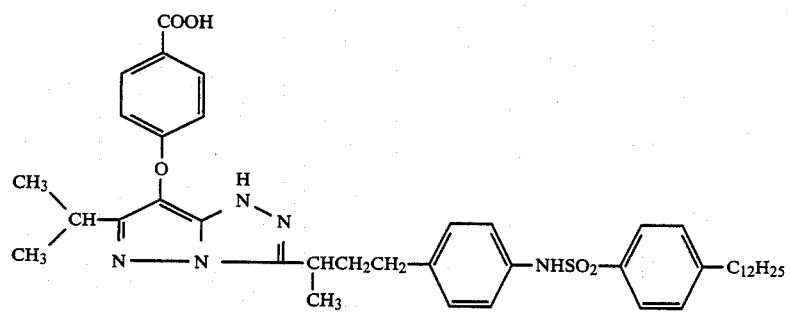
34
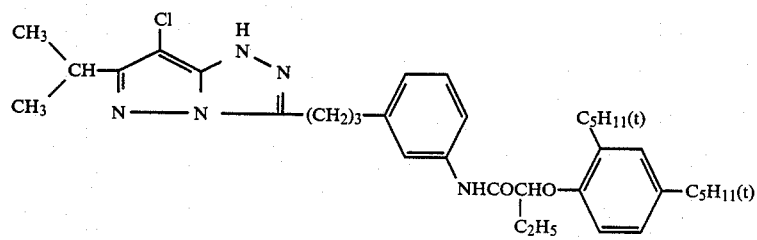
35
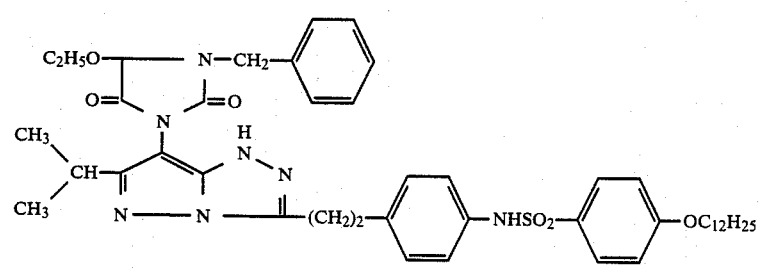
36

-continued
37
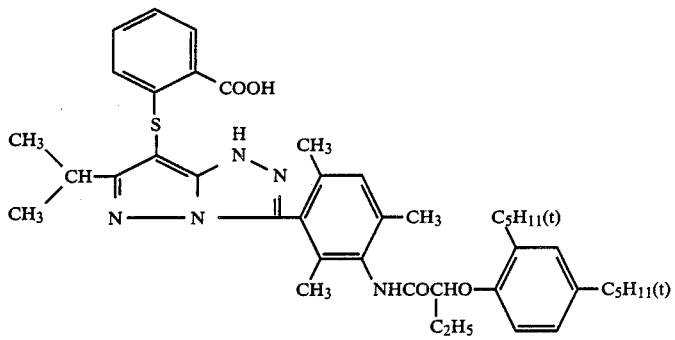
38
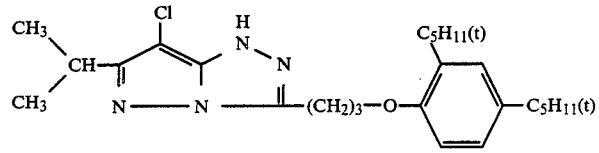
39
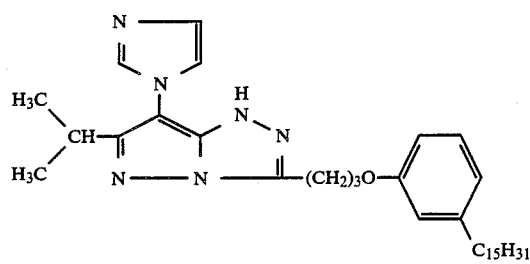
40
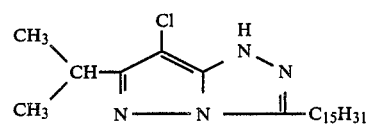
41
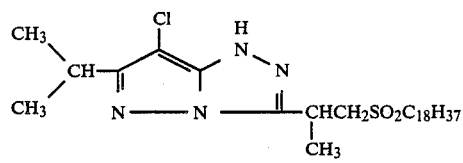
42
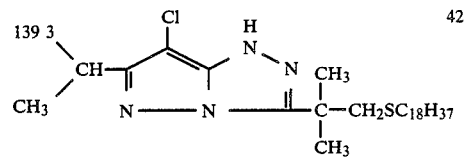
43
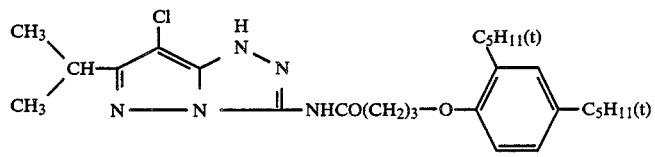
44
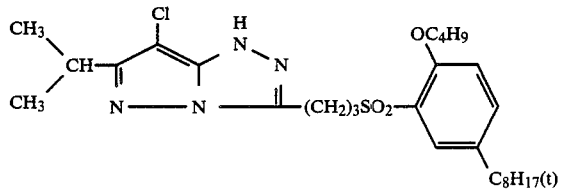
45
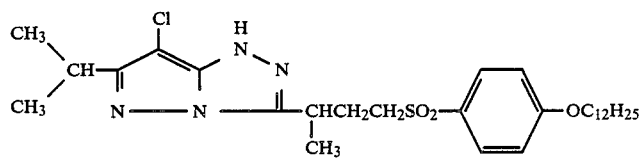
46
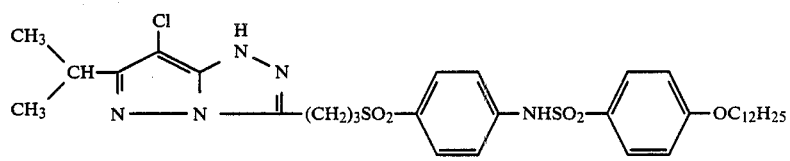

-continued
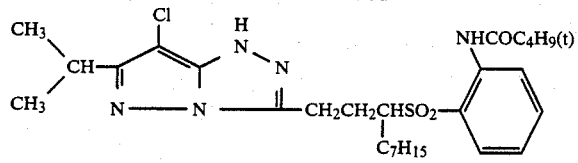
47
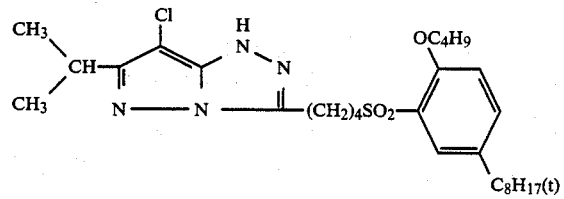
48
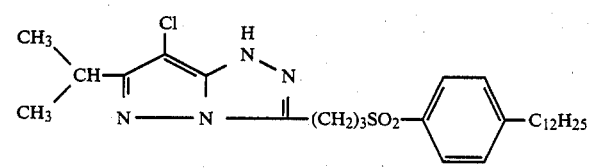
49
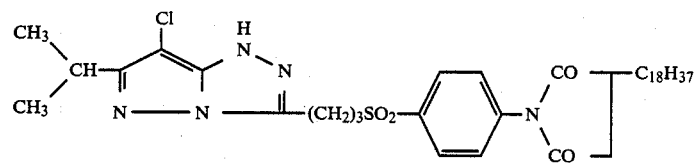
50
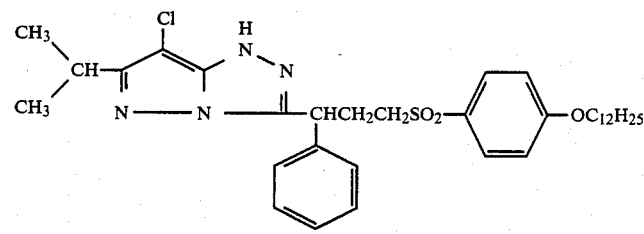
51
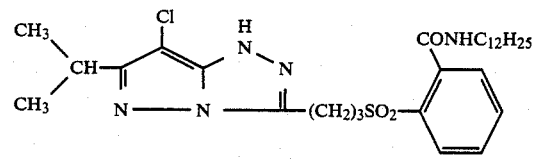
52
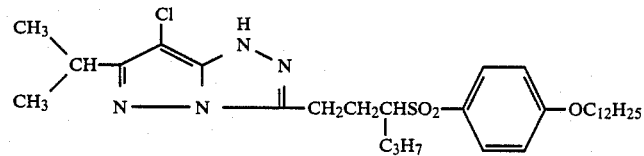
53
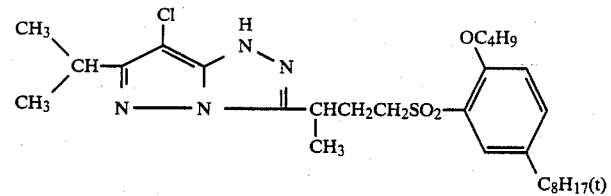
54
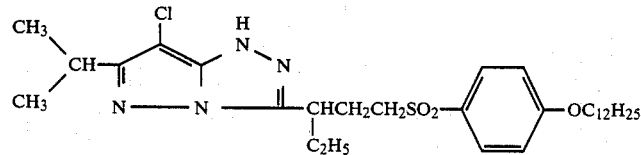
55

-continued
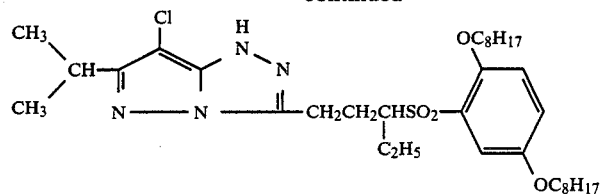
56
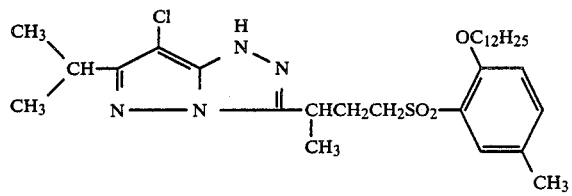
57
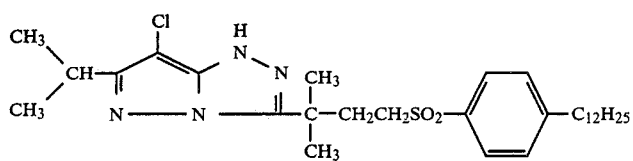
58
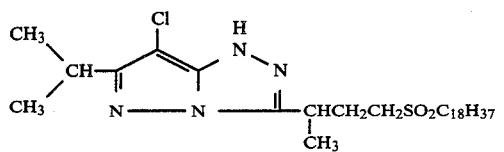
59
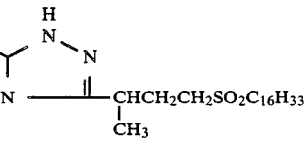
60
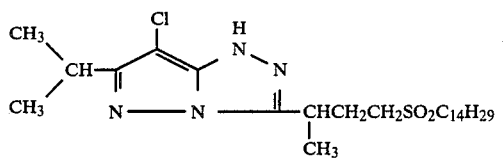
61
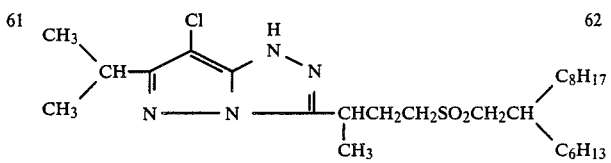
62
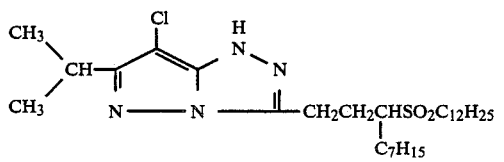
63
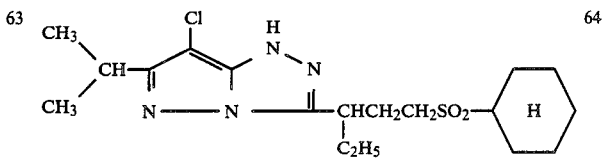
64
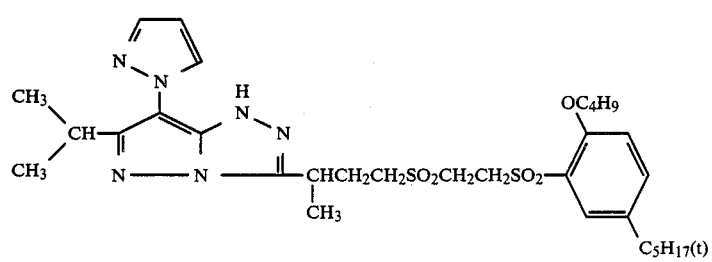
65
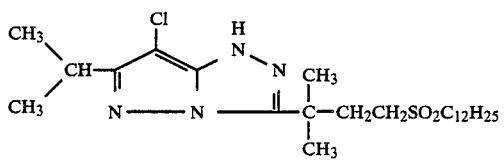
66
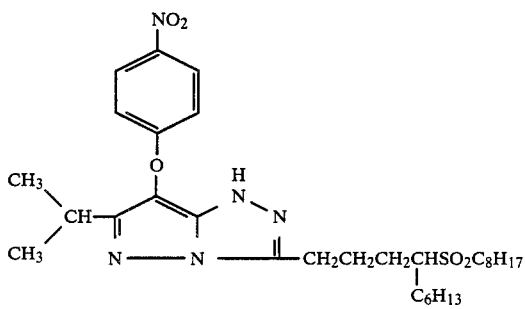
67

-continued
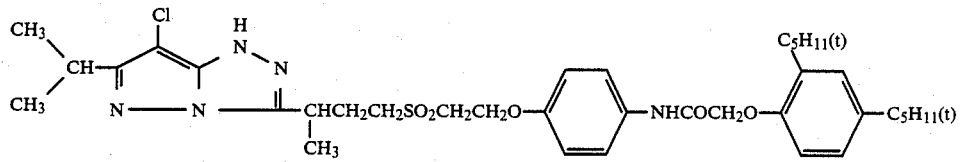
68
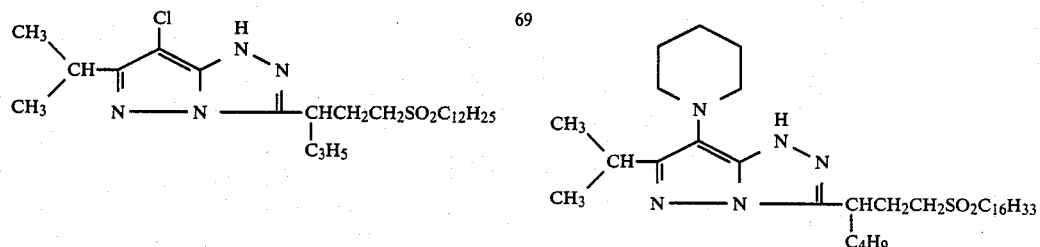
69
70
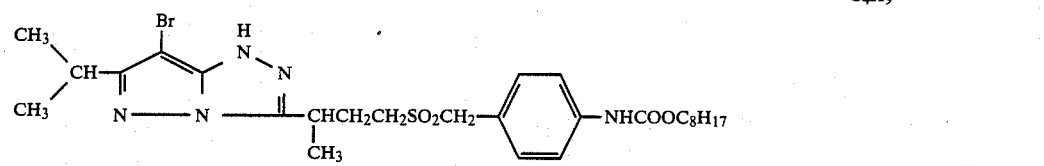
71
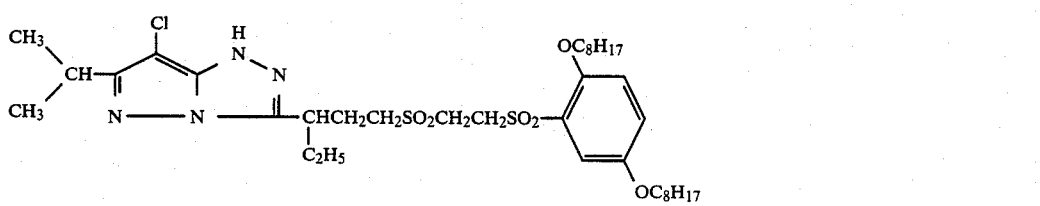
72
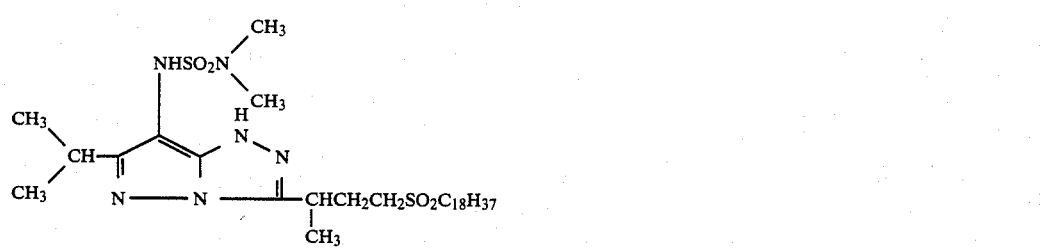
73
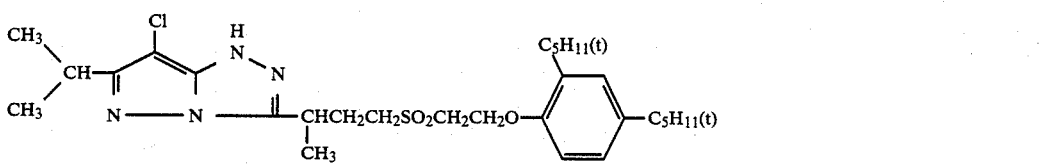
74
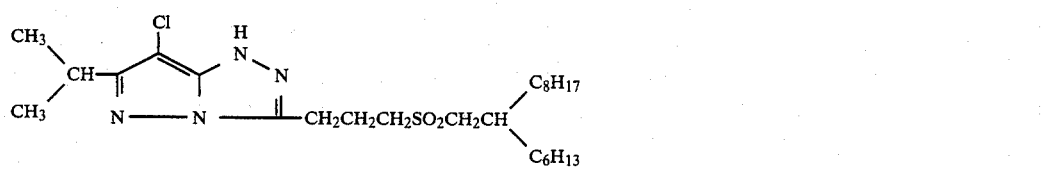
75
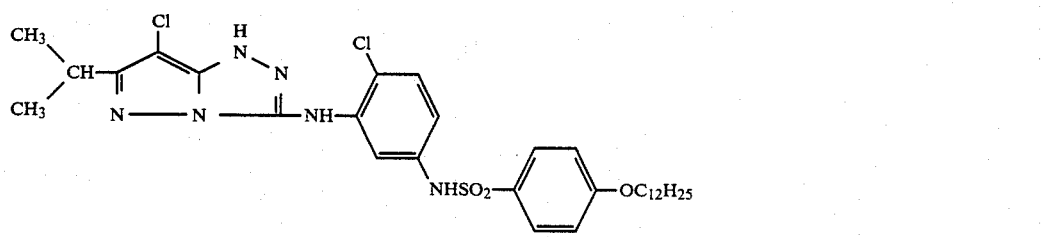
76

-continued
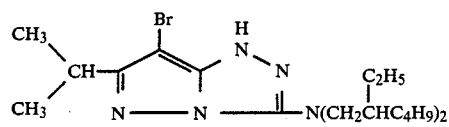
77
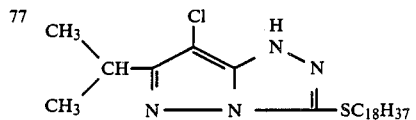
78
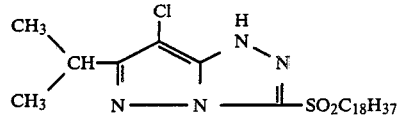
79
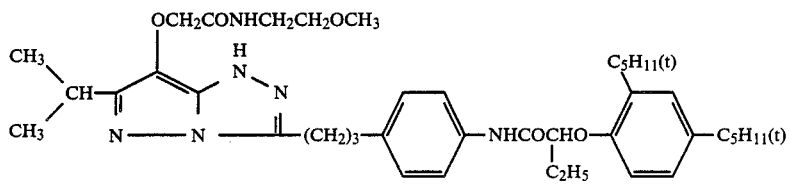
80
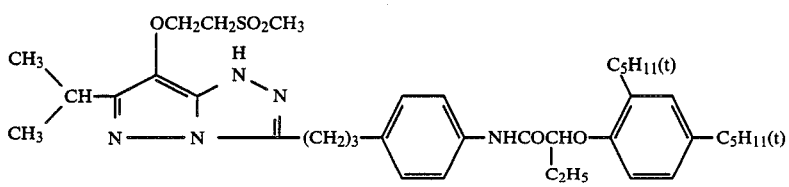
81
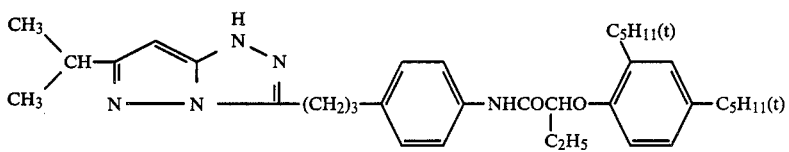
82
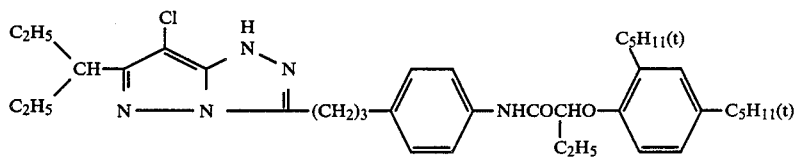
83
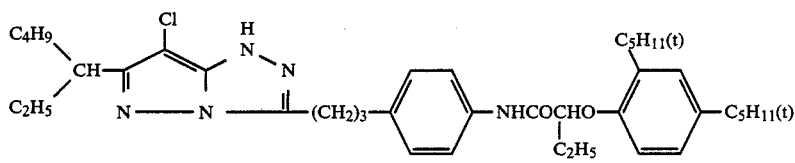
84
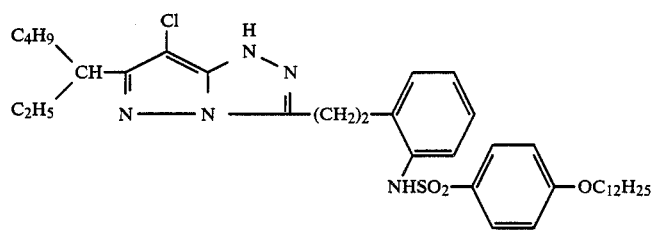
85
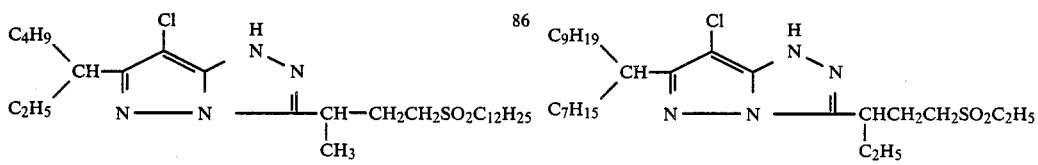
86    87

-continued
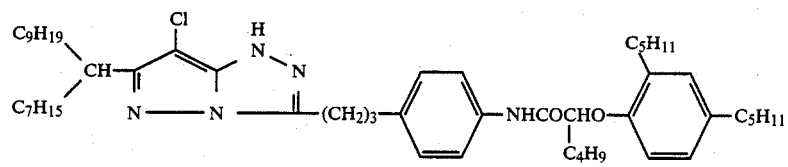 88
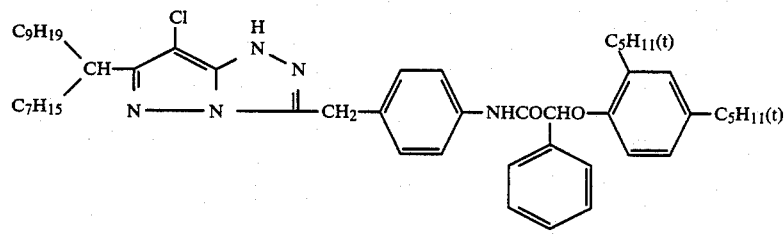 89
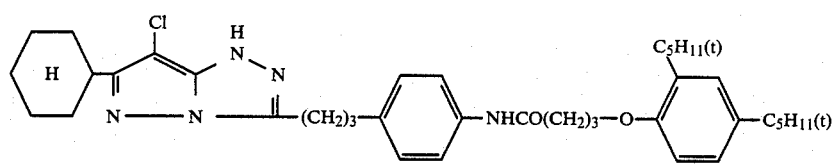 90
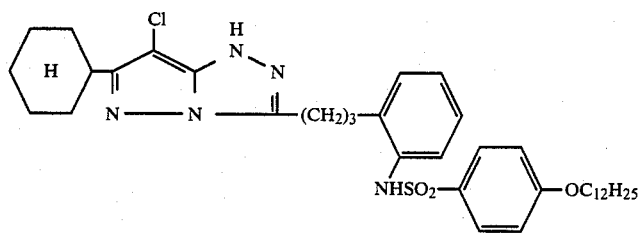 91
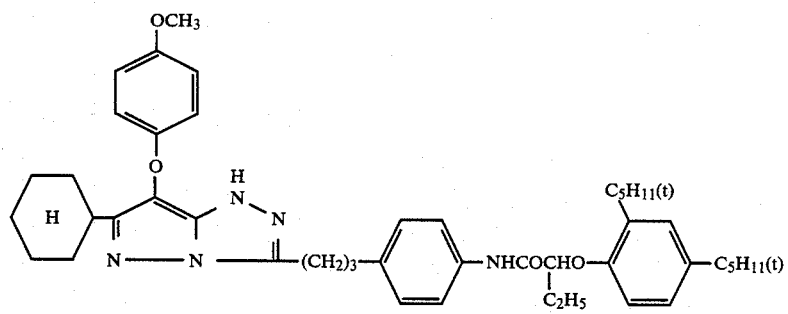 92
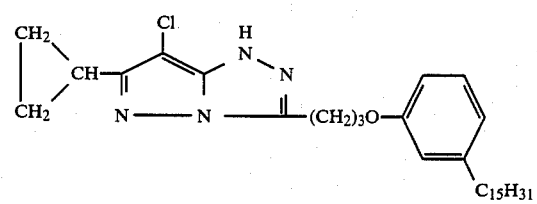 93
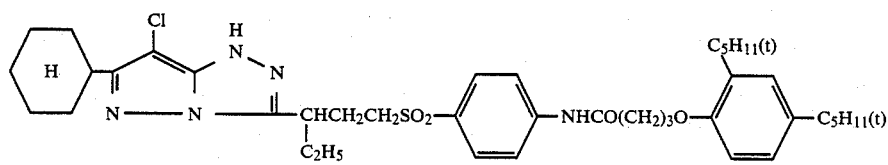 94

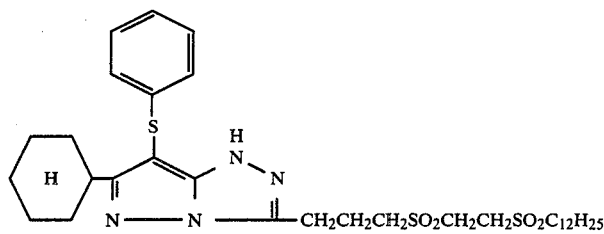
95
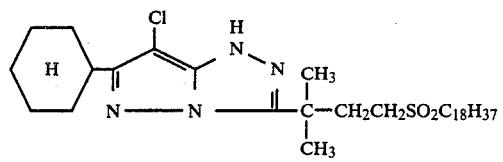
96
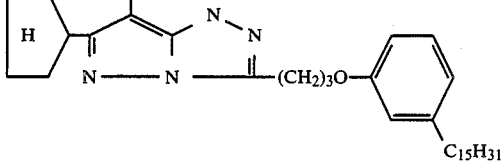
97
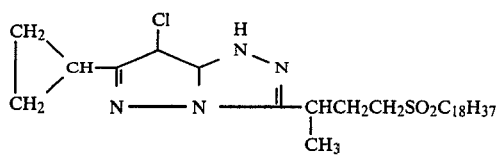
98
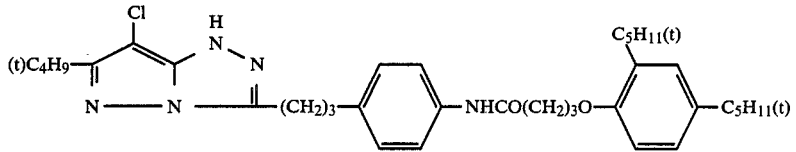
99
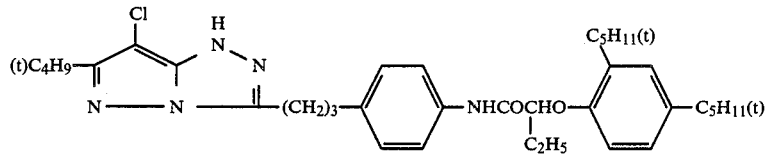
100
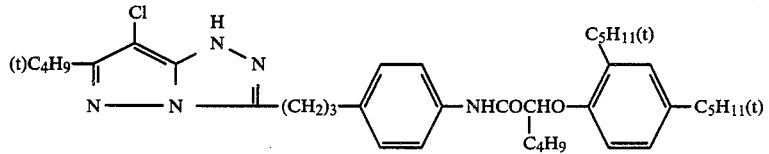
101
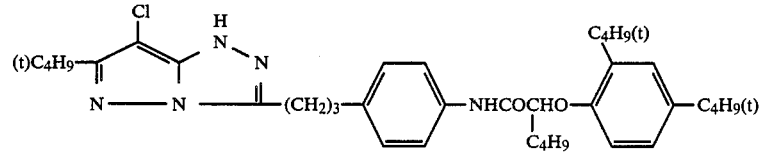
102
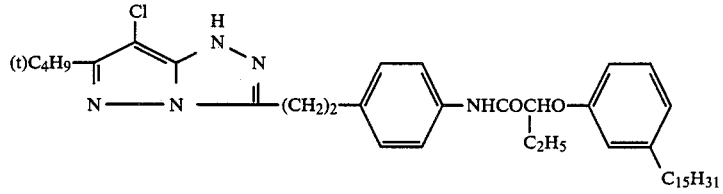
103
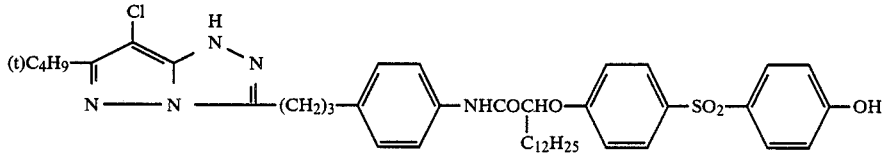
104

-continued
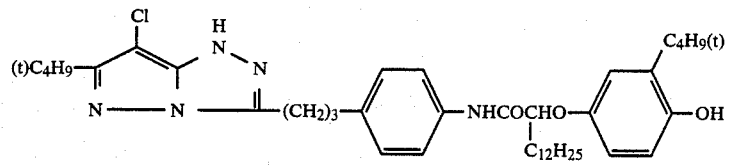
105
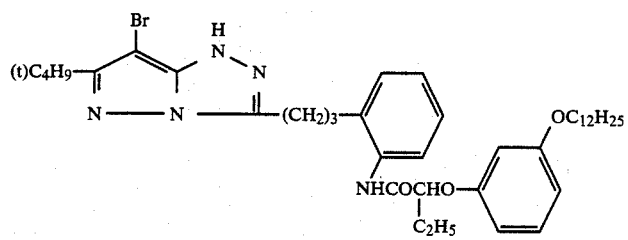
106
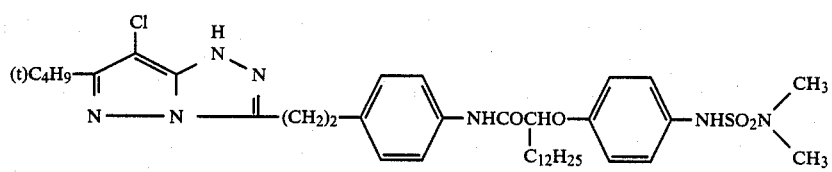
107
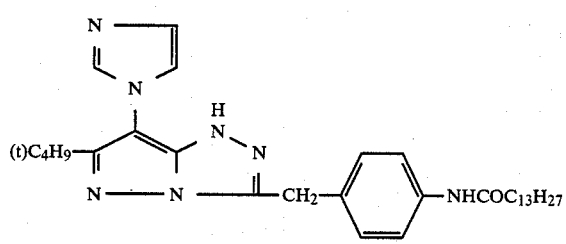
108
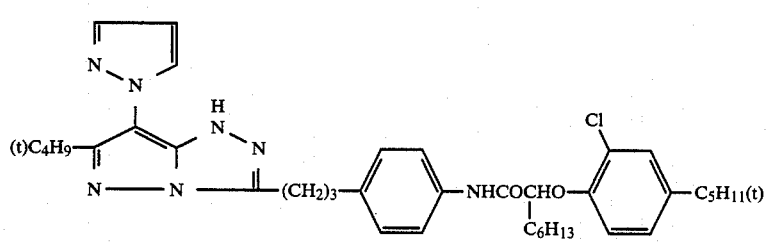
109
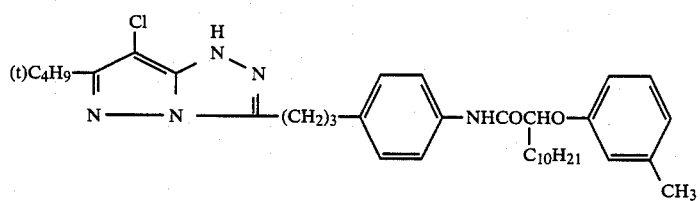
110
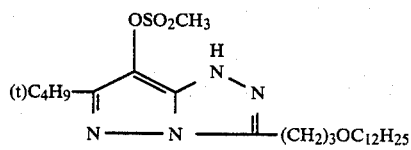
111
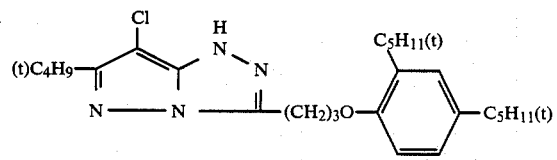
112

-continued
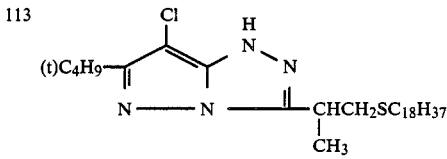
113
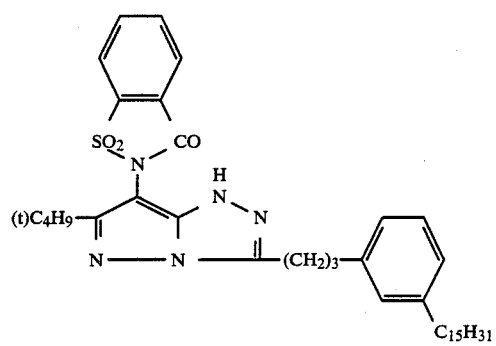
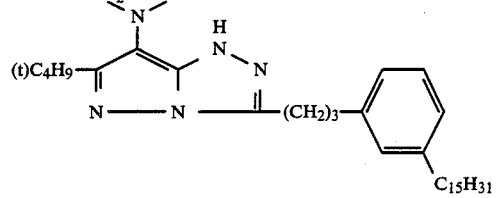
114
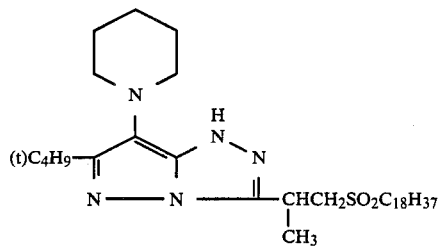
115
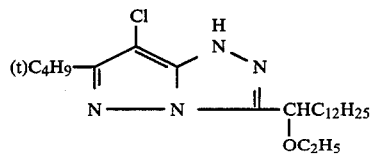
116
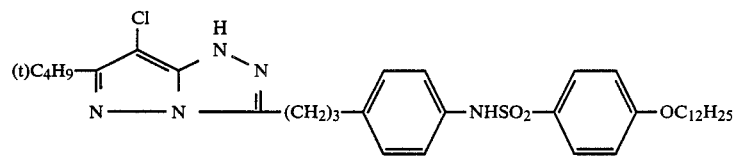
117
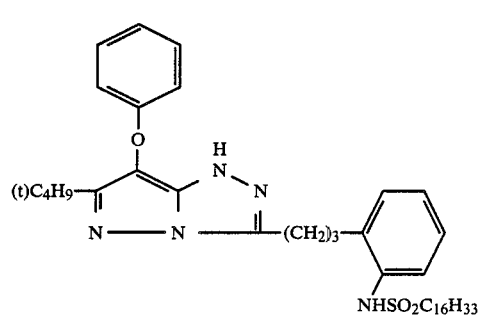
118
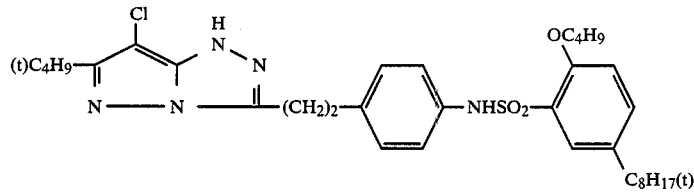
119
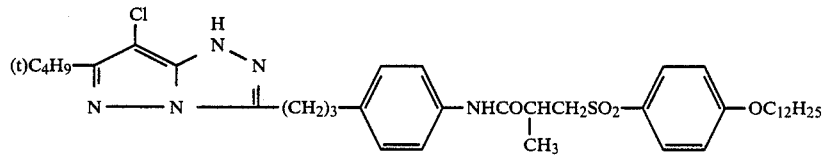
120

-continued
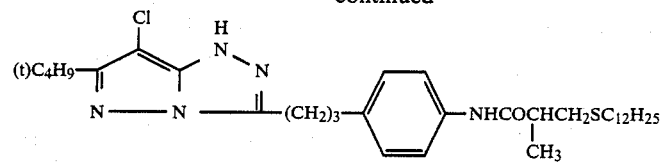
121
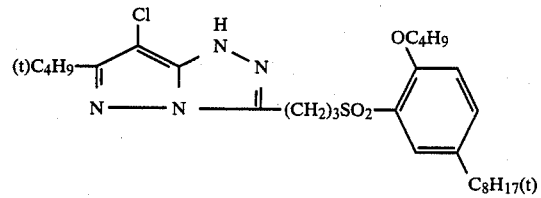
122
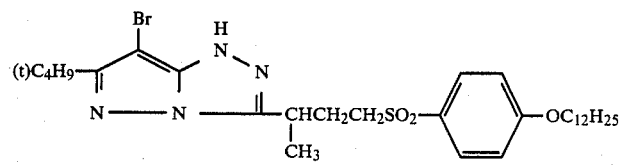
123
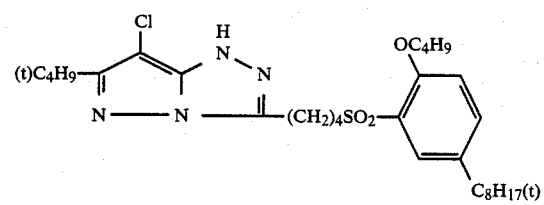
124
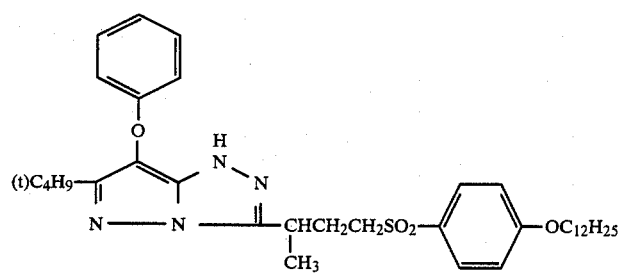
125
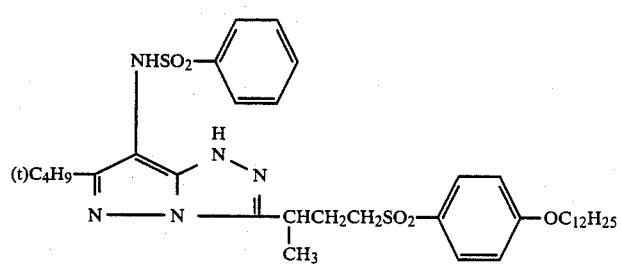
126
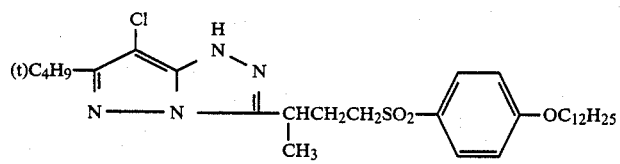
127
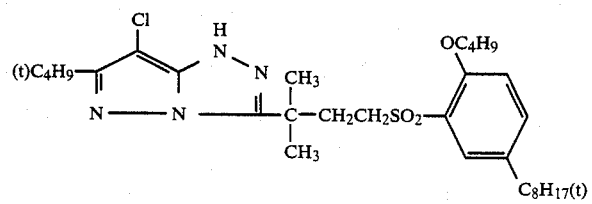
128

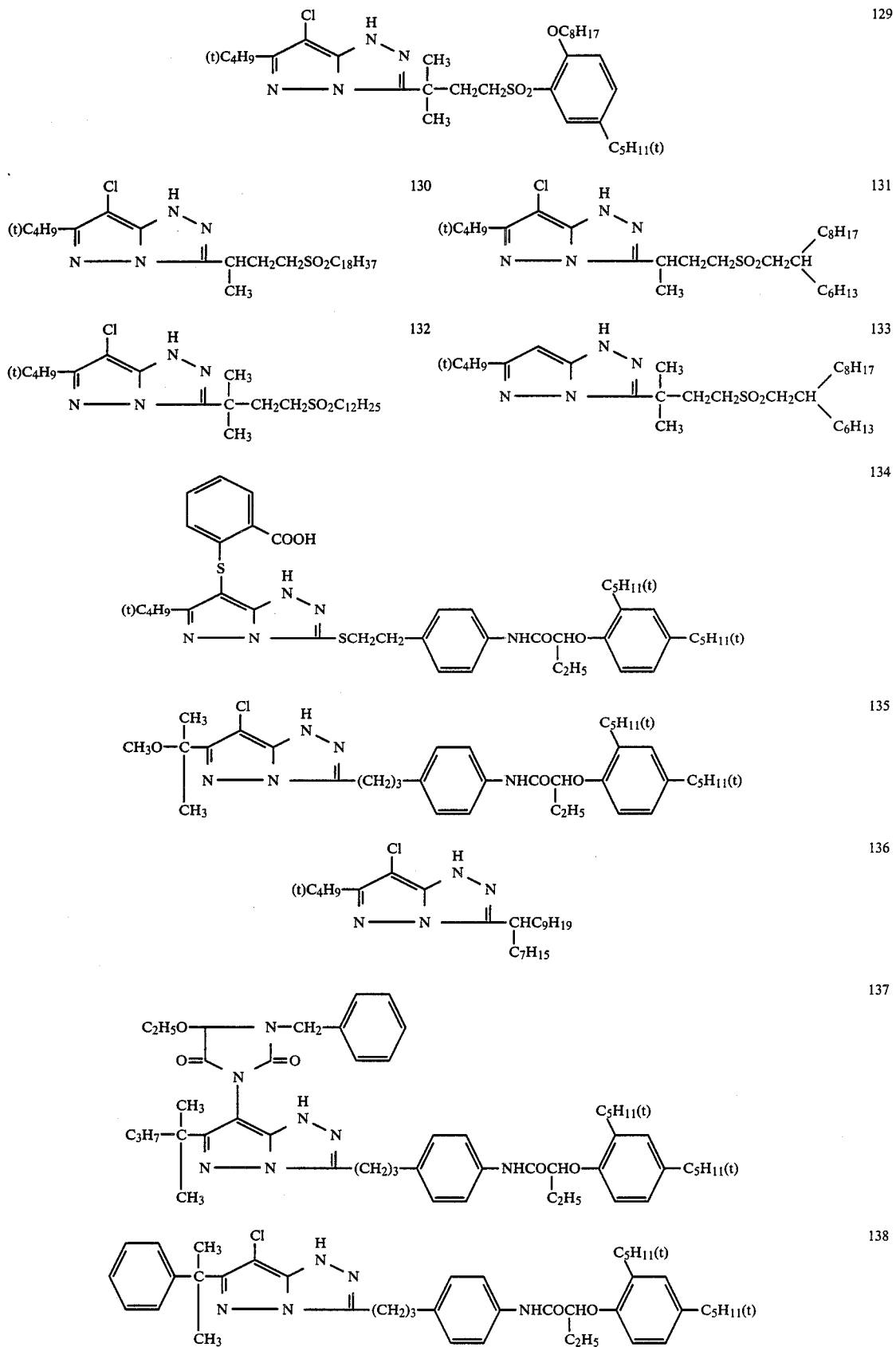

-continued
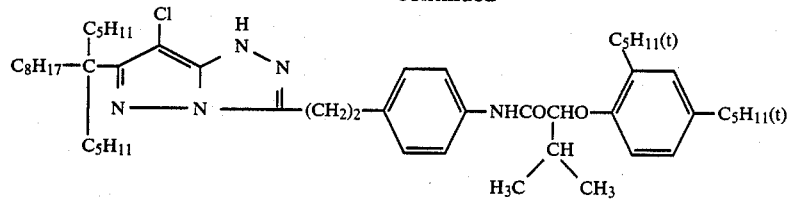
139
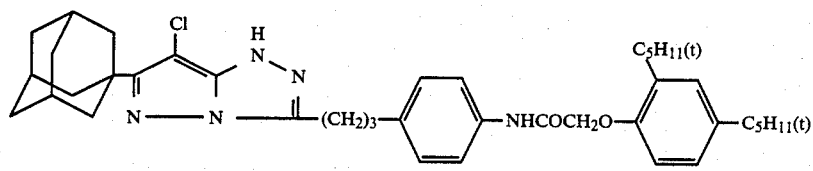
140
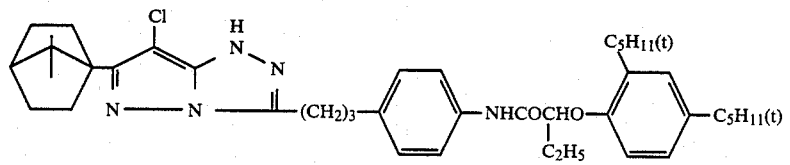
141
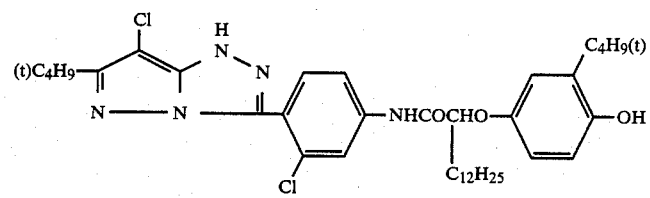
142
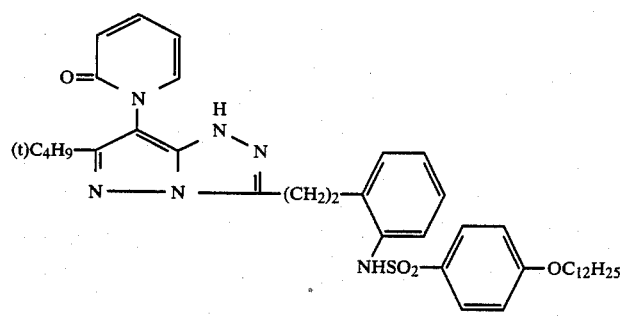
143
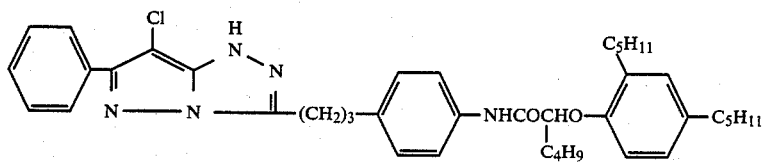
144
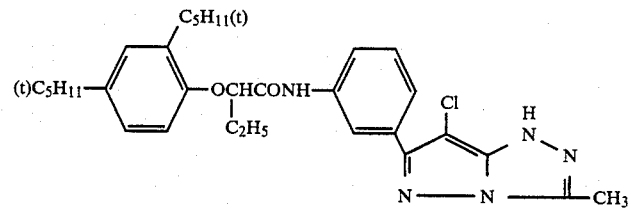
145
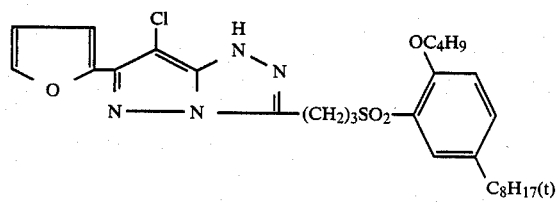
146

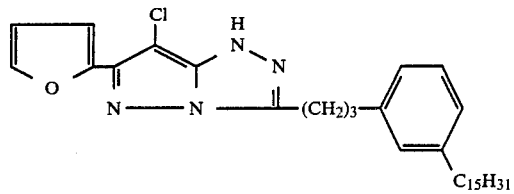
147
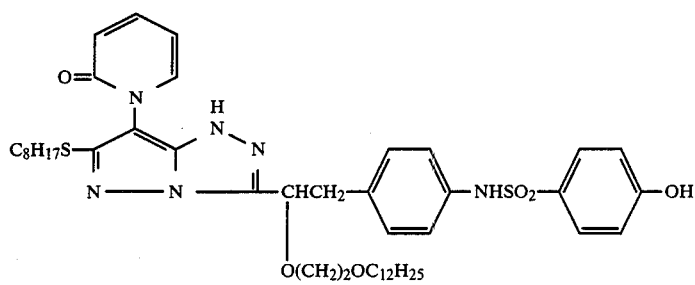
148
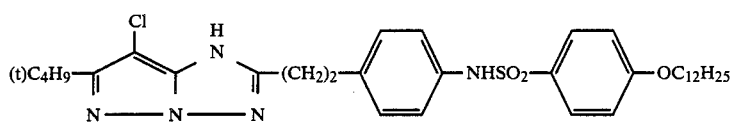
149
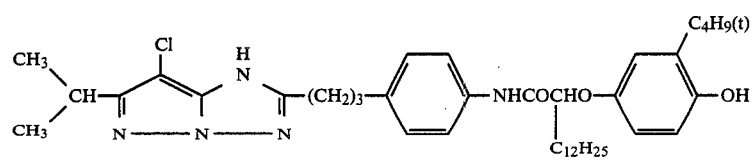
150
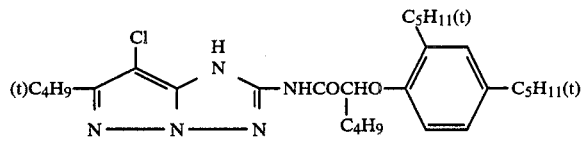
151
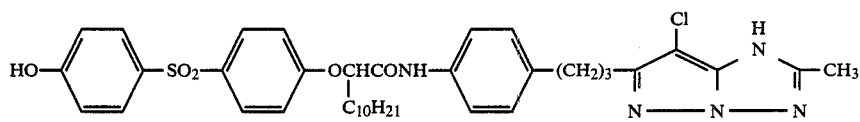
152
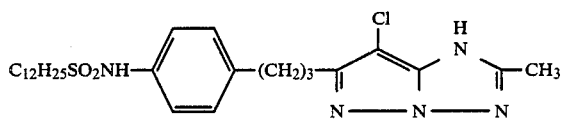
153
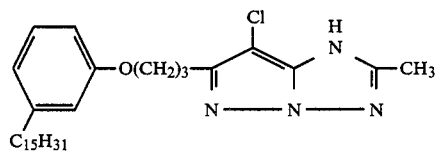
154
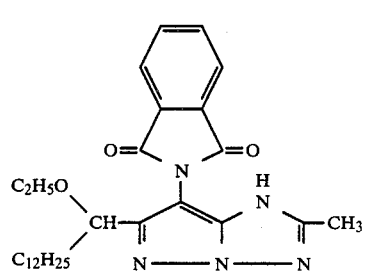
155
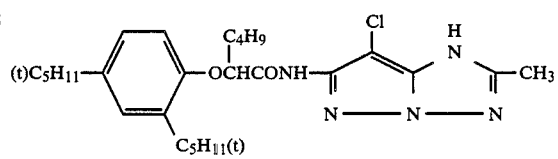
156

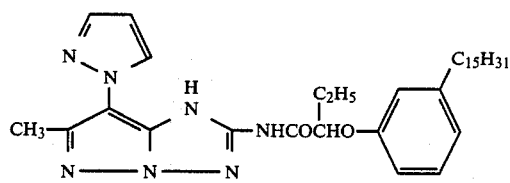
157
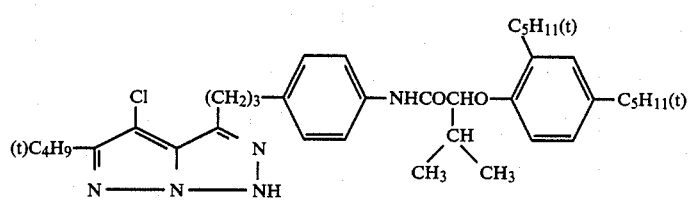
158
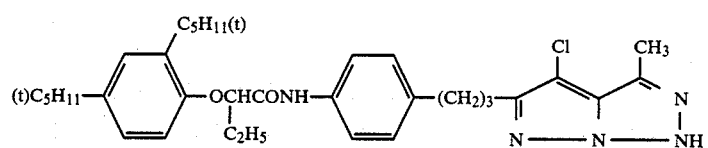
159
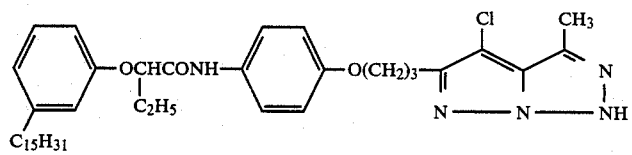
160
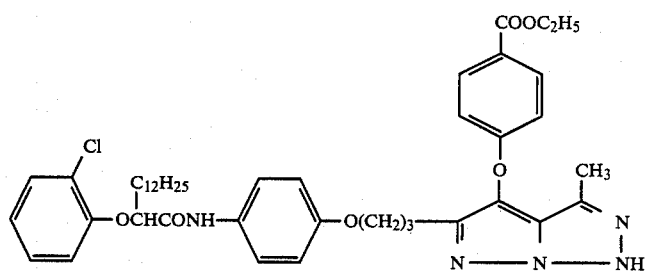
161
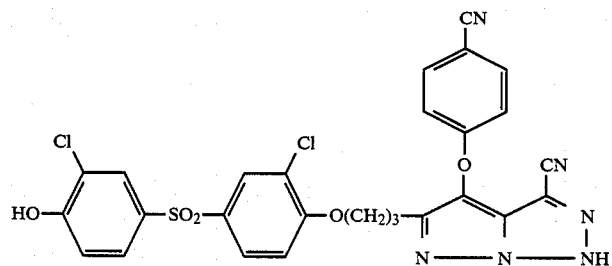
162
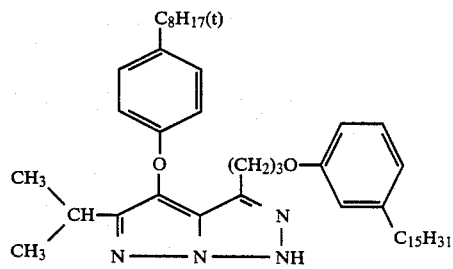
163

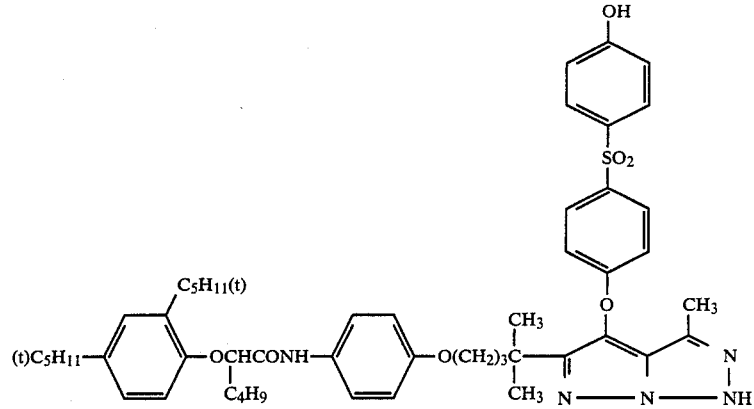
164
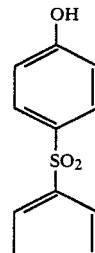
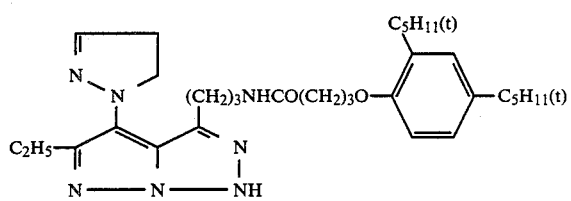
165
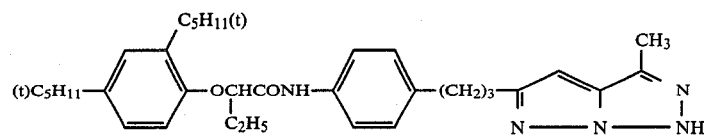
166
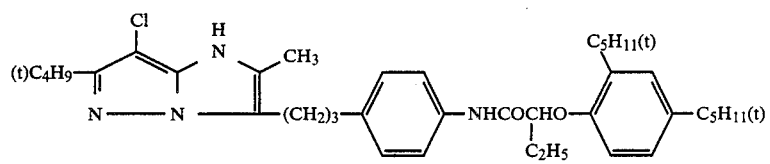
167
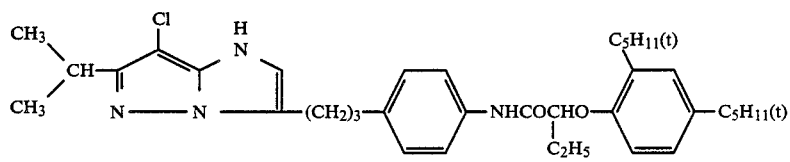
168
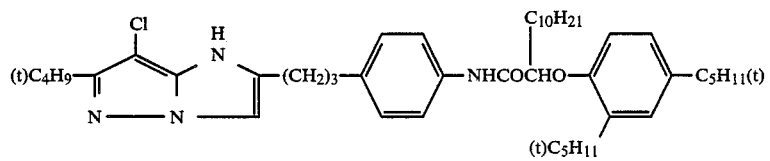
169
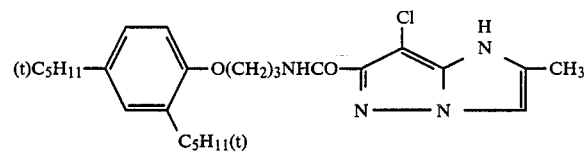
170
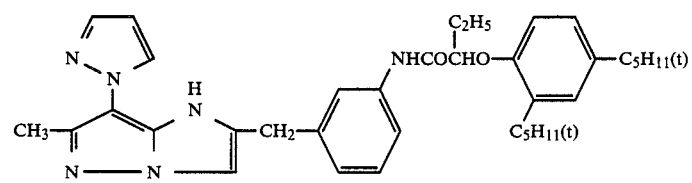
171

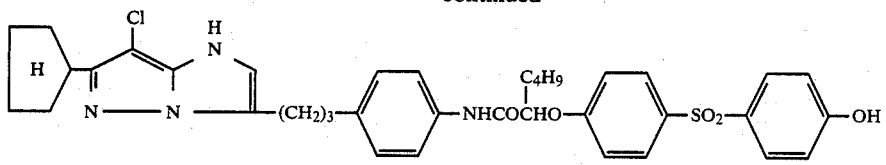
172
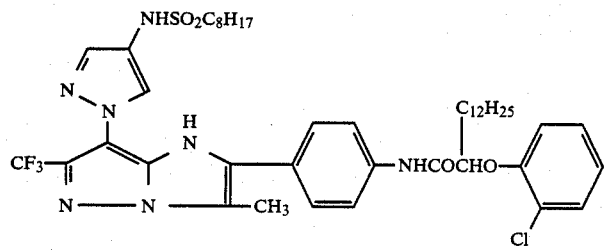
173
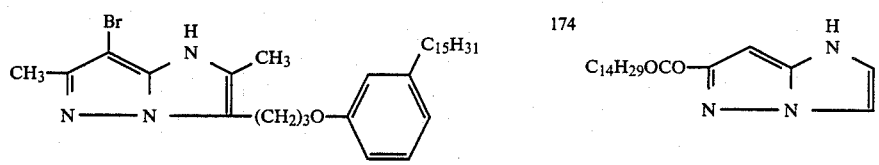
174 175
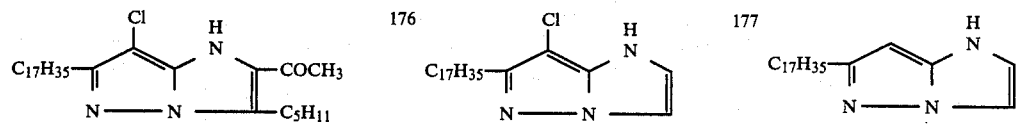
176 177 178
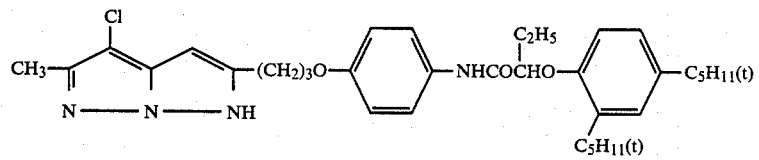
179
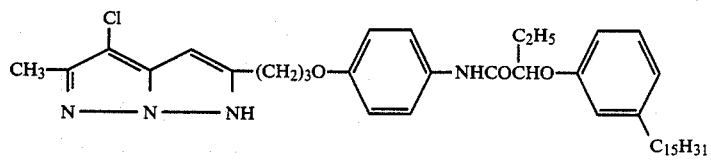
180
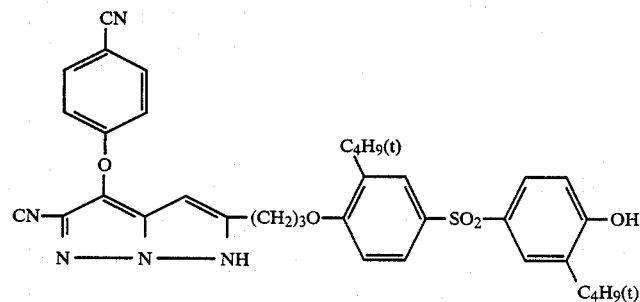
181
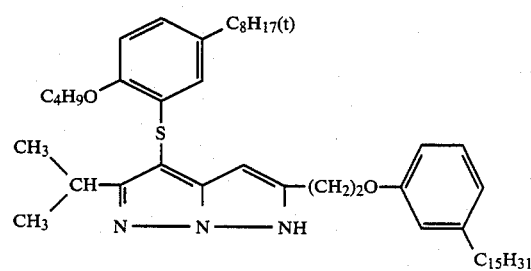
182

-continued
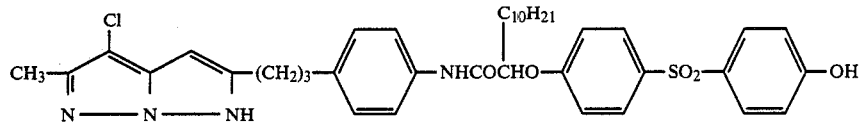
183
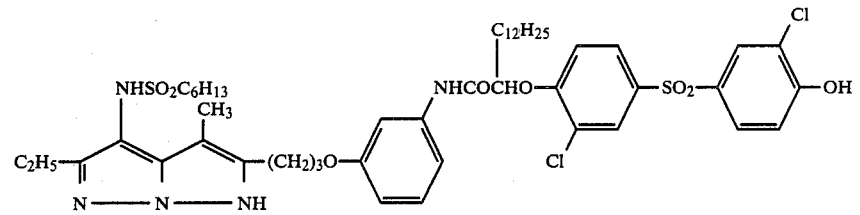
184
185
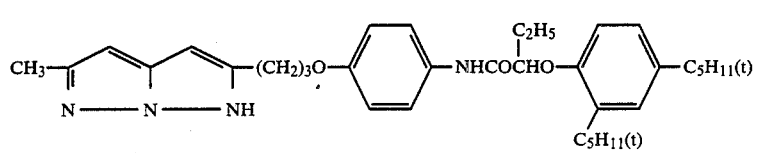
186
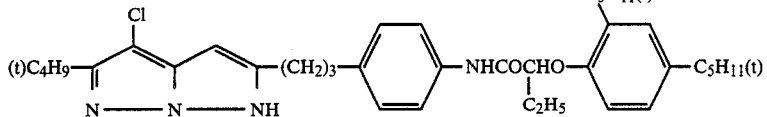
187
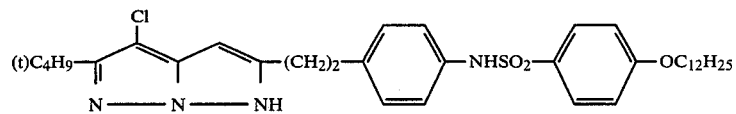
188
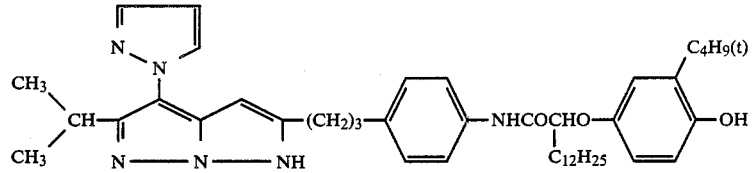
189
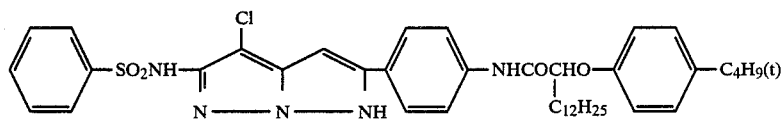
190
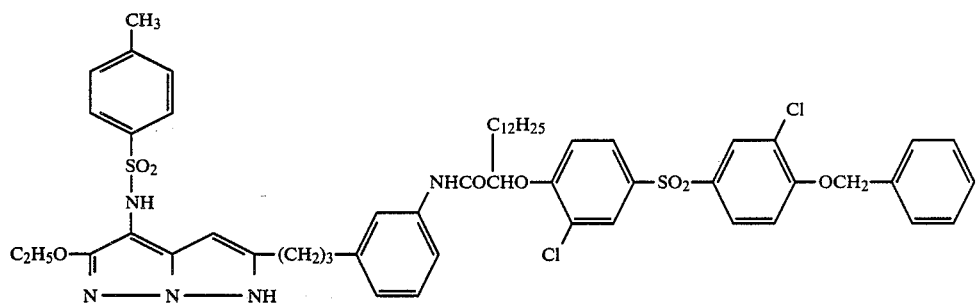
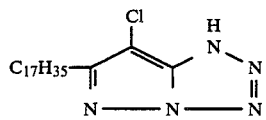
191
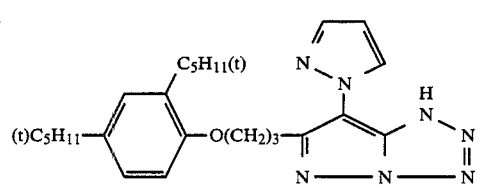
192

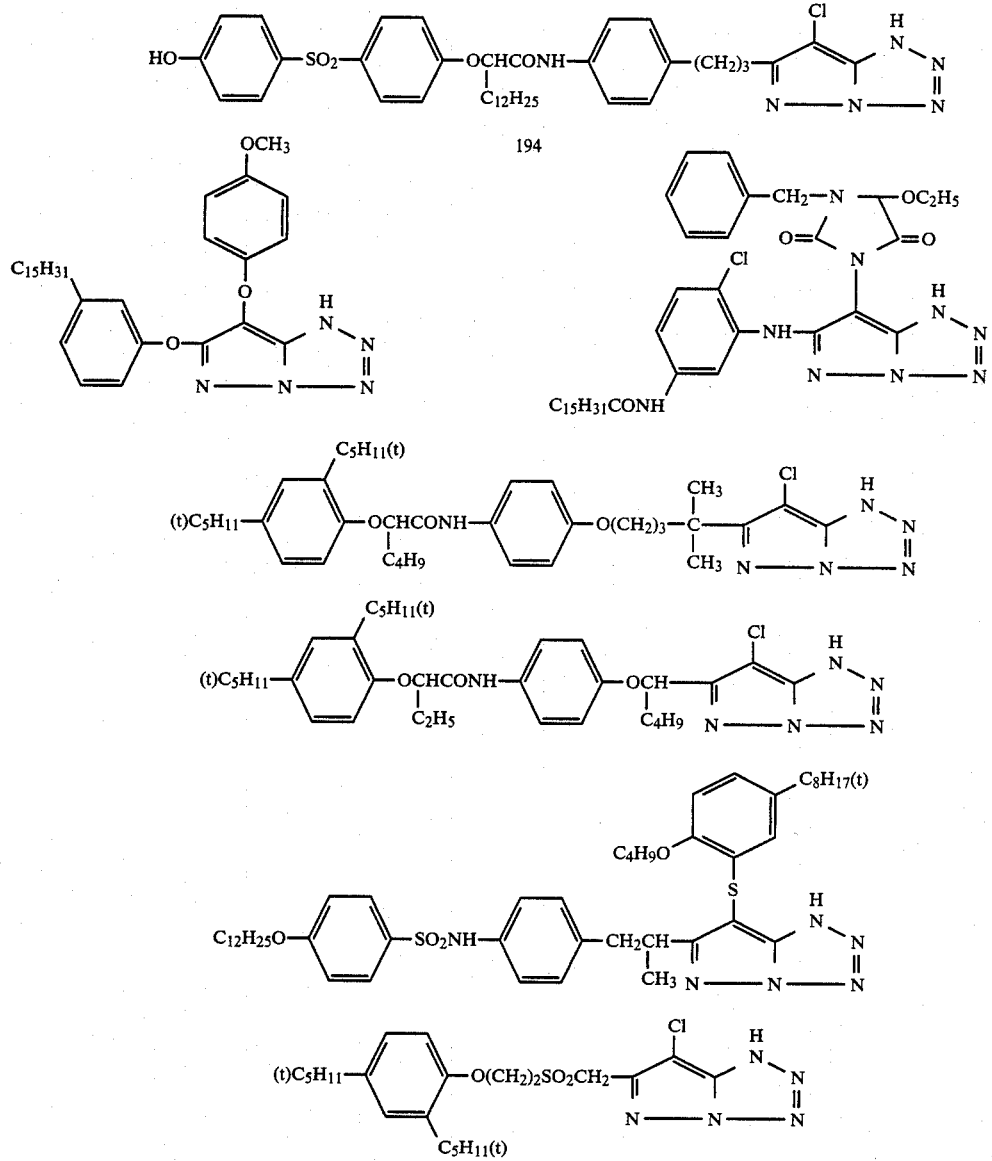

Furthermore, the synthesis of the typical couplers mentioned above was made in the light of Journal of The Chemical Society, Perkin I (1977), 2047~2052, U.S. Pat. No. 3,725,067, Japanese Patent O.P.I. Publication No. 99437/1984 and No. 42045/1983, and so forth.

The couplers of the present invention can be employed within the range of ordinarily $1 \times 10^{-3}$ mol to one mol and preferably $1 \times 10^{-2}$ mol to $8 \times 10^{-1}$ mol, per mol of silver halide.

Moreover, the couplers relating to the present invention can be used also together with magenta couplers of other types, for exmaple, such the coupler as represented by the general formula [XIV].

General formula [XIV]

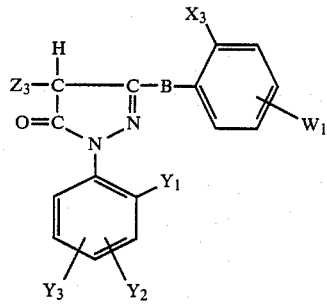

[In this formula, $X_3$ expresses a hydrogen atom, a halogen atom, an alkyl group, an alkoxy group, an aryloxy group, an amido group, a hydroxy group, an amino group, or a nitro group.

$Y_1$, $Y_2$, and $Y_3$ respectively express a hydrogen atom, a halogen atom, an alkyl group, an alkoxy group, a carboxy group, an alkoxycarbonyl group, a nitro group, an aryloxy group, a cyano group, or an acylamino group.

$W_1$ expresses a hydrogen atom, a halogen atom, or a univalent organic group.

$Z_3$ expresses an atom or a group which releases through coupling.

B expresses —NH—, —NHCO— or —NHCONH—.]

To give a more detailed explanation with regard to the general formula [XIV] mentioned above, $W_1$, which expresses a hydrogen atom, a halogen atom, or a univalent organic group, may, as a univalent organic group, also have a nitro group, an alkyl group, an alkoxy group, an arylamino group, a sulfonamide group. An alkylcarbamoyl group, an arylcarbamoyl group, an alkylsulfamoyl group, an arylsulfamoyl group, alkyl succinimide group, an alkoxycarboamide group, an alkoxycarboalkylamino group, an alkylaminocarboalkylamino group, an arylaminocarboalkylamino group, and so forth are adequate, these groups may have a substituent.

$Z_3$ may be an atom or group which releases away by any of the various couplings known to the public.

In the following part, concrete examples of the magenta couplers expressed in the general formula [XIV] are given, but the present invention are not limited to these.

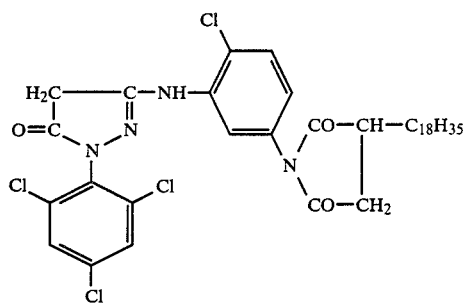

MC-1

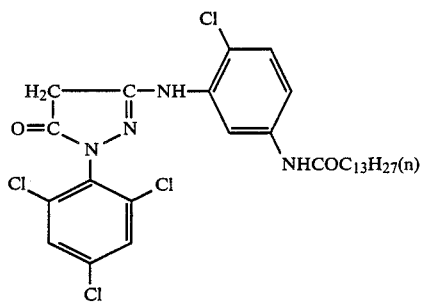

MC-2

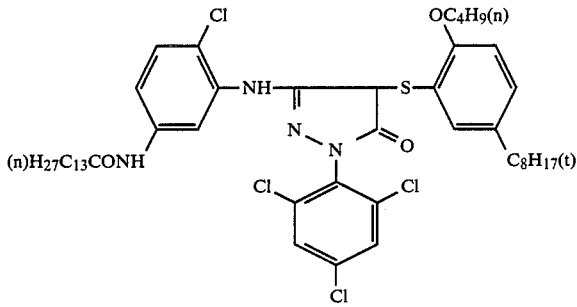

MC-3

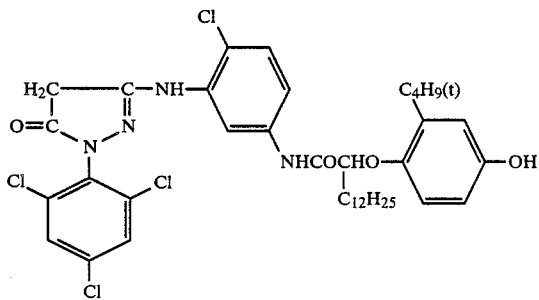

MC-4

MC-5
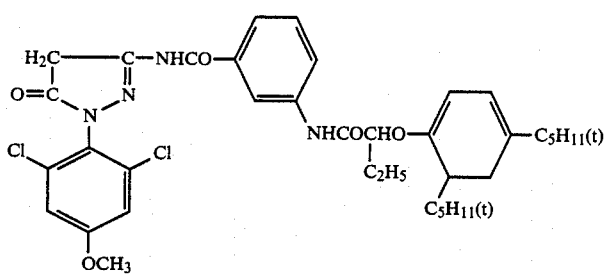
MC-6
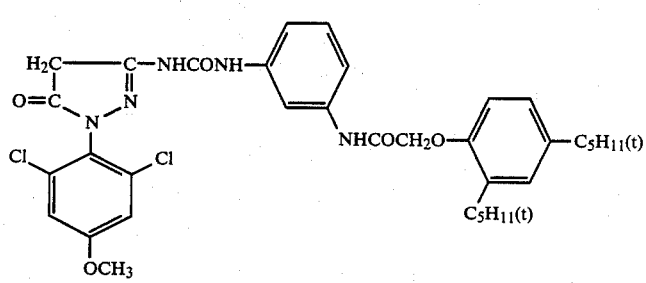
MC-7
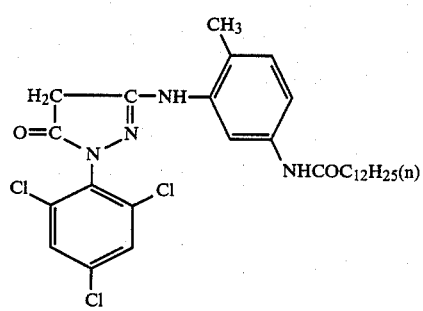
MC-8
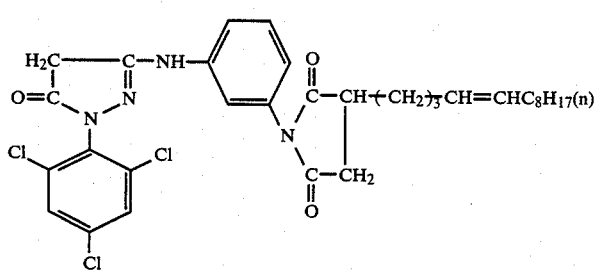
MC-9
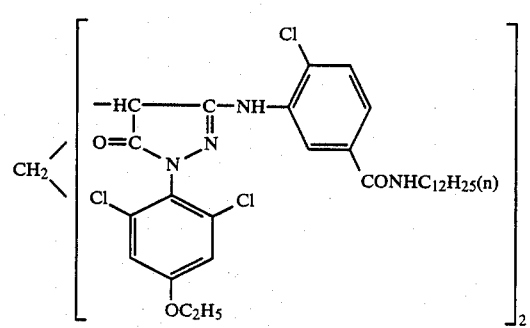

-continued

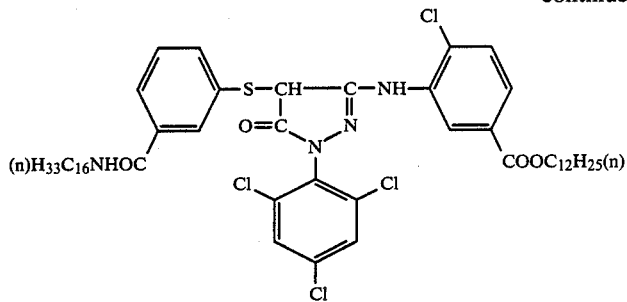
MC-10

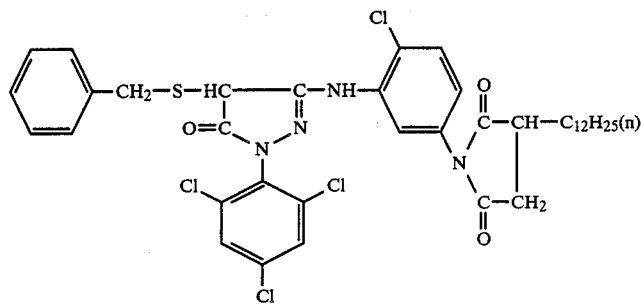
MC-11

As the cyan coupler and yellow coupler which are to be used for the present invention, phenolic or naphtholic cyan couplers and acylacetoamide or benzoylmethane yellow couplers are respectively employed.

An antioxidant may be used together with the coupler to be used for the present invention, and a description is given below with respect to the antioxidant which is preferably to be used.

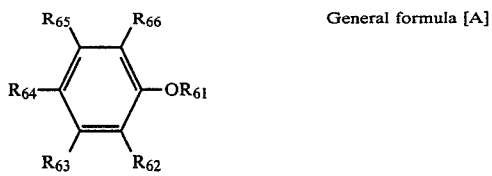
General formula [A]

In this formula, $R_{61}$ expresses a hydrogen atom, an alkyl group, an alkenyl group, an aryl group, or a heterocyclic group, and $R_{62}$, $R_{63}$, $R_{65}$, and $R_{66}$ respectively express a hydrogen atom, a halogen atom, a hydroxy group, an alkyl group, an alkenyl group, an aryl group, an alkoxy group, or an acylamino group, and $R_{64}$ expresses an alkyl group, a hydroxy group, an aryl group, or an alkoxy group.

Furthermore, $R_{61}$ and $R_{62}$ may close the ring with each other to form a five- to six-membered ring, and $R_{64}$ at such a time expresses a hydroxy group or an alkoxy group. Also, $R_{63}$ and $R_{64}$ may make a closed ring to form a five-membered hydrocarbon ring, and $R_{61}$ at such a time expresses an alkyl group, an aryl group, or a heterocyclic group. However, this does not apply to the case in which $R_{61}$ is a hydrogen atom and $R_{64}$ is a hydroxy group.

In the general formula [A] mentioned above, $R_{61}$ expresses a hydrogen atom, an alkyl group, an alkenyl group, an aryl group, or a heterocyclic group, and, of these, the alkyl groups either with a straight chain or with a branched chain, such as a methyl group, an ethyl group, a propyl group, an n-octyl group, a tertoctyl group, a hexadecyl group, for example, can be cited as the alkyl groups. As the alkenyl group, which is expressed by $R_{61}$, an ally group, a hexenyl group, an octenyl group, and so on, for example, can be cited. As the aryl group expressed by $R_{61}$, a phenyl group and a naphthyl group can be cited. As a heterocyclic group which is expressed by $R_{61}$, a tetrahydropyranyl group, a pyrimidyl group, and so forth can be specifically cited. Each of these groups may have a substituent. For example, as an alkyl group which has a substituent, a benzyl group, an ethoxymethyl group, etc. can be cited, and, as an aryl group which has a substituent, a methoxyphenyl group, a chlorphenyl group, a 4-hydroxy-3,5-dibutylphenyl, and so one can be mentioned.

In the general quation [A], $R_{62}$, $R_{63}$, $R_{65}$ and $R_{66}$ express a hydrogen atom, a halogen atom, a hydroxy group, an alkyl group, an alkenyl group, an aryl group, an alkoxy group, or an acylamino group. Of these, with respect to the alkyl group, the alkenyl group, and the aryl group, the same groups as the alkyl groups, alkenyl groups, an aryl groups cited in respect of $R_{61}$ mentioned above can be cited. Moreover, as the halogen atom mentioned above, fluorine, chlorine, bromine, etc. can be cited. Furthermore, as the above-mentioned alkoxy group, a methoxy group, an ethoxy group, and so forth can be spcifically cited. The above-mentioned acylamino group, moreover, is expressed by $R_{67}$ CONH—, in which it is possible to cite for $R_{67}$ and alkyl group (for example, such individual groups as methyl, ethyl, n-propyl, n-butyl, n-octyl, tert-octyl, benzyl groups), an alkenyl group (for example, such individual groups as allyl, octinyl, and oleyl groups), and an aryl group (for example, such individual groups as phenyl, methoxyphenyl, and naphthyl groups) or a heterocyclic group (for example, such individual groups as pyridyl and pyrimidyl groups).

In the above-mentioned general formula [A] moreover, $R_{64}$ expresses an alkyl group, an hydroxy group, an aryl group, or an alkoxy group, and, with regard to the alkyl group and the aryl group among these, the same groups as the alkyl groups and the aryl groups indicated in $R_{61}$ mentioned above can be specifically cited. Again, with regard to the alkenyl group in $R_{64}$, the same groups as the alkoxy group mentioned with respect to $R_{62}$, $R_{63}$, $R_{65}$, and $R_{66}$ mentioned above can be cited.

$R_{61}$ and $R_{62}$ together make a closed ring, and, as the rings so formed side by side with a benzene ring, chroman, coumaran, methylenedioxy benzene, and so forth, for example, can be cited.

Also, as the rings which are formed, together with a benzene ring, by the formation of a closed ring by $R_{63}$ and $R_{64}$, indan, for example, cna be cited. These rings may have substituents (for example, alkyl, alkoxy, and aryl).

Moreover, the atom is the ring which $R_{61}$ and $R_{62}$, or $R_{63}$ and $R_{64}$, from by their making of a closed ring may be used as the spiro atom to form a spiro compound, or a biscompound may be formed with $R_{62}$, $R_{64}$, etc. used as bonding groups.

Among the phenolic compounds or phenylether compounds which are expressed in the general formula [A] mentioned abvoe, the preferable one is the biindan compound, which has four RO-groups (where R expresses an alkyl group, an alkenyl group, an aryl group, or a heterocylic group), and the said compound can be specially preferably expressed in the general formula [A-1] given in the following:

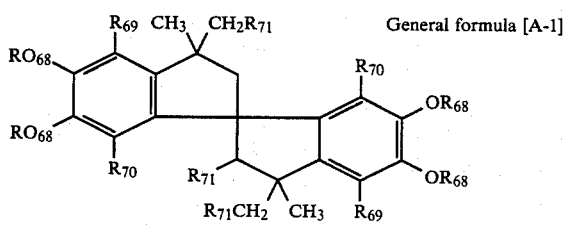

General formula [A-1]

In this formula, $R_{68}$ expresses those groups which are expressed with an alkyl group (for exmaple, methyl, ethyl, propyl, n-octyl, tert-octyl, benzyl, and hexadecyl), an alkenyl group (for example, allyl, octenyl, and oleyl), an aryl group (for example, phenyl and naphthyl), or a heterocylic group (for exmaple, tetrahydropyranyl and pyrimidyl). $R_{69}$ and $R_{70}$ respectively express a hydrogen atom, a halogen atom (for example, fluorine, chlorine, and bromine), an alkyl group (for example, methyl, ethyl, n-butyl, and benzyl), and an alkenyl group (for example, allyl, hexenyl, and octenyl), or an alkoxy group (for exmaple, methoxy, ethoxy, and benzyloxy), and $R_{71}$ expresses a hydrogen atom, an alkyl, group (for example, methyl, ethyl, n-butyl, and benzyl), an alkenyl group (for example, 2-propenyl, hexenyl, and octenyl), or an aryl group (for example, phenyl, methoxyphenyl, chlorphenyl, and nathphyl).

The compounds which are expressed by the general formula [A] mentioned above also include those compound which are described in U.S. Pat. No. 3,935,016, No. 3,982,944, and No. 4,254,216, Japanese Patent O.P.I. Publication No. 21004/1980 and 145530/1979, British Patent Disclosures No. 2,077,455 and No. 2,062,855, U.S. Pat. No. 3,764,337, No. 3,432,300, No. 3,574,627, and No. 3,573,050, Japanese Patent O.P.I. Publication No. 15225/1977, No. 20327/1978, No. 17729/1978, and No. 6321/1980, British Pat. No. 1,347,556, British Patent Disclosure No. 2,066,975, Japanese Patent Examined Publications No. 12337/1979 and No. 31625/1973, U.S. Pat. No. 3,700,455, and so forth.

The amount used of the compound expressed by the above-mentioned general formula [A] is preferably 5~300 mol %, and more preferably 10~200 mol %, for magenta coupler.

In the following part are shown representative concrete examples of the compounds which are expressed by the general formula [A] given above:

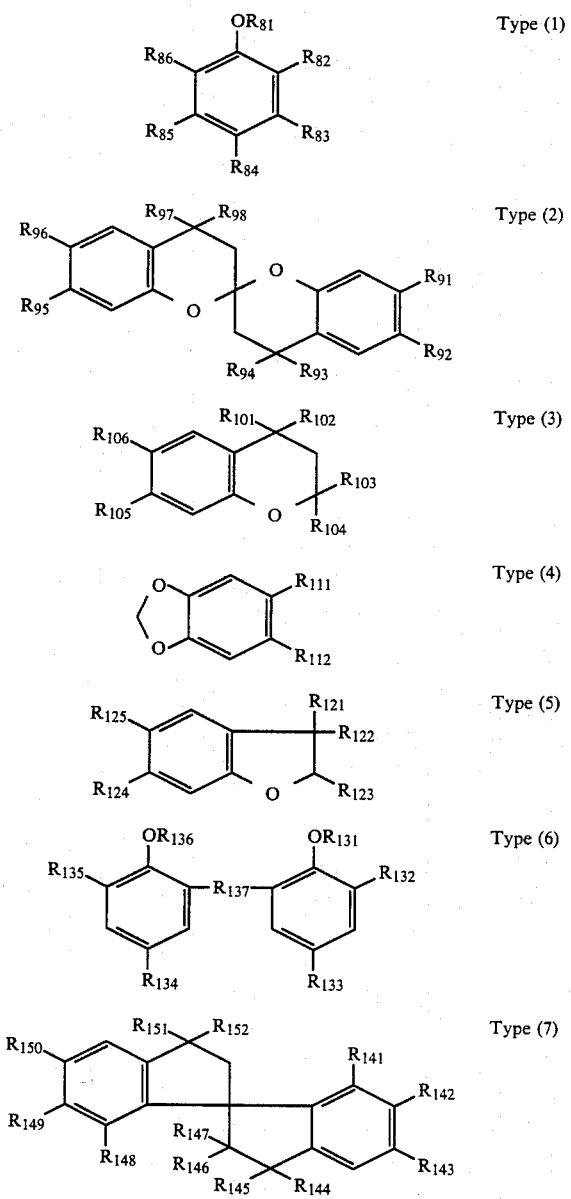

| Compound No. | $R_{81}$ | $R_{82}$ | $R_{83}$ | $R_{84}$ | $R_{85}$ | $R_{86}$ |
|---|---|---|---|---|---|---|
| A-1 | H | OH | —C(CH3)2CH2C(CH3)3 | CH3O | H | —C(CH3)2CH2C(CH3)3 |
| A-8 | C8H17 | C(CH3)2C2H5 | H | C8H17O | C(CH3)2C2H5 | H |
| A-14 | H | H | OH | C(CH3)2CH2C(CH3)3 | H | H |

-continued

Type (1)

| Compound No. | $R_{81}$ | $R_{82}$ | $R_{83}$ | $R_{84}$ | $R_{85}$ | $R_{86}$ |
|---|---|---|---|---|---|---|
| A-16 | H | $C(CH_3)_2C_3H_7$ | H | $CH_3O$ | $C(CH_3)_2C_3H_7$ | H |

Type (2)

| Compound No. | $R_{91}$ | $R_{92}$ | $R_{93}$ | $R_{94}$ | $R_{95}$ | $R_{96}$ | $R_{97}$ | $R_{98}$ |
|---|---|---|---|---|---|---|---|---|
| A-2 | $CH_3$ | OH | $CH_3$ | $CH_3$ | $CH_3$ | OH | $CH_3$ | $CH_3$ |
| A-10 | $CH_3$ | $OCH_3$ | $CH_3$ | $CH_3$ | $CH_3$ | $CH_3O$ | $CH_3$ | $CH_3$ |

Type (5)

| Compound No. | $R_{121}$ | $R_{122}$ | $R_{123}$ | $R_{124}$ | $R_{125}$ |
|---|---|---|---|---|---|
| A-5 | $CH_3$ | $CH_3$ | $C_2H_5O$ | $(t)C_8H_{17}$ | OH |

Type (3)

| Compound No. | $R_{101}$ | $R_{102}$ | $R_{103}$ | $R_{104}$ | $R_{105}$ | $R_{106}$ |
|---|---|---|---|---|---|---|
| A-3 | $CH_3$ | $CH_3$ | H | $CH_3$ | $(t)C_8H_{17}$ | OH |
| A-11 | $CH_3$ | $CH_3$ | H | $CH_3$ | $(t)C_8H_{17}$ | $C_8H_{17}O$ |
| A-12 | $CH_3$ | $CH_3$ | H | $CH_3$ | $CH_3$ | $O(CH_2)_2OC_{10}H_{21}$ |
| A-17 | H | $CH_3$ | $CH_3$ | $CH_3$ | $(t)C_8H_{17}$ | OH |
| A-18 | $CH_3$ | $CH_3$ | $CH_3$ | (see structure) | $CH_3$ | OH |

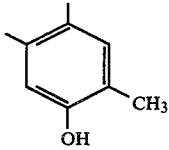

Type (4)

| Compound No. | $R_{111}$ | $R_{112}$ |
|---|---|---|
| A-4 | $C_3H_7$ | $-CH_2O(CH_2)_2OCH_2-$ (3,4-methylenedioxyphenyl with $C_3H_7$) |
| A-9 | $C_3H_7$ | $-CH_2O(CH_2)_2OC_4H_9$ |

Type (6)

| Compound No. | $R_{131}$ | $R_{132}$ | $R_{133}$ | $R_{134}$ | $R_{135}$ | $R_{136}$ | $R_{137}$ |
|---|---|---|---|---|---|---|---|
| A-6 | H | $(t)C_4H_9$ | $CH_3$ | $CH_3$ | $(t)C_4H_9$ | H | $CH_2$ |
| A-15 | $CH_3$ | $(t)C_4H_9$ | $CH_3$ | $CH_3$ | $(t)C_4H_9$ | $CH_3$ | $CH_2$ |

Type (7)

| Compound No. | $R_{141}$ | $R_{142}$ | $R_{143}$ | $R_{144}$ | $R_{145}$ | $R_{146}$ |
|---|---|---|---|---|---|---|
| A-13 | H | $C_3H_7O$ | $C_3H_7O$ | $CH_3$ | $CH_3$ | H |
| A-19 | H | $CH_3O$ | $CH_3O$ | $CH_3$ | $CH_3$ | H |
| A-20 | $CH_3$ | $C_4H_9O$ | $C_4H_9O$ | $CH_3$ | $CH_3$ | H |
| A-21 | H | $C_2H_5O$ | $C_2H_5O$ | $CH_3$ | $CH_3$ | H |
| A-22 | H | $CH_3O$ | $CH_3O$ | $C_2H_5$ | $CH_3$ | H |
| A-23 | H | $C_7H_{15}COO$ | $C_7H_{15}COO$ | $CH_3$ | $CH_3$ | H |
| A-24 | H | $C_4H_9O$ | $C_4H_9O$ | $CH_3$ | $CH_3$ | H |
| A-25 | H | $CH_3O(CH_2)_2O$ | $CH_3O(CH_2)_2O$ | $CH_3$ | $CH_3$ | H |
| A-26 | H | $CH_2=CHCH_2O$ | $CH_2=CHCH_2O$ | $CH_3$ | $CH_3$ | H |
| A-27 | H | $C_3H_7O$ | $C_3H_7O$ | $C_6H_5CH_2$ | $CH_3$ | $C_6H_5$ |
| A-28 | $CH_3O$ | $C_4H_9O$ | $C_4H_9O$ | $CH_3$ | $CH_3$ | H |
| A-29 | H | $(s)C_5H_{11}O$ | $(s)C_5H_{11}O$ | $CH_3$ | $CH_3$ | H |
| A-30 | H | $C_4H_9O$ | $C_4H_9O$ | $(i)C_3H_7$ | $CH_3$ | $CH_3$ |
| A-31 | H | $C_{18}H_{37}O$ | $C_{18}H_{27}O$ | $CH_3$ | $CH_3$ | H |
| A-32 | H | $C_6H_5CH_2O$ | $C_6H_5CH_2O$ | $CH_3$ | $CH_3$ | H |

| Compound No. | $R_{147}$ | $R_{148}$ | $R_{149}$ | $R_{150}$ | $R_{151}$ | $R_{152}$ |
|---|---|---|---|---|---|---|
| A-13 | H | H | $C_3H_7O$ | $C_3H_7O$ | $CH_3$ | $CH_3$ |
| A-19 | H | H | $CH_3O$ | $CH_3O$ | $CH_3$ | $CH_3$ |
| A-20 | H | $CH_3$ | $C_4H_9O$ | $C_4H_9O$ | $CH_3$ | $CH_3$ |
| A-21 | H | H | $C_2H_5O$ | $C_2H_5O$ | $CH_3$ | $CH_3$ |
| A-22 | $CH_3$ | H | $CH_3O$ | $CH_3O$ | $CH_3$ | $C_2H_5$ |
| A-23 | H | H | $C_7H_{15}COO$ | $C_7H_{15}COO$ | $CH_3$ | $CH_3$ |
| A-24 | H | H | $C_4H_9O$ | $C_4H_9O$ | $CH_3$ | $CH_3$ |

-continued

Type (7)

| | | | | | | |
|---|---|---|---|---|---|---|
| A-25 | H | H | $CH_3O(CH_2)_2O$ | $CH_3O(CH_2)_2O$ | $CH_3$ | $CH_3$ |
| A-26 | H | H | $CH_2=CHCH_2O$ | $CH_2=CHCH_2O$ | $CH_3$ | $CH_3$ |
| A-27 | H | H | $C_3H_7O$ | $C_3H_7O$ | $C_6H_5O$ | $CH_3$ |
| A-28 | H | $CH_3$ | $C_4H_9O$ | $C_4H_9O$ | $CH_3$ | $CH_3$ |
| A-29 | H | H | $(s)C_5H_{11}O$ | $(s)C_5H_{11}O$ | $CH_3$ | $CH_3$ |
| A-30 | $CH_3$ | H | $C_4H_9O$ | $C_4H_9O$ | $(i)C_3H_7$ | $CH_3$ |
| A-31 | H | H | $C_{18}H_{37}O$ | $C_{18}H_{37}O$ | $CH_3$ | $CH_3$ |
| A-32 | H | H | $C_6H_5CH_2O$ | $C_6H_5CH_2O$ | $CH_3$ | $CH_3$ |

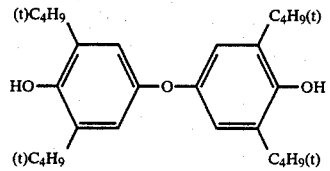

General formula [B]

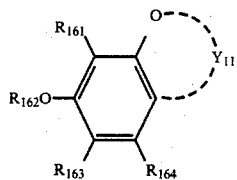

(In this formula, $R_{161}$ and $R_{164}$ respectively express a hydrogen atom, a halogen atom, an alkyl group, an alkenyl gruop, an alkoxy group, an alkenyloxy group, a hydroxy group, an aryl group, an aryloxy group, an acyl group, an acylamino group, an acyloxy group, a sulfonamido group, a cyloalkyl, or an alkoxycarbonyl group, and $R_{162}$ expresses a hydrogen atom, an alkyl group, an alkenyl group, an aryl group, an acyl group, a cycloalkyl group, or a heterocyclic group, and $R_{163}$ expresses a hydrogen atom, a halogen atom, an alkyl group, an alkenyl group, an aryl group, an aryloxy group, an acyl group, an acyloxy group, a sulfonamido group, a cycloalkyl group, or an alkoxycarbonyl group.

The groups mentioned above may respectively be substituted with other substituents, for which an alkyl group, an alkenyl group, an alkoxy group, an aryl group, an aryloxy group, a hydroxy group, an alkoxycarbonyl group, an allyloxycarbonyl group, an acylamino group, an acyloxy group, a carbamoyl group, a sulfonamido group, a sulfamoyl group, and so forth can be cited as examples.

Moreover, $R_{162}$ and $R_{163}$ may together form a closed ring, to form a five- to six-membered ring. As the rings which are formed together with a benzene ring, by $R_{162}$ and $R_{163}$ through their formation of a closed ring, a chroman ring and a methyenedioxybenzene ring, for exmaple, can be mentioned.

$Y_{11}$ expresses a group of atoms necessary for the formation of a chroman or coumaran ring.

The chroman or coumaran ring may be substituted with an halogen atom, an alkyl group, a cycloalkyl group, an alkoxy group, an alkenyl group, an alkenyloxy group, a hydroxy group, an aryl group, an aryloxy group, or a heterocycle, and may, moreover form a spiro ring.

Among the compounds expressed in the general formula [B], the compounds which are specially useful for the present invention are included in those compounds which are indicated in the general formulae [B-1], [B-2], [B-3], [B-4], and [B-5].

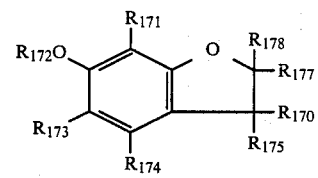

General formula [B-1]

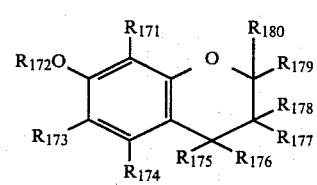

General formula [B-2]

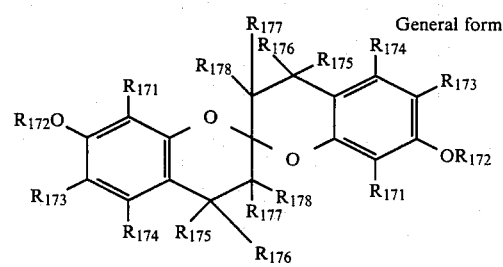

General formula [B-3]

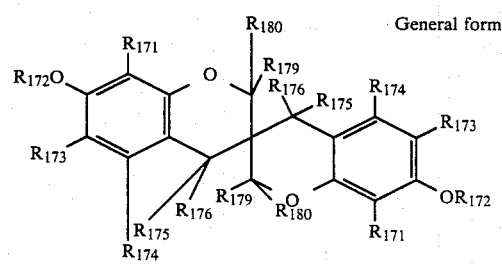

General formula [B-4]

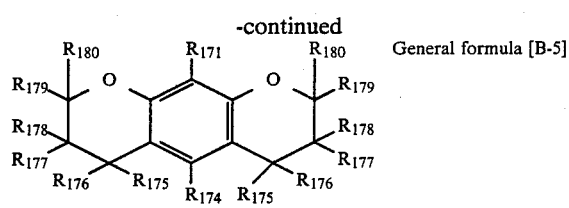

General formula [B-5]

$R_{171}$, $R_{172}$, $R_{173}$, and $R_{174}$ in the general formulae [B-1], [B-2], [B-3], [B-4], and [B-5], have the same meaing as that in the general formula [B] given above, and $R_{175}$, $R_{176}$, $R_{177}$, $R_{178}$, $R_{179}$, and $R_{180}$ express a hydrogen atom, a halogen atom, an alkyl group, an alkoxy group, a hydroxy group, an alkenyl group, an alkenyloxy group, an aryl group, an aryloxy group, or a heterocyclic group.

Furthermore, $R_{175}$ and $R_{176}$, $R_{176}$ and $R_{177}$, $R_{177}$ and $R_{178}$, $R_{178}$ and $R_{179}$, and $R_{179}$ and $R_{180}$ may develop a ring with each other, thereby forming a carbon ring, and the carbon ring, moreover, may be substituted with an alkyl group.

Specially useful are those compounds which have a hydrogen atom, an alkyl group, an alkoxy group, a hydroxy group, or a cycloalkyl group for $R_{171}$ and $R_{174}$ and a hydrogen atom, an alkyl group, or a cycloalkyl group for $R_{175}$, $R_{176}$, $R_{177}$, $R_{178}$, $R_{179}$, and $R_{180}$ in the general formulae [B-1], [B-2], [B-3], [B-4], and [B-5] given above.

The compounds which are expressed in the general formula [B] represent and include those compounds which are described in Tetradhedron, 1970, vol. 26, pp. 4743~4751, The Journal of the Japan Chemical Society, 1972, No. 10, pp. 0987~1990, Chemical (chem. lett.) 1972 (4), pp. 315~316, and Japanese Patent Disclosure No. 139383-Showa 55 (1980), and the compounds can be synthesized in accordance with the process which is described in these.

Of the compounds expressed by the general formula [B] mentioned above, the amount used is preferably 5~300 mol %, and more preferably 10~200 mol %, for the magenta coupler relevant to the present invention as mentined above.

In the following part, representative specific examples for these compounds are presented.

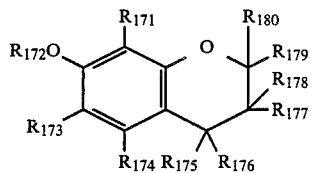

| Compound No. | $R_{171}$ | $R_{172}$ | $R_{173}$ | $R_{174}$ | $R_{175}$ | $R_{176}$ | $R_{177}$ | $R_{178}$ | $R_{179}$ | $R_{180}$ |
|---|---|---|---|---|---|---|---|---|---|---|
| B-1 | H | H | H | H | H | $CH_3$ | H | H | $CH_3$ | $CH_3$ |
| B-2 | H | H | $CH_3$ | H | H | $CH_3$ | H | H | $CH_3$ | $CH_3$ |
| B-3 | H | H | $C_{12}H_{25}$ | H | H | $CH_3$ | H | H | $CH_3$ | $CH_3$ |
| B-4 | H | H | ⬠H | H | H | $CH_3$ | H | H | $CH_3$ | $CH_3$ |
| B-5 | H | $CH_3$ | H | H | H | $CH_3$ | H | H | $CH_3$ | $CH_3$ |
| B-9 | $CH_3$ | H | $CH_3$ | H | H | H | H | ⬠H (Condensation) | | H |
| B-10 | H | $CH_3CO$ | H | H | H | (i)$C_3H_7$ | H | H | $CH_3$ | $CH_3$ |
| B-11 | H | $C_3H_7$ | (t)$C_8H_{17}$ | H | H | $CH_3$ | H | $CH_3$ | $CH_3$ | $CH_3$ |
| B-12 | Br | H | Br | H | H | H | H | $CH_3$ | $CH_3$ | $CH_3$ |
| B-13 | H | ⬡H | H | H | $CH_3$ | $CH_3$ | H | H | $CH_2OH$ | $CH_3$ |
| B-14 | H | ⏣ | H | H | $CH_3$ | $CH_3$ | H | H | $CH_3$ | $CH_3$ |
| B-15 | H | H | $CH_2=CHCH_2CO$ | $CH_3$ | $CH_3$ | H | H | (OH-phenyl-OH) | | $CH_3$ |

-continued

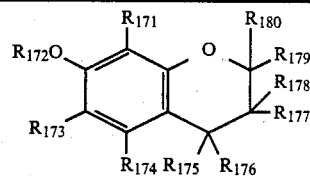

| Compound No. | R₁₇₁ | R₁₇₂ | R₁₇₃ | R₁₇₄ | R₁₇₅ | R₁₇₆ | R₁₇₇ | R₁₇₈ | R₁₇₉ | R₁₈₀ |
|---|---|---|---|---|---|---|---|---|---|---|
| B-16 | H | H | H | CH₃SO₂NH | CH₃ | CH₃ | H | H | ![2,4-dihydroxytolyl] | CH₃ |
| B-17 | H | ![furyl-CH₂] | CH₃ | H | Cl | H | Cl | H | CH₃ | CH₃ |
| B-18 | H | ![benzyl-CH₂] | CH₃CONH | H | H | H | H | H | ![gem-dimethylcyclohexyl (Spiro)] | |
| B-54 | CH₃O | CH₃O | H | H | H | H | H | H | CH₃ | CH₃ |
| B-55 | H | ![(Methylenedioxy)] | | H | H | H | H | H | CH₃ | CH₃ |

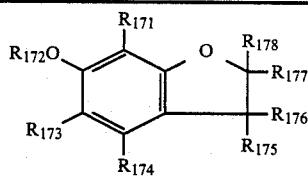

| Compound No. | R₁₇₁ | R₁₇₂ | R₁₇₃ | R₁₇₄ | R₁₇₅ | R₁₇₆ | R₁₇₇ | R₁₇₈ |
|---|---|---|---|---|---|---|---|---|
| B-6 | H | H | H | H | H | ![cyclohexyl H (Condensation)] | | H |
| B-7 | H | H | (i)C₃H₇ | H | H | H | CH₃ | CH₃ |
| B-8 | H | CH₃ | Cl | H | H | H | CH₃ | CH₃ |
| B-19 | H | H | ![cyclohexyl H] | H | CH₃ | CH₃ | CH₃ | CH₃ |
| B-20 | H | CH₂=CHCH₂ | CH₃ | H | CH₃ | CH₃ | CH₃ | H |
| B-21 | H | C₃H₇ | C₃H₇ | H | CH₃ | CH₃ | ![2-pyridyl] | H |
| B-22 | CH₃ | H | CH₃ | H | ![cyclopentyl H (Spiro)] | | H | H |

-continued

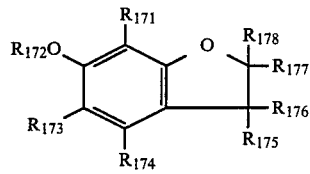

| Compound No. | $R_{171}$ | $R_{172}$ | $R_{173}$ | $R_{174}$ | $R_{175}$ | $R_{176}$ | $R_{177}$ | $R_{178}$ |
|---|---|---|---|---|---|---|---|---|
| B-23 | $CH_3$ | H | 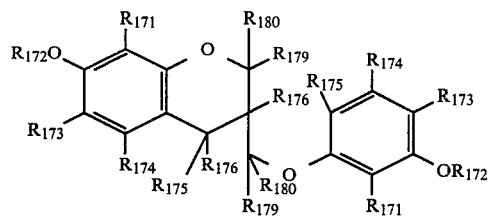 | H | $CH_3$ | $CH_3$ | $CH_3$ | $CH_3$ |

| Compound No. | $R_{171}$ | $R_{172}$ | $R_{173}$ | $R_{174}$ | $R_{175}$ | $R_{176}$ | $R_{179}$ | $R_{180}$ |
|---|---|---|---|---|---|---|---|---|
| B-24 | H | H | H | H | $CH_3$ | $CH_3$ | H | H |
| B-25 | H | H | $CH_3$ | H | $CH_3$ | $CH_3$ | H | H |
| B-26 | H | H | $(t)C_4H_9$ | H | H | H | H | H |
| B-27 | H | $CH_3$ | H | H | $CH_3$ | $CH_3$ | H | H |
| B-28 | H | H | ─⟨p-C₆H₄⟩─$CH_3$ | H | $CH_3$ | $CH_3$ | H | H |
| B-29 | H | H | $C_2H_5COOCH_2$ | H | $CH_3$ | $CH_3$ | H | H |
| B-30 | $CH_3$ | ─$CH_2$─Ph | H | $CH_3$ | $CH_3$ | $CH_3$ | H | H |
| B-31 | Cl | H | H | H | ⟨cyclohexyl, H (Spiro)⟩ | | H | H |
| B-32 | H | H | $CH_3CONH$ | H | $CH_3$ | $CH_3$ | H | H |
| B-33 | $CH_3$ | Ph | $(t)C_8H_{17}$ | H | $CH_3$ | $CH_3$ | H | H |
| B-34 | H | H | Ph─$CH_2$─ | H | $CH_3$ | $CH_3$ | H | H |

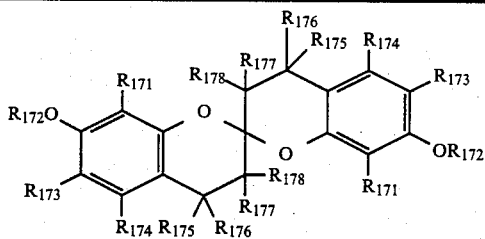

| Compound No. | $R_{171}$ | $R_{172}$ | $R_{173}$ | $R_{174}$ | $R_{175}$ | $R_{176}$ | $R_{177}$ | $R_{178}$ |
|---|---|---|---|---|---|---|---|---|
| B-35 | H | H | H | H | $CH_3$ | $CH_3$ | H | H |
| B-36 | H | $C_3H_7$ | H | H | $CH_3$ | $CH_3$ | H | H |
| B-37 | H | $CH_3$ | $CH_3$ | H | $CH_3$ | $CH_3$ | H | H |
| B-38 | H | H | $(t)C_4H_9$ | H | $CH_3$ | $CH_3$ | H | H |
| B-39 | H | H | —⟨p-tolyl⟩—$CH_3$ | H | $CH_3$ | $CH_3$ | H | H |
| B-40 | H | H | $CH_3SO_2NH$ | H | H | H | H | H |
| B-41 | $CH_3$ | ⟨2-pyridyl⟩ | H | $CH_3$ | $CH_3$ | $CH_3$ | H | H |
| B-42 | Cl | $(t)C_4H_9$ | H | H | ⟨cyclohexyl (Spiro)⟩ | | H | H |
| B-43 | H | $C_{12}H_{25}$ | $CH_3CONH$ | H | $CH_3$ | $CH_3$ | H | H |
| B-44 | H | H | $(t)C_8H_{17}$ | H | $CH_3$ | $CH_3$ | H | H |
| B-45 | H | H | ⟨cyclopentyl H⟩ | H | $CH_3$ | $CH_3$ | H | H |

| Compound No. | $R_{171}$ | $R_{174}$ | $R_{175}$ | $R_{176}$ | $R_{177}$ | $R_{178}$ | $R_{179}$ | $R_{180}$ |
|---|---|---|---|---|---|---|---|---|
| B-46 | H | H | H | H | H | H | $CH_3$ | $CH_3$ |
| B-47 | OH | H | H | H | H | H | $CH_3$ | $CH_3$ |
| B-48 | H | H | H | H | H | H | $CH_3$ | $C_2H_5$ |
| B-49 | H | H | H | H | H | H | ⟨H (Spiro)⟩ | |
| B-50 | $C_3H_7O$ | H | $CH_3$ | H | H | H | $CH_3$ | $CH_3$ |
| B-51 | H | H | H | H | $C_3H_7$ | H | $C_3H_7$ | H |
| B-52 | H | OH | H | H | H | H | $CH_3$ | $CH_3$ |
| B-53 | H | $C_3H_7O$ | H | H | H | H | $CH_3$ | $CH_3$ |

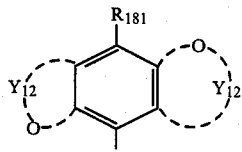

General formula [C]

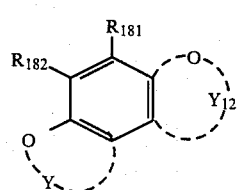

General formula [D]

In these formulae, $R_{181}$ and $R_{182}$ express a hydrogen atom, a halogen atom, an alkyl group, an alkenyl group, an alkoxy group, an alkenyloxy group, a hydroxy group, an aryl group, an aryloxy group, an acyl group, an acylamino group, an acyloxy group, a sulfonamide group, or an alkoxy carbonyl group.

The groups mentioned above may respectively be substituted with other substituents. For example, a halogen atom, an alkyl group, an alkenyl group, an alkoxy group, an aryloxy group, a hydroxy group, an alkoxycarbonyl group, an aryloxycarbonyl group, an acrylamino group, a carbamoyl group, a sulfonamido group, a sulfamoyl group, and so forth can be mentioned.

$Y_{12}$ expresses a group of atoms necessary for forming a dichroman or dicoumaran ring together with a benzene ring.

The chroman or coumaran ring may be substituted with a halogen atom, an alkyl group, a cycloalkyl group, an alkoxy group, an alkenyl group, an alkenyloxy group, a hydroxy group, an aryl group, an aryloxy group, or a heterocyclic group, and the ring may, moreover, form a spiro ring.

Of the compounds which are expressed by the general formulae [C] and [D], those compounds which are specially useful for the present invention are included in those compounds which are expressed by the general formulae [C-1], [C-2], [D-1], and [D-2].

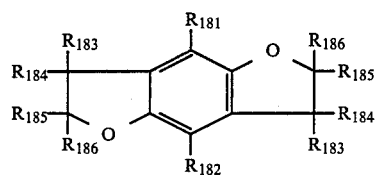
General formula [C-1]

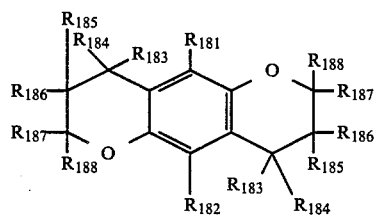
General formula [C-2]

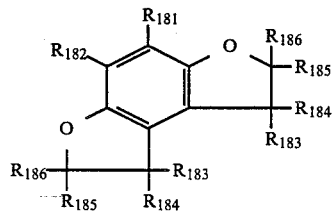
General formula [D-1]

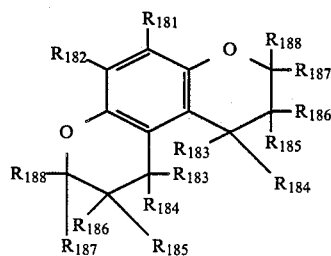
General formula [D-2]

$R_{181}$ and $R_{182}$ in the general formulae [C-1], [C-2], [D-1] and [D-2] have the same meaning as that in the general formulae [C] and [D] given above, and $R_{183}$, $R_{184}$, $R_{185}$, $R_{186}$, $R_{187}$, $R_{188}$ express a hydrogen atom, a halogen atom, an alkyl group, an alkoxy group, a hydroxy group, an alkenyl group, an alkenyloxy group, an aryl group, an aryloxy group, or a heteroxyclic group. Furthermore, $R_{183}$ and $R_{184}$, $R_{184}$ and $R_{185}$, $R_{185}$ and $R_{186}$, $R_{186}$ and $R_{187}$, and $R_{187}$ and $R_{188}$ may develop a ring with each other to form a carbon ring, and the carbon ring may, moreover, be substituted with an alkyl group.

Those compounds which have a hydrogen atom, an alkyl group, an alokoxy group, a hydroxy group, or a cycloalkyl group for $R_{181}$ and $R_{182}$ and a hydrogen atom, an alkyl group, or a cycloalkyl group for $R_{183}$, $R_{184}$, $R_{185}$, $R_{186}$, $R_{187}$, and $R_{188}$ in the above-mentioned general formulae [C-1], [C-2], [D-1] and [D-2], are specially useful.

The compounds which are expressed in the general formula [C] and [D] include those compounds which are described in The Journal of The Japan Chemical Society (J. Chem. Soc. part C), 1968. (14), pp. 1937~18, The Journal of Organic Synthetic Chemical Association, 1970, 28(1), pp. 60~65, and Tetrahedron Letters, 1973. (29), pp. 2707~2710, 1973. (29), pp. 2707~2710, and can be synthesized in accordance with the process described in these publications.

The amount used of any compound expressed in the general formulae [C] and [D] mentioned above is preferably 5~300 mol %, and more preferably 10~200 mol %, for the magenta coupler relevant to the present invention as mentioned above.

In the following part, concrete representative examples of these compounds are presented.

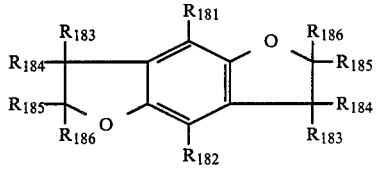

| Compound No. | $R_{181}$ | $R_{182}$ | $R_{183}$ | $R_{184}$ | $R_{185}$ | $R_{186}$ |
|---|---|---|---|---|---|---|
| C-11 | H | H | H | H | $CH_3$ | $CH_3$ |
| C-12 | H | H | H | H | 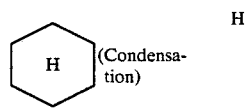(Spiro) | |
| C-13 | H | H | H | 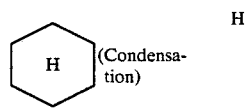(Condensation) | | H |

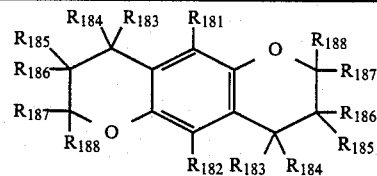

| Compound No. | $R_{181}$ | $R_{182}$ | $R_{183}$ | $R_{184}$ | $R_{185}$ | $R_{186}$ | $R_{187}$ | $R_{188}$ |
|---|---|---|---|---|---|---|---|---|
| C-1 | H | H | H | H | H | H | H | H |
| C-2 | H | H | H | H | H | H | $CH_3$ | $CH_3$ |
| C-3 | H | H | $CH_3$ | H | H | H | $CH_3$ | $CH_3$ |
| C-4 | $CH_3$ | H | $CH_3$ | $CH_3$ | H | H | $CH_3$ | $CH_3$ |
| C-5 | OH | H | H | H | H | H | $C_2H_5$ | $CH_3$ |
| C-6 | $OCH_3$ | H | H | H | H | H | H | H |
| C-7 | $OC_3H_7$ | H | H | H | H | H | H | H |
| C-8 | $OC_{12}H_{25}$ | H | H | H | H | H | H | H |
| C-9 | $CH_3COO$ | H | H | H | H | H | $CH_3$ | $CH_3$ |
| C-10 | $CH_3CONH$ | H | H | H | H | \multicolumn{3}{c}{cyclohexyl H (Spiro)} |
| C-14 | $(CH_3)_2CClCHCH_2$ | $(CH_3)_2CClCH_2CH_2$ | H | H | H | H | $CH_3$ | $CH_3$ |
| C-15 | $CH_3$ | $CH_3$ | H | H | H | H | $CH_3$ | $CH_3$ |
| C-16 | $(CH_3)_2C=CHCH_2$ | $(CH_3)_2C=CCH_2$ | H | H | H | H | $CH_3$ | $CH_3$ |
| C-17 | Cl | H | H | H | H | H | H | H |

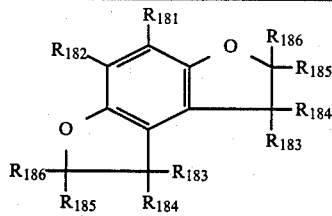

| Compound No. | $R_{181}$ | $R_{182}$ | $R_{183}$ | $R_{184}$ | $R_{185}$ | $R_{186}$ |
|---|---|---|---|---|---|---|
| D-1 | $CH_3$ | $CH_3$ | H | H | H | H |

-continued

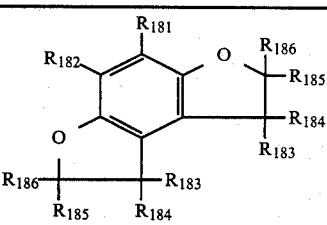

| Compound No. | $R_{181}$ | $R_{182}$ | $R_{183}$ | $R_{184}$ | $R_{185}$ | $R_{186}$ |
|---|---|---|---|---|---|---|
| D-2 | H | H | H | H | $CH_3$ | $CH_3$ |

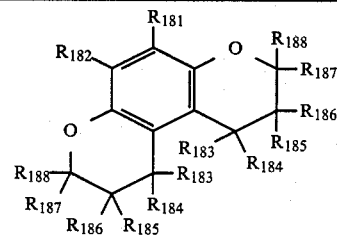

| Compound No. | $R_{181}$ | $R_{182}$ | $R_{183}$ | $R_{184}$ | $R_{185}$ | $R_{186}$ | $R_{187}$ | $R_{188}$ |
|---|---|---|---|---|---|---|---|---|
| D-3 | H | H | H | H | H | H | H | H |
| D-4 | H | H | H | H | H | H | $CH_3$ | $CH_3$ |
| D-5 | $CH_3$ | $CH_3$ | H | H | H | H | $CH_3$ | $CH_3$ |
| D-6 | $(CH_3)_2CClCH_2CH_2$ | $(CH_3)_2CClCH_2CH_2$ | H | H | H | H | $CH_3$ | $CH_3$ |
| D-7 | H | H | Cl | H | Cl | H | H | H |

-continued

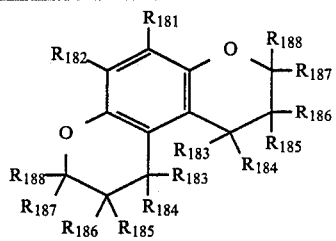

| Compound No. | $R_{181}$ | $R_{182}$ | $R_{183}$ | $R_{184}$ | $R_{185}$ | $R_{186}$ | $R_{187}$ | $R_{188}$ |
|---|---|---|---|---|---|---|---|---|
| D-8 | H | H | H | H | H | H | 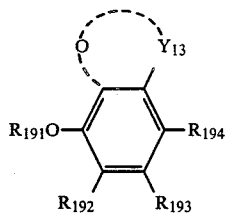 (Spiro) | |
| D-9 | $CH_3O$ | H | H | H | H | H | 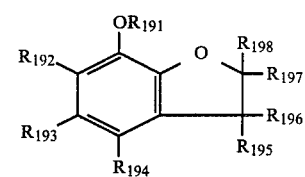 | H |
| D-10 | H | H | H | H | H | H | $CH_2OH$ | $CH_3$ |
| D-11 | 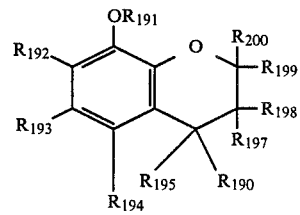 | H | H | H | H | H | $CH_3$ | $CH_3$ |

General formula [E]

In this formula, $R_{191}$ expresses a hydrogen atom, an alkyl group, an alkenyl group, an aryl group, an acyl group, a cycloalkyl group, or a heterocyclic group, and $R_{193}$ expresses a hydrogen atom, a halogen atom, an alkyl group, an alkenyl group, an aryl group, an aryloxy group, an acyl group, an acylamino group, an acyloxy group, a sulfonamido group, a cycloalkyl group, or an alkoxy carbonyl group.

$R_{192}$ and $R_{194}$ express a hydrogen atom, a halogen atom, an alkyl group, an alkenyl group, an aryl group, an acyl group, an acylamino group, a sulfonamido group, a cycloalkyl group, or an alkoxycarbonyl group.

The groups which are cited hereinabove may be substituted respectively with other substituents, for which an alkyl group, an alkenyl group, an alkoxy group, an aryl group, an aryloxy group, a hydroxy group, an alkoxycarbonyl group, an aryloxycarbonyl group, an acylamino group, a carbamoyl group, a sulfonamido group, a sulfamoyl group, and so forth may be cited.

$R_{191}$, and $R_{192}$, moreover, may form a closed ring with each other, thereby forming a five- or six-membered ring.

At such a time $R_{193}$ and $R_{194}$ express a hydrogen atom, a halogen atom, an alkyl group, an alkenyl group, an alkoxy group, an alkenyloxy group, a hydroxy group, an aryl group, an aryloxy group, an acyl group, an acylamino group, an acyloxy group, a sulfonamide group, an alkoxy carbonyl group.

$Y_{13}$ expresses a group of atoms necessary for the formation of a chroman or coumaran ring.

The chroman or coumaran ring may be substituted with a halogen atom, an alkyl group, a cycloalkyl group, an alkoxy group, an alkenyl group, an alkenyloxy group, a hydroxy group, an aryl group, an aryloxy group, or a heterocyclic group, and the ring may, moreover, form a spiro ring.

Of the compounds expressed by the general formula [E], those compounds which are specially useful for the present invention are included in the compounds indicated in the general formulae [E-1], [E-2], [E-3], [E-4], and [E-5].

General formula [E-1]

General formula [E-2]

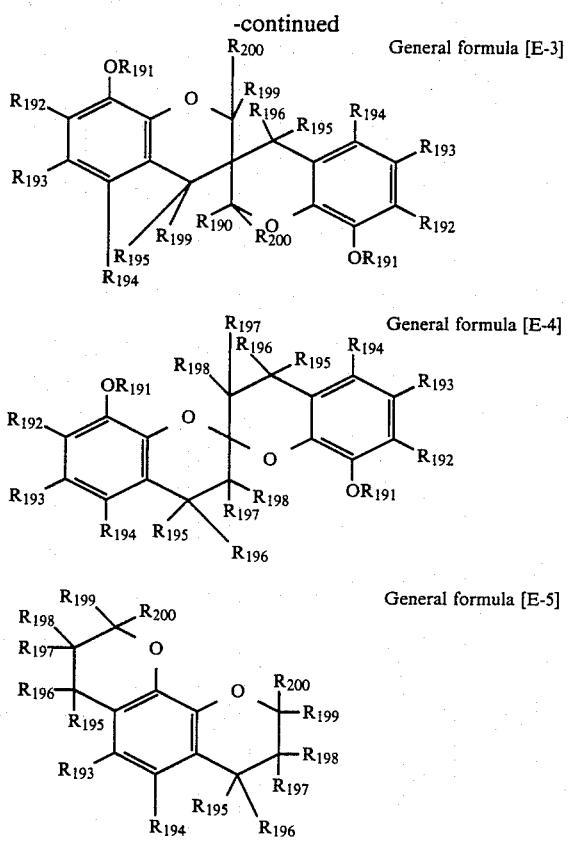

General formula [E-3]

General formula [E-4]

General formula [E-5]

$R_{191}$, $R_{192}$, $R_{193}$, and $R_{194}$ in the general formulae [E-1]~[E-5] have the same meaning as that of those in the general formula [E] mentioned above, and $R_{195}$, $R_{196}$, $R_{197}$, $R_{198}$, $R_{199}$ and $R_{200}$ express a hydrogen atom, a halogen atom, an alkyl group, an alkoxy group, a hydroxy group, an alkenyl group, an alkenyloxy group, an aryl group, an aryloxy group, or a heterocyclic group. Furthermore, $R_{195}$ and $R_{196}$, $R_{196}$ and $R_{197}$, $R_{197}$ and $R_{198}$, $R_{198}$ and $R_{199}$, and $R_{199}$ and $R_{200}$ may form a ring with each other, thereby forming a carbon ring, and the carbon ring, moreover, may be substituted with an alkyl group.

Those compounds which have a hydrogen atom, an alkyl group, or a cycloalkyl group for $R_{191}$, $R_{192}$, $R_{193}$ and $R_{194}$ in the above-mentioned general formulae [E-1]~[E-5], those compounds which have a hydrogen atom, an alkyl group, an alkoxy group, a hydroxy group, or a cycloalkyl group for $R_{193}$ and $R_{194}$ in the above-mentioned general formula [E-5], and also those compounds which have a hydrogen atom, an alkyl group, or a cycloalkyl group for $R_{195}$, $R_{196}$, $R_{197}$, $R_{198}$, $R_{199}$, and $R_{200}$ in the above-mentioned general formula [E-1]~[E-5] are specially useful.

Those compounds which are expressed in the general formula [E] include the compounds which are described in Tetrahedron Letters, 1965. (8), pp. 457~460, The Journal of Japan Chemical Society (J. Chem. Soc. part C), 1966. (22), pp. 2013~2016 and Zh. Org. Khim 1970, (6), pp. 1230~1237, and can be synthesized in accordance with the method described in these publications.

The amount used of the compounds expressed in the general formula [E-1] mentioned above is preferably 5~300 mol %, and more preferably 10~200 mol %, for the magenta coupler relevant to the present invention as mentioned above.

In the following part, concrete representative examples of these compounds are presented.

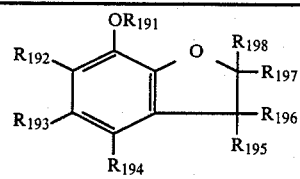

| Compound No. | $R_{191}$ | $R_{192}$ | $R_{193}$ | $R_{194}$ | $R_{195}$ | $R_{196}$ | $R_{197}$ | $R_{198}$ |
|---|---|---|---|---|---|---|---|---|
| E-19 | H | H | H | H | H | | 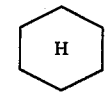 (Condensation) | H |
| E-20 | $C_3H_7$ | H | H | H | H | | 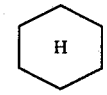 (Condensation) | H |
| E-21 | H | H | H | H | H | H |  (Spiro) | |
| E-22 | $CH_3$ | H | H | H | H | | 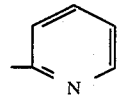 | H |

-continued

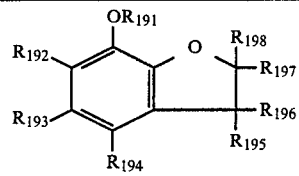

| Compound No. | $R_{191}$ | $R_{192}$ | $R_{193}$ | $R_{194}$ | $R_{195}$ | $R_{196}$ | $R_{197}$ | $R_{198}$ |
|---|---|---|---|---|---|---|---|---|
| E-23 | H | H | H | H | H | H | $CH_3$ | $CH_3$ |
| E-24 | $CH_3$ | H | cyclopentyl | H | H | H | $CH_3$ | $CH_3$ |
| E-25 | $C_6H_5CO$ | H | H | H | H | H | $CH_3$ | $CH_3$ |
| E-26 | $C_{12}H_{25}$ | H | H | H | $CH_3$ | $CH_3$ | $CH_3$ | $CH_2OH$ |

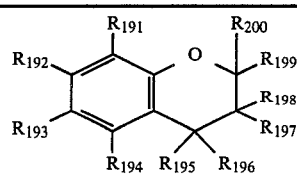

| Compound | $R_{191}$ | $R_{192}$ | $R_{193}$ | $R_{194}$ | $R_{195}$ | $R_{196}$ | $R_{197}$ | $R_{198}$ | $R_{199}$ | $R_{200}$ |
|---|---|---|---|---|---|---|---|---|---|---|
| E-1 | H | H | H | H | H | H | H | H | H | H |
| E-2 | H | H | H | H | H | H | H | H | $CH_3$ | $CH_3$ |
| E-3 | H | H | H | H | $CH_3$ | H | H | H | $CH_3$ | $CH_3$ |
| E-4 | H | H | $CH_2=CHCH_2$ | H | H | H | H | H | $CH_3$ | $CH_3$ |
| E-5 | $CH_3$ | H | H | H | H | H | H | H | $CH_3$ | $CH_3$ |
| E-6 | $C_3H_7$ | H | H | H | H | H | H | H | $CH_3$ | $CH_3$ |
| E-7 | $C_{12}H_{25}$ | H | H | H | $CH_3$ | H | H | H | $CH_3$ | $CH_3$ |
| E-8 | $C_6H_5CH_2$ | H | H | H | H | H | H | H | H | H |
| E-9 | cyclohexyl | H | H | H | H | H | H | H | $CH_3$ | $CH_3$ |
| E-10 | furyl-methyl | H | H | H | H | H | H | H | $CH_3$ | $CH_3$ |
| E-11 | H | H | H | H | H | H | H | H | $CH_3$ | $C_{16}H_{33}$ |
| E-12 | H | H | phenyl | H | H | H | H | H | $CH_3$ | $CH_3$ |
| E-13 | $CH_3$ | H | $CH_3CO$ | H | H | H | H | H | $CH_3$ | $CH_3$ |
| E-14 | $CH_3$ | H | H | H | H | Br | Br | H | H | H |
| E-15 | $CH_3$ | H | H | H | H | Cl | Cl | H | H | H |
| E-16 | $CH_3$ | H | H | H | H | $CH_3O$ | Br | H | H | H |
| E-17 | $CH_3$ | H | H | H | H | OH | Br | H | $CH_3$ | $CH_3$ |
| E-18 | $CH_3$ | H | H | H | H | $C_2H_5O$ | OH | H | $CH_3$ | $CH_3$ |

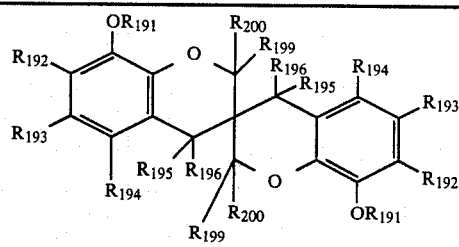

| Compound No. | $R_{191}$ | $R_{192}$ | $R_{193}$ | $R_{194}$ | $R_{195}$ | $R_{196}$ | $R_{199}$ | $R_{200}$ |
|---|---|---|---|---|---|---|---|---|
| E-27 | H | H | H | H | H | H | H | H |
| E-28 | $CH_3$ | H | H | H | H | H | H | H |
| E-29 | 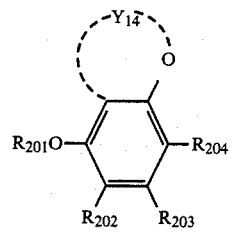 | H | H | H | H | H | H | H |
| E-30 | H | H | $CH_3$ | H | H | H | $CH_3$ | $CH_3$ |
| E-31 | $C_3H_7$ | H | H | H | H | H | H | H |
| E-32 | $C_3H_7$ | H | H | H | $CH_3$ | $CH_3$ | H | H |
| E-37 | H | H | H | $CH_3CONH$ | H | H | H | H |
| E-38 | CO | H | H | H | H | H | H | H |

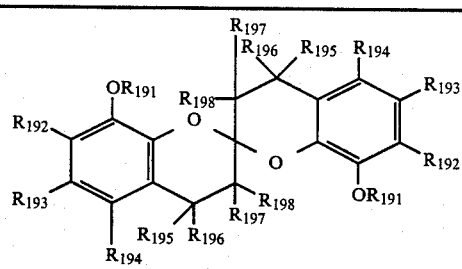

| Compound No. | $R_{191}$ | $R_{192}$ | $R_{193}$ | $R_{194}$ | $R_{195}$ | $R_{196}$ | $R_{197}$ | $R_{198}$ |
|---|---|---|---|---|---|---|---|---|
| E-33 | H | H | H | H | H | H | H | H |
| E-34 | H | H | H | H | $CH_3$ | $CH_3$ | H | H |
| E-35 | $C_{12}H_{25}$ | H | H | H | $CH_3$ | $CH_3$ | H | H |
| E-36 | $CH_3$ | H | $CH_3$ | H | $CH_3$ | $CH_3$ | H | H |

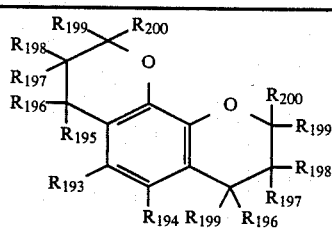

| Compound No. | $R_{193}$ | $R_{194}$ | $R_{195}$ | $R_{196}$ | $R_{197}$ | $R_{198}$ | $R_{199}$ | $R_{200}$ |
|---|---|---|---|---|---|---|---|---|
| E-39 | H | H | H | H | H | H | H | H |
| E-40 | H | H | H | H | H | H | $CH_3$ | $CH_3$ |
| E-41 | OH | H | H | H | H | H | $CH_3$ | $CH_3$ |
| E-42 | $C_3H_7O$ | H | $CH_3$ | $CH_3$ | H | H | H | H |

General formula [F]

[Structure showing benzene ring with $Y_{14}$, O, $R_{201}O$, $R_{204}$, $R_{202}$, $R_{203}$ substituents]

In this formula, $R_{201}$ expresses a hydrogen atom, an alkyl group, an alkenyl group, an aryl group, an acyl group, a cycloakyl group, or a heterocyclic group, and $R_{202}$ expresses a hydrogen atom, a halogen atom, an alkyl group, an alkenyl group, an aryl group, an aryloxy group, an acyl group, an acylamino group, an acyloxy group, a sulfonamide group, a cycloalkyl group, or an alkoxycrabonyl group.

$R_{203}$ expresses a hydrogen atom, a halogen atom, an alkyl group, an alkenyl gruop, an aryl group, an acryl group, an acylamino group, an sulfonamido group, a cycloalkyl group, or an alkoxycarbonyl group.

$R_{204}$ expresses a hydrogen atom, a halogen atom, an alkyl group, an alkenyl group, an alkoxy group, an alkenyloxy group, a hydroxy group, an aryl group, an aryloxy group, an acyl group, an acylamino group, an acyloxy group, a sulfonamido group, or an alkoxycarbonyl group.

Those groups which are cited above may respectively be substituted with other substituents. For example an alkyl group, an alkenyl group, an alkoxy group, an aryl group, an aryloxy group, a hydroxy group, an alkoxycarbonyl group, an aryloxycarbonyl group, an acylamino group, a carbamoyl group, a sulfonamido group, a sulfamoyl group, and so forth can be cited.

Furthermore, $R_{201}$ and $R_{202}$ may develop a closed ring with each other, thereby forming a five- to six-members ring. At such a time, $R_{203}$ and $R_{204}$ expresses a hydrogen atom, a halogen atom, an alkyl group, an alkenyl group, an alkoxy group, an alkenyloxy group, a hydroxy group, an aryl group, an aryloxy group, an acyl group, an acylamino group, an acyloxy group, a sulfonamido group, or an alkoxycarbonyl group.

$Y_{14}$ expresses a group of atoms necessary for the formation of a chroman or coumaran ring.

The chroman or coumaran ring may be substituted with a halogen atom, an alkyl group, a cycloalkyl group, an alkoxy group, an alkenyl group, an alkenyloxy group, a hydroxy group, an aryl group, an aryloxy group, or a heterocyclic group, and may, moreover, form a spiro ring.

Of the compounds expressed by the general formula [F], those compounds which are specially useful for the present invention are included in the compounds indicated by the general formulae [F-1], [F-2], [F-3], [F-4], and [F-5].

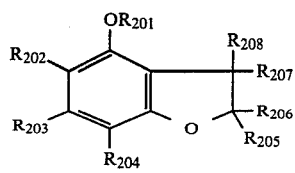

General formula [F-1]

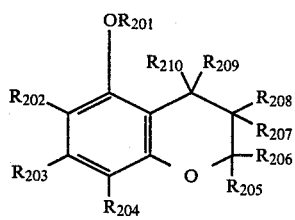

General formula [F-2]

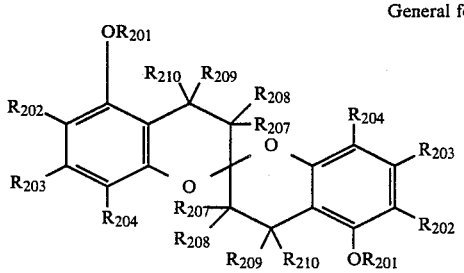

General formula [F-3]

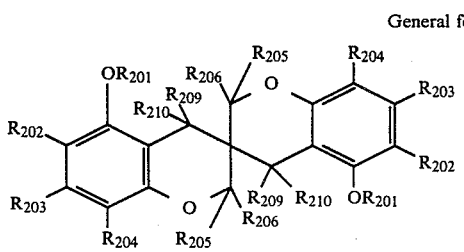

General formula [F-4]

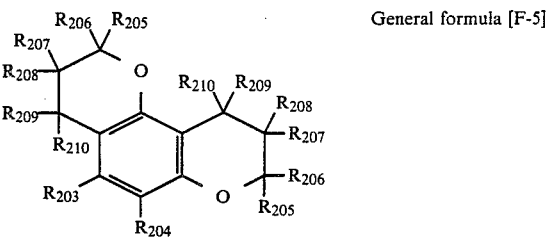

General formula [F-5]

$R_{201}$, $R_{202}$, $R_{203}$, and $R_{204}$ in the general formulae [F-1] and [F-5] have the same meaning as that in the general formula [F] given above, and $R_{205}$, $R_{206}$, $R_{207}$, $R_{208}$, $R_{209}$, and $R_{210}$ express a hydrogen atom, a halogen atom, an alkyl group, an alkoxy group, a hydroxy group, an alkenyl group, an alkenyloxy group, an aryl group, an aryloxy group, or heterocyclic group.

Furthermore, $R_{205}$ and $R_{206}$, $R_{206}$ and $R_{207}$, $R_{207}$ and $R_{208}$, $R_{208}$ and $R_{209}$, and $R_{209}$ and $R_{210}$ may make a ring with each other to form a carbon ring, and the carbon ring may be substituted with an alkyl group.

Moreover, in the general formulae [F-3], [F-4] and [F-5], the two sets of $R_{201} \sim R_{210}$ may be either identical with, or different from, each other.

Those compounds which have a hydrogen atom, an alkyl group, and a cycloalkyl group for $R_{201}$, $R_{202}$, and $R_{203}$, a hydrogen atom, an alkyl group, an alkoxy group, a hydroxy group, or a cycloalkyl group for $R_4$, and a hydrogen atom, an alkyl group, or a cycloalkyl group for $R_{205}$, $R_{206}$, $R_{207}$, $R_{208}$, $R_{209}$, and $R_{210}$ in the general formulae [F-1], [F-2], [F-3], [F-4] and [F-5] mentioned above are specially useful.

The compounds expressed by the general formula [F] include those compounds which are described in Tetrahedron Letters, 1970, Vol. 26, pp. 4743~4751, The Journal of Japan ChemicalSociety, 1972, No. 10, pp. 1987~1990, Synthesis, 1975, Vol. 6, pp. 392~393, Bul. Soc. Chim, Belg., 1975, Vol. 84 (7), pp. 747~759 and can be synthesized in accordance with the process described in these publications.

The amount used of the compounds expressed by the general formula [F] is preferably 5~300 mol %, and more preferably 10~200 mol, for the magenta coupler relevant to the present invention as mentioned above.

In the following part are presented concrete representative examples of the compounds expressed by the general formula [F].

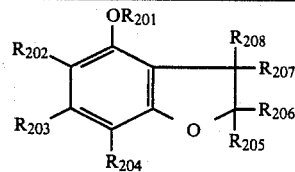

| Compound No | $R_{201}$ | $R_{202}$ | $R_{203}$ | $R_{204}$ | $R_{205}$ | $R_{206}$ | $R_{207}$ | $R_{208}$ |
|---|---|---|---|---|---|---|---|---|
| F-11 | H | H | H | H | H |  (Condensation) | | H |
| F-12 | $C_3H_7$ | H | H | H | H |  (Condensation) | | H |
| F-13 | H | H | H | H | H | H | H | H |
| F-14 | H | H | H | H | H | H | $CH_3$ | H |
| F-15 | H | H | $CH_3$ | H | H | H | $CH_3$ | H |
| F-16 | H | H |  | H | H | H | $CH_3$ | H |
| F-17 | H | H |  | H | H | H | $CH_3$ | H |
| F-18 | $C_3H_7$ | H | $CH_3$ | H | H | H | $CH_3$ | H |
| F-19 |  | H | H | H | H | 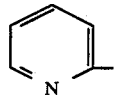 (Spiro) | H | H |
| F-24 | $CH_2=CHCH_2$ | $CH_3$ | $CH_3$ | H | H | $C_2H_5O$ | $CH_3$ | $CH_3$ |
| F-25 | $C_3H_7$ | H | H | H | H |  | $CH_3$ | $CH_3$ |
| F-26 | H | $CH_3$ | $CH_3$ | H | H | H | 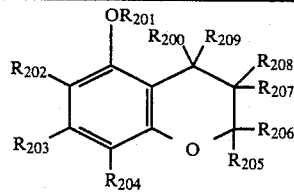 (Spiro) | |

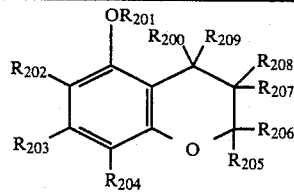

| Compound No. | $R_{201}$ | $R_{202}$ | $R_{203}$ | $R_{204}$ | $R_{205}$ | $R_{206}$ | $R_{207}$ | $R_{208}$ | $R_{209}$ | $R_{200}$ |
|---|---|---|---|---|---|---|---|---|---|---|
| F-1 | H | H | H | H | H | H | H | H | H | H |
| F-2 | H | H | H | H | $CH_3$ | $CH_3$ | H | H | $CH_3$ | H |
| F-3 | H | H | H | H | $CH_3$ | $CH_3$ | H | H | H | H |

-continued

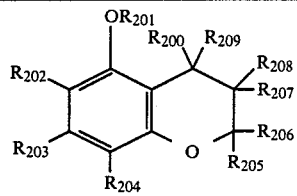

| Compound No. | R201 | R202 | R203 | R204 | R205 | R206 | R207 | R208 | R209 | R200 |
|---|---|---|---|---|---|---|---|---|---|---|
| F-4 | H | $(CH_3)_2C=CHCH_2$ | H | H | $CH_3$ | $CH_3$ | H | H | H | H |
| F-5 | $CH_3$ | H | H | H | $CH_3$ | $CH_3$ | H | H | H | H |
| F-6 | $C_3H_7$ | H | H | H | $CH_3$ | $CH_3$ | H | H | H | H |
| F-7 | $C_{12}H_{25}$ | H | H | H | $CH_3$ | $CH_3$ | H | H | H | H |
| F-8 | ⌬–$CH_2$– | H | H | H | $CH_3$ | $CH_3$ | H | H | H | H |
| F-9 | cyclohexyl | H | H | H | $CH_3$ | $CH_3$ | H | H | H | H |
| F-10 | furyl-methyl | H | H | H | $CH_3$ | $CH_3$ | H | H | H | H |
| F-20 | H | Cl | H | H | H | cyclopentyl (Condensation) | | H | H | H |
| F-21 | H | H | H | H | $CH_3$ | $CH_2OH$ | H | H | $CH_3$ | $CH_3$ |
| F-22 | $C_3H_7$ | $(t)C_8H_{17}$ | H | H | $C_2H_5$ | $CH_3$ | H | H | H | H |
| F-23 | $CH_3CO$ | H | H | H | $CH_3$ | $CH_3$ | H | H | $CH_3$ | H |

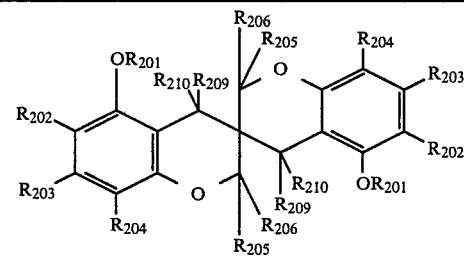

| Compound No. | R201 | R202 | R203 | R204 | R205 | R206 | R209 | R210 |
|---|---|---|---|---|---|---|---|---|
| F-27 | H | H | H | H | H | H | $CH_3$ | $CH_3$ |
| F-28 | $C_3H_7$ | H | H | H | H | H | $CH_3$ | $CH_3$ |
| F-29 | H | H | H | $(t)C_8H_{17}$ | H | H | H | H |
| F-30 | H | Cl | H | H | H | H | cyclohexyl (Spiro) | |
| F-31 | ⌬–$CH_2$– | H | H | H | H | H | $CH_3$ | $CH_3$ |

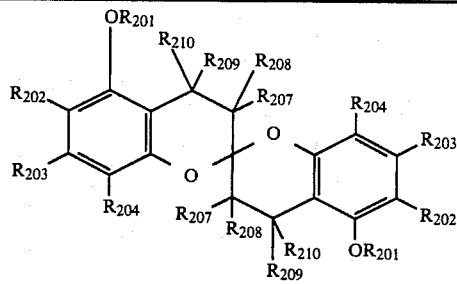

| Compound No. | $R_{201}$ | $R_{202}$ | $R_{203}$ | $R_{204}$ | $R_{207}$ | $R_{208}$ | $R_{209}$ | $R_{210}$ |
|---|---|---|---|---|---|---|---|---|
| F-32 | H | H | H | H | H | H | $CH_3$ | $CH_3$ |
| F-33 | $CH_3$ | H | H | H | H | H | $CH_3$ | $CH_3$ |
| F-34 | H | $CH_3$ | H | H | H | H | H | H |
| F-35 | H | H | H | (t)$C_4H_9$ | H | H | $CH_3$ | $CH_3$ |
| F-36 | H | $CH_3$-〈C6H4〉- | H | H | H | H | $CH_3$ | $CH_3$ |
| F-37 | H | H | H | $CH_3SO_2NH$ | H | H | H | H |
| F-38 | (furyl-CH3) | H | H | H | H | H | $CH_3$ | $CH_3$ |
| F-39 | $C_{12}H_{25}$ | H | H | H | H | H | $CH_3$ | $CH_3$ |
| F-40 | 〈C6H5〉-CO | H | H | H | H | H | (cyclohexyl, Spiro) | |
| F-41 | H | H | H (cyclopentyl) | H | H | H | $CH_3$ | $CH_3$ |

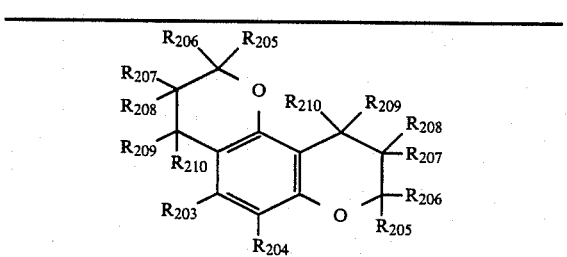

| Compound No. | $R_{203}$ | $R_{204}$ | $R_{205}$ | $R_{206}$ | $R_{207}$ | $R_{208}$ | $R_{209}$ | $R_{210}$ |
|---|---|---|---|---|---|---|---|---|
| F-42 | H | H | $CH_3$ | $CH_3$ | H | H | H | H |
| F-43 | H | H | (Spiro cyclopentyl) | | H | H | H | H |
| F-44 | H | OH | $CH_3$ | $CH_3$ | H | H | $CH_3$ | H |
| F-45 | H | $C_3H_7O$ | H | H | H | H | $CH_3$ | $CH_2OH$ |
| F-46 | OH | H | $CH_3$ | $CH_3$ | H | H | H | H |
| F-47 | $C_3H_7O$ | H | $CH_3$ | $CH_3$ | H | H | H | H |

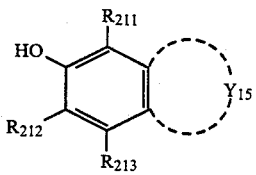

General formula [G]

In this formula, $R_{211}$ and $R_{213}$ respectively express a hydrogen atom, a halogen atom, an akyl group, an alkenyl group, an alkoxy group, a hydroxy group, an aryl group, an aryloxy group, an acyl group, an acylamino group, an acyloxy group, a sulfonamido group, a cyloalkyl group, or an alkoxycarbonyl group.

$R_{212}$ expresses a hydrogen atom, a halogen atom, an alkyl group, an alkenyl group, a hydroxy group, an aryl group, an acyl group, an acylamino group, an acyloxy group, a sulfonamido group, a cycloalkyl group, or an alkoxycarbonyl group.

The groups cited above may be substituted respectively with other substituents. As such substituents, an alkyl group, an alkenyl group, an alkoxy group, an aryl group, an aryloxy group, a hydroxy group, an alkoxycarbonyl group, an aryloxycarbonyl group, an acylamino group, a carbamoyl group, a sulfonamido group, a sulfamoyl group, and so forth can be cited.

Moreover, $R_{212}$ and $R_{213}$ may make a closed ring with each other, thereby forming a five- or six-membered hydrocarbon ring. This five- or six-membered hydrocarbon ring may be substituted with a halogen atom, an alkyl group, a cycloalkyl group, an alkoxy group, an alkenyl group, a hydroxy group, an aryl group, an aryloxy group, or a heterocyclic ring, and so forth.

$Y_{15}$ expresses a group of atoms necessary for the formation of an indan ring. The indan ring may be substituted with a halogen atom, an alkyl group, an alkenyl group, an alkoxy group, a cycloalkyl group, a hydroxy, an aryl group, an aryloxy group, or a heterocyclic group, and so on, and may, moreover form a spiro ring.

Of the compounds expressed by the genral formula [G], those which are specially useful for the present invention are included in the compounds expressed by the general formulae [G-1]~[G-3].

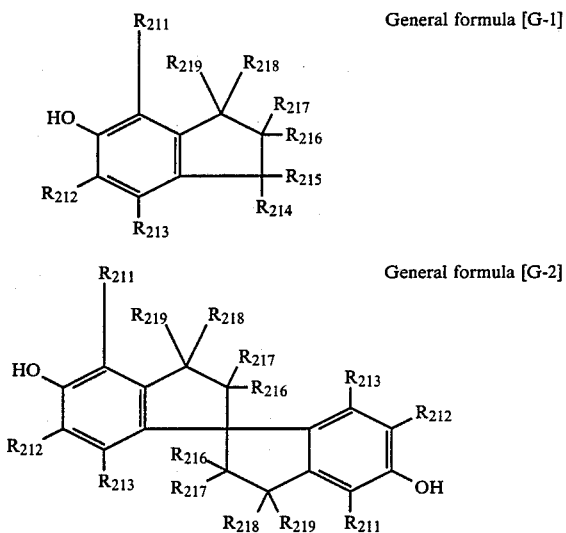

General formula [G-1]

General formula [G-2]

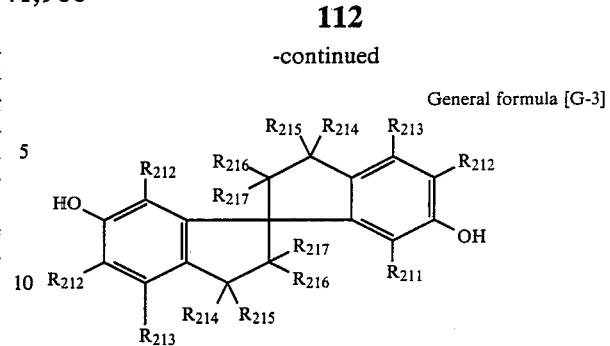

General formula [G-3]

$R_{211}$, $R_{212}$, and $R_{213}$ in the general formulae [G-1]~[G-3] are synonymous with those in the general formula [G], and $R_{214}$, $R_{215}$, $R_{216}$, $R_{217}$, $R_{218}$, and $R_{219}$ respectively express a hydrogen atom, a halogen atom, an alkyl group, an alkoxy group, an alkenyl group, hydroxy group, an aryl group, an aryloxy group, or a heterocyclic group. $R_{214}$ and $R_{215}$, $R_{215}$ and $R_{216}$, $R_{216}$ and $R_{217}$, $R_{217}$ and $R_{218}$, and $R_{218}$ and $R_{219}$ may make a closed ring with each other, thereby forming a hydrocarbon ring, and the hydrocarbon ring may, moreover, be substituted with an alkyl group.

The compounds which have a hydrogen atom, an alkyl group, an alkoxy group, a hydroxy group, or a cycloalkyl group for $R_{211}$ and $R_{213}$, a hydrogen atom, an alkyl group, a hydroxy group, or a cycloalkyl group for $R_{212}$, a hydrogen atom, an alkyl group, or a cycloalkyl group for $R_{214}$, $R_{215}$, $R_{216}$, $R_{217}$, $R_{218}$, and $R_{219}$ in the general formulae [G-1]~[G-3] mentioned above are specially useful.

Of the compounds which are expressed by the general formula [G] mentioned above, the amount used is preferably 5~300 mol %, and more preferably 10~200 mol %, of the magenta coupler.

In the following part, representative concrete examples are given for the compounds expressed by the general formula [G].

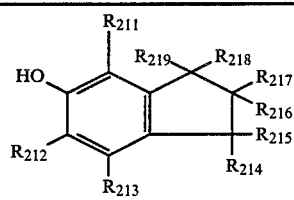

| Compound No. | $R_{211}$ | $R_{212}$ | $R_{213}$ | $R_{214}$ | $R_{215}$ | $R_{216}$ | $R_{217}$ | $R_{218}$ | $R_{219}$ |
|---|---|---|---|---|---|---|---|---|---|
| G-1 | H | H | H | H | H | H | H | H | H |
| G-2 | H | H | H | H | H | H | H | $CH_3$ | $CH_3$ |
| G-3 | H | H | H | H | H | H | H | $CH_3$ | $C_{16}H_{33}$ |
| G-4 | H | OH | H | H | H | H | H | $CH_3$ | $C_{16}H_{33}$ |
| G-5 | H | H | H | $CH_3$ | $CH_3$ | H | H | $CH_3$ | $CH_3$ |
| G-6 | H | Cl | H | $CH_3$ | $CH_3$ | H | H | $CH_3$ | $CH_3$ |
| G-7 | Cl | Cl | H | $CH_3$ | $CH_3$ | H | H | $CH_3$ | $CH_3$ |
| G-8 | H | H | $CH_3$ | $CH_3$ | $CH_3$ | H | H | $CH_3$ | $CH_3$ |
| G-9 | H | H | H | H | ⬡ H | (Condensation) H | H | H | H |
| G-10 | H | H | H | H | H | H | H | ⬠ H | (Spiro) |
| G-11 | H | $C_3H_7$ | H | $CH_3$ | $CH_3$ | H | H | $CH_3$ | $CH_3$ |

-continued

| | | | | | | | | |
|---|---|---|---|---|---|---|---|---|
| G-12 | H | (t)C$_8$H$_{17}$ | H | CH$_3$ | CH$_3$ | H | H | CH$_3$ | CH$_3$ |
| G-13 | H | ⬠H | H | CH$_3$ | CH$_3$ | H | H | CH$_3$ | CH$_3$ |
| G-14 | H | H | H | ⬡ | CH$_3$ | H | H | CH$_3$ | CH$_3$ |
| G-15 | H | H | CH$_3$O | CH$_3$ | CH$_3$ | H | H | CH$_3$ | CH$_3$ |
| G-16 | CH$_3$H | H | H | H | ⬡H (Condensation) | H | H | H | H |
| G-17 | H | CH$_3$SO$_2$NH | H | CH$_3$ | CH$_3$ | H | H | CH$_3$ | CH$_3$ |
| G-18 | H | CH$_3$CO | H | CH$_3$ | CH$_3$ | H | H | CH$_3$ | CH$_3$ |
| G-19 | H | ⬡ | H | CH$_3$ | CH$_3$ | H | H | CH$_3$ | CH$_3$ |
| G-20 | H | ⬡-CH$_2$- | H | CH$_3$ | CH$_3$ | H | H | CH$_3$ | CH$_3$ |
| G-21 | H | ⬠H | (Condensation) | H | H | H | H | H | H |
| G-22 | H | (substituted cyclopentane) | (Condensation) | CH$_3$ | CH$_3$ | H | H | CH$_3$ | CH$_3$ |
| G-23 | H | ⬡H | (Condensation) | CH$_3$ | CH$_3$ | H | H | CH$_3$ | CH$_3$ |
| G-24 | CH$_3$ | (substituted cyclopentane) | (Condensation) | CH$_3$ | CH$_3$ | H | H | CH$_3$ | CH$_3$ |

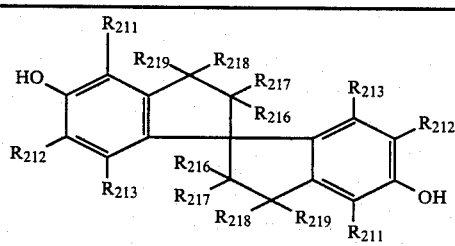

| Compound No. | R$_{211}$ | R$_{212}$ | R$_{213}$ | R$_{216}$ | R$_{217}$ | R$_{218}$ | R$_{219}$ |
|---|---|---|---|---|---|---|---|
| G-29 | H | H | H | H | H | CH$_3$ | CH$_3$ |

-continued

| | | | | | | | |
|---|---|---|---|---|---|---|---|
| G-32 | CH$_3$ | H | H | H | H | CH$_3$ | CH$_3$ |

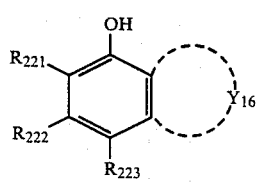

General formula [H]

115

In this formula, $R_{221}$ and $R_{222}$ respectively express a hydrogen atom, a halogen atom, an alkyl group, an alkenyl group, an aryl group, an acyl group, an acylamino group, an acyloxy group, a sulfonamido group, a cycloalkyl group, or an alkoxycarbonyl group.

$R_{223}$ expresses a hydrogen atom, a halgen atom, an alkyl group, an alkenyl group, an alkoxy group, a hydroxy group, an aryl group, an aryloxy group, an acyl group, an acylamino group, an acyloxy group, a sulfonamido group, a cycloalkyl group, or an alkoxycarbonyl group.

The groups given above may respectively be substituted with other substituents, of which such examples as an alkyl group, an alkenyl group, an alkoxy group, an aryl group, an aryloxy group, a hydroxy group, an alkoxycarbonyl group, an aryloxycarbonyl group, an acylamino group, a carbamoyl group, a sulfonamido group, and a sulfamoyl group can be mentioned.

Furthermore, $R_{221}$ and $R_{222}$, as well as $R_{222}$ and $R_{223}$, may make a closed ring with each other, thereby forming a five- to six-membered hydrocarbon ring. The said hydrocarbon ring may be substituted with a halogen atom, an alkyl group, a cycloakyl group, an alkoxy group, an alkenyl group, a hydroxy group, an aryl group, an aryloxy group, a heterocyclic group, and so forth.

$Y_{16}$ expresses a group of atoms necessary for the formation of an indan ring, and the indan ring may be substituted with a substituent which can substitute itself for the above-mentioned hydrocarbon ring, and it may also form a spiro ring.

Of the compounds expressed by the general formula [H], those compouds which are specially useful for the present invention are included in the compounds expressed by the general formula [H-1]~[H-2].

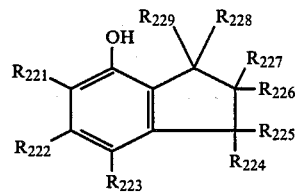

General formula [H-1]

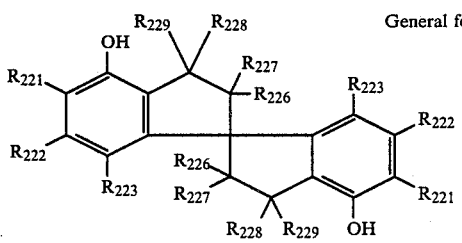

General formula [H-2]

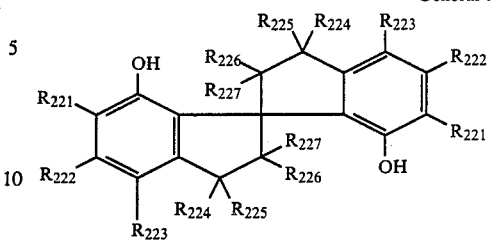

General formula [H-3]

$R_{221}$, $R_{222}$, and $R_{223}$ in the general formulae [H-1]~[H-3] are synonymous with those in the general formula [H], and $R_{224}$, $R_{225}$, $R_{226}$, $R_{227}$, $R_{228}$, and $R_{229}$ respectively represent a hydrogen atom, a halogen atom, an alkyl group, an alkoxy group, a hydroxy group, an alkenyl group, an aryl group, an aryloxy group, or a heterocyclic group. Moreover, $R_{224}$ and $R_{225}$, $R_{225}$ and $R_{226}$, $R_{226}$ and $R_{227}$, $R_{227}$ and $R_{228}$, and $R_{228}$ and $R_{229}$ may make a closed ring with each other, thereby forming a hydrocarbon ring, and the hydrocarbon ring may, moreover, be substituted with an alkyl group.

In the general formula [H-1]~[H-3] mentioned above, those compounds which have a hydrogen atom, an alkyl group, or a cycroalkyl group for $R_{221}$ and $R_{222}$, respectively, a hydrogen atom, an alkyl group, an alkoxy group, a hydroxy group, or a cycloalkyl group for $R_{223}$, and a hydrogen atom, an alkyl group, or a cycloalkyl group for $R_{224}$, $R_{225}$, $R_{226}$, $R_{227}$, $R_{228}$, and $R_{229}$ respectively are specially useful.

The method of synthesis of the compounds expressed by the general formula [H] mentioned above is already known, and such compounds can be manufactured in accordance with U.S. Pat. No. 3,057,927, Chem. Ber., 1972, 95(5), pp. 1673~1674, and Chemistry Letter, 1980, pp. 739~742.

The compounds expressed by the general formula [H] mentioned above is to be used in the amount preferably 5~300 mol %, and more preferably of 10~200 mol %, for the magenta coupler.

In the following part, concrete representative examples are presented for the compounds expressed by the general formula [H].

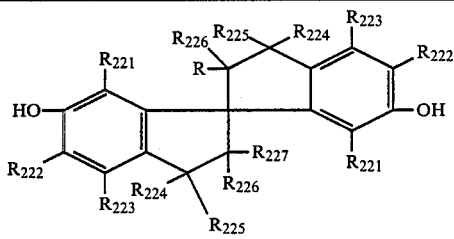

| Compound No. | $R_{221}$ | $R_{222}$ | $R_{223}$ | $R_{224}$ | $R_{225}$ | $R_{226}$ | $R_{227}$ |
|---|---|---|---|---|---|---|---|
| G-25 | H | CH$_3$ | H | CH$_3$ | C$_6$H$_5$ | H | H |

-continued

| | | | | | | | |
|---|---|---|---|---|---|---|---|
| G-26 | Cl | Cl | H | $CH_3$ | $CH_3$ | H | H |
| G-27 | H | OH | H | $CH_3$ | $CH_3$ | H | H |
| G-28 | H | $C_3H_7$ | H | $CH_3$ | $CH_3$ | H | H |
| G-30 | H | Cl | H | $CH_3$ | $CH_3$ | H | H |
| G-31 | H | $C_2H_5$ | H | $CH_3$ | $CH_3$ | H | H |
| G-33 | $CH_3$ | $CH_3$ | H | $CH_3$ | $CH_3$ | H | H |
| G-34 | H | ⬠H | H | $CH_3$ | $CH_3$ | H | H |
| G-35 | H | $CH_3$ | H | H | H | H | H |
| G-36 | H | H | H | ⬡H (Spiro) | | H | H |
| G-37 | $CH_3$ | H | H | $CH_3$ | $CH_3$ | H | H |
| G-38 | H | $CH_3$ | H | $CH_3$ | $C_2H_5$ | H | H |
| G-39 | ⬠H | H | H | $CH_3$ | $CH_3$ | H | H |
| G-40 | $CH_3$ | $CH_3$ | H | $C_2H_5$ | $C_2H_5$ | H | H |
| G-41 | H | H | H | H | H | $CH_3$ | $CH_3$ |
| G-42 | H | OH | H | ⬡H (Spiro) | | H | H |
| G-43 | H | Ph-$CH_2-$ | H | H | H | H | H |
| G-44 | H | (t)$C_4H_9$ | H | $CH_3$ | $CH_3$ | H | H |
| G-45 | H | (t)$C_8H_{17}$ | H | $CH_3$ | $CH_3$ | H | H |

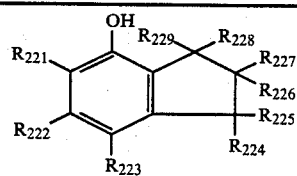

| Compound No. | $R_{221}$ | $R_{222}$ | $R_{223}$ | $R_{224}$ | $R_{225}$ | $R_{226}$ | $R_{227}$ | $R_{228}$ | $R_{229}$ |
|---|---|---|---|---|---|---|---|---|---|
| H-1 | H | H | H | H | H | H | H | H | H |
| 2 | $CH_3$ | H | H | H | H | H | H | H | H |
| 3 | H | H | H | H | H | H | H | $CH_3$ | $C_{16}H_{33}$ |
| 4 | H | H | OH | H | H | H | H | H | H |
| 5 | $CH_2=CHCH_2$ | H | Cl | H | H | H | H | H | H |
| 6 | H | H | H | H | H | H | H | $CH_3$ | $CH_3$ |
| 7 | H | H | H | $CH_3$ | $CH_3$ | H | H | H | H |
| 8 | H | H | H | $CH_3$ | $CH_3$ | $CH_3$ | H | H | H |
| 9 | $CH_2=CHCH_2$ | H | $CH_3O$ | H | H | H | H | H | H |
| 10 | H | H | H | $CH_3$ | $CH_3$ | H | H | $CH_3$ | $CH_3$ |
| 11 | H | $C_3H_7$ | H | $CH_3$ | $CH_3$ | H | H | $CH_3$ | $CH_3$ |
| 12 | Cl | H | Cl | H | H | H | H | $CH_3$ | $CH_3$ |
| H-13 | H | H | H | H | ⬡H (Condensation) | | H | H | H |
| 14 | H | H | H | H | H | H | H | ⬠H (Spiro) | |

-continued

| | | | | | | | | | |
|---|---|---|---|---|---|---|---|---|---|
| 15 | H | cyclopentyl(H) | H | $CH_3$ | $CH_3$ | H | H | $CH_3$ | $CH_3$ |
| 16 | H | $CH_3SO_2NH$ | H | $CH_3$ | $CH_3$ | H | H | $CH_3$ | $CH_3$ |
| 17 | H | $CH_3CO$ | H | H | H | H | H | $CH_3$ | $CH_3$ |
| 18 | H | phenyl | H | $CH_3$ | $CH_3$ | H | H | $CH_3$ | $CH_3$ |
| 19 | H | benzyl ($-CH_2-C_6H_5$) | H | $CH_3$ | $CH_3$ | H | H | $CH_3$ | $CH_3$ |
| 21 | | cyclohexyl(H) | $CH_3$ | H | H | H | H | $CH_3$ | $CH_3$ |
| 22 | H | H | H | $CH_3$ | phenyl | H | H | $CH_3$ | $CH_3$ |

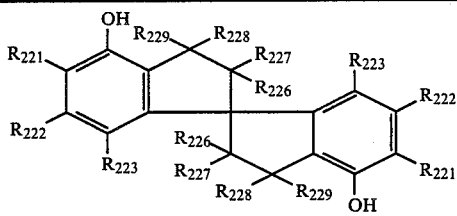

| Compound No. | $R_{221}$ | $R_{222}$ | $R_{223}$ | $R_{226}$ | $R_{227}$ | $R_{228}$ | $R_{229}$ |
|---|---|---|---|---|---|---|---|
| H-23 | H | H | H | H | H | H | H |
| 24 | H | H | OH | H | H | H | H |
| 25 | $CH_3$ | H | $CH_3$ | H | H | H | H |
| 26 | H | H | $CH_3$ | H | H | H | H |
| 27 | Cl | H | Cl | H | H | $CH_3$ | $CH_3$ |
| 28 | H | H | H | H | H | H | cyclohexyl(Spiro) |
| 29 | H | H | H | H | H | $CH_3$ | phenyl |
| 30 | H | H | cyclopentyl(H) | H | H | H | H |
| 31 | H | H | benzyl ($-CH_2-C_6H_5$) | H | H | $CH_3$ | $CH_3$ |
| 36 | H | H | $(t)C_4H_9$ | H | H | $CH_3$ | $CH_3$ |

| Compound No. | $R_{221}$ | $R_{222}$ | $R_{223}$ | $R_{224}$ | $R_{225}$ | $R_{226}$ | $R_{227}$ |
|---|---|---|---|---|---|---|---|
| H-32 | H | H | H | H | H | H | H |
| 33 | H | H | H | $CH_3$ | $CH_3$ | H | H |
| 34 | H | H | $(t)C_4H_9$ | $CH_3$ | $CH_3$ | H | H |
| 35 | H | H | $(t)C_8H_{17}$ | $CH_3$ | $CH_3$ | H | H |

Others
H-20

General formula [J]

[In this formula, $R_{231}$ expresses an aliphatic group, a cycloalkyl group, or an aryl group, an $Y_{17}$ expresses a group of nonmetal atoms necessary, together with a nitrogen atom, for the formation of a five- to seven-membered ring. However, in case there are two or more hetero-atoms among the nonmetal atoms, including a nitrogen atoms, which form the heterocycle, at least two hetero-atoms are such hetero-atoms as are not adjacent to each other.]

As the aliphatic group expressed by $R_{231}$, a saturated alkyl group which may have a substituent and an unsaturated alkyl group which may have a substituent can be cited. As the saturated alkyl groups, a methyl gruop, an ethyl group, a butyl group, an octyl group, a dodecyl group, a tetradecyl group, a hexadecyl group, etc., for example, can be mentioned, and, as the unsaturated alkyl groups, an ethenyl group, a propenyl group, etc., for example, can be cited.

As the cycloalkyl group expressed by $R_{231}$, a cyclopentyl group, a cyclohexyl group, etc., for example, i.e. five- to seven-membered cycloalkyl groups, that may have a substituent, may be cited.

The aryl group indicated by $R_{231}$ expresses a phenyl group and a naphthyl group, which may respectively have a substituent.

As the substituents for the aliphatic group, the cycloalkyl group, and the aryl group, which are expressed by $R_{231}$, an alkyl group, an aryl group, an alkoxy group, a carbonyl group, a carbamoyl group, an acylamino group, a sulfamoyl group, a sulfonamido group, a carbonyloxy group, an alkylsulfonyl group, an arylsulfonyl group, a hydroxy group, a heterocyclic group, an alkylthio group, an arylthio group, and so forth can be mentioned, and these substituents may further have substituents.

In the general formula [J] mentioned above, Y expresses a group of nonmetal atoms necessary for the formation of a five- to seven-membered heterocycle together with a nitrogen atom, and yet at least two out of the nonmetal atoms in the group including the nitrogen atom which forms the heterocycle should be hetero-atoms, and also these hetero-atoms at least two in number must not be adjacent to each other. In the heterocycle of the compound expressed by the general formula [J], any positioning of all the hetero-atoms adjacent to each other is undesirable because it makes it impossible for the compound to display its function as the stabilizing agent for the magentacolored picture.

The five- to seven-membered heterocycle for the compound expressed by the general formula [J] mentioned above may have a substituent, and the substituents are an alkyl group, an aryl group, an acyl group, a carbamoyl group, an alkoxycarbamoyl group, a sulfonyl group, a sulfamoyl group, etc., and may further have a substituent. Moreover, the five- to seven-membered heterocycle may be a saturated one, and yet a saturated heterocycle is preferable. Also, the heterocycle may have a benzene ring, etc. condensed to it and may form a spiro ring.

The amount used of the compound expressed by the above-mentioned general formula [J] for the present invention is preferably 5~300 mol %, and more preferably 10~200 mol %, for the magenta coupler which is expressed by the general formula [I] for the present invention.

In the following part are given representative specific examples of the compounds which are expressed by the general formula [J].

| | $R_{232}$ | $R_{233}$ | $R_{234}$ | $R_{235}$ | $R_{236}$ | $R_{237}$ | $R_{238}$ | $R_{239}$ | $R_{240}$ | $R_{241}$ |
|---|---|---|---|---|---|---|---|---|---|---|
| J-1 | $C_{12}H_{25}$ | $C_{12}H_{25}$ | H | H | H | H | H | H | H | H |
| J-2 | $C_{14}H_{29}$ | $C_{14}H_{29}$ | H | H | H | H | H | H | H | H |
| J-3 | $C_{14}H_{29}$ | H | H | H | H | H | H | H | H | H |
| J-4 | $C_{14}H_{29}$ | $CH_3CO$ | H | H | H | H | H | H | H | H |
| J-5 | $C_{16}H_{33}$ | $C_{16}H_{33}$ | H | H | H | H | H | H | H | H |
| J-6 | $C_{14}H_{29}$ | $CH_3$ | H | H | H | H | H | H | H | H |

-continued

| | | | | | | | | | | | |
|---|---|---|---|---|---|---|---|---|---|---|---|
| J-7 | ⌬—CH₂ | | ⌬—CH₂ | H | H | H | H | H | H | H | H |
| J-8 | ⌬ | | ⌬ | H | H | H | H | H | H | H | H |
| J-11 | CH₃ | | —CH₂O—⌬(C₅H₁₁(t))—C₅H₁₁(t) | H | H | H | H | H | H | H | H |
| J-13 | C₁₄H₂₉ | | C₄H₉NHCO | H | H | H | H | H | H | H | H |
| J-14 | (t)C₈H₁₇ | | ⌬—CH₂ | H | H | H | H | H | H | H | H |
| J-15 | C₁₄H₂₉ | | CF₃CO | H | H | H | H | H | H | H | H |
| J-16 | C₁₄H₂₉ | | C₂H₅OCO | H | H | H | H | H | H | H | H |
| J-17 | CH₃ | | —COCHO—⌬(C₅H₁₁(t))—C₅H₁₁(t), C₂H₅ | H | H | H | H | H | H | H | H |
| J-18 | C₁₄H₂₉ | | C₁₄H₂₉ | CH₃ | H | H | H | H | H | H | H |
| J-19 | C₁₄H₂₉ | | C₁₄H₂₉ | CH₃ | H | H | H | H | H | CH₃ | H |
| J-20 | C₁₄H₂₉ | | C₁₄H₂₉ | CH₃ | CH₃ | CH₃ | CH₃ | CH₃ | CH₃ | CH₃ | CH₃ |
| J-21 | CH₃ | | —(CH₂)₂—⌬—NHCOCHO—⌬(C₅H₁₁(t))—C₅H₁₁(t), C₄H₉ | H | H | H | H | H | H | H | H |
| J-22 | C₁₂H₂₅ | | CH₃ | CH₃ | H | H | H | CH₃ | H | H | H |
| J-23 | C₁₂H₂₅ | | C₁₂H₂₅ | CH₃ | H | H | H | H | H | CH₃ | H |
| J-24 | C₁₆H₃₃ | | C₁₆H₃₃ | CH₃ | H | H | H | H | H | CH₃ | H |
| J-25 | C₂H₅CH=CH—CH₂— | | C₁₂H₂₅ | H | H | H | H | H | H | H | H |
| J-26 | C₁₂H₂₅ | | C₂H₅ | CH₃ | H | H | H | H | H | H | H |
| J-27 | C₁₆H₃₃ | | H | C₂H₅ | H | H | H | H | H | H | H |
| J-29 | C₁₄H₂₉ | | CH₂BrCH₂ | H | H | H | H | H | H | H | H |
| J-30 | CH₃O(CH₂)₄— | | CH₃O(CH₂)₄ | H | H | H | H | H | H | H | H |

R₂₃₂—N⌬N—R₂₃₃—N⌬N—R₂₃₄

| | R₂₃₂ | R₂₃₃ | R₂₃₄ |
|---|---|---|---|
| J-9 | C₁₄H₂₉ | (CH₂)₂ | C₁₄H₂₉ |
| J-10 | (t)C₈H₁₇ | (CH₂)₆ | (t)C₈H₁₇ |
| J-12 | C₁₄H₂₉ | CH₂ | C₁₄H₂₉ |
| J-28 | C₁₂H₂₅ | —CH₂—⌬—CH₂— | C₁₂H₂₅ |

R₂₃₁—N⌬X

| | X | R₂₃₁ |
|---|---|---|
| J-31 | O | C₁₂H₂₅ |
| J-32 | O | C₁₄H₂₉ |

-continued

| | | |
|---|---|---|
| J-33 | O | C₆H₅CH=CH— |
| J-34 | O | CH₃CONH—⌬— |
| J-35 | O | α-naphthyl |
| J-36 | O | ⌬(C₁₅H₃₁)—OCHCONH—⌬—(CH₂)₃—, C₂H₅ |
| J-37 | O | HO—⌬—SO₂—⌬—OCHCONH—⌬—(CH₂)₃ |
| J-38 | O | ⌬—SO₂NH—⌬—CH₂— |
| J-39 | O | t-C₅H₁₁—⌬(C₅H₁₁(t))—OCHCONH—(CH₂)₂—, C₂H₅ |

-continued
| | |
|---|---|
| J-40 O | 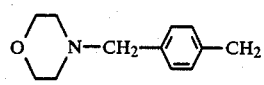 |
| J-41 S | C$_{14}$H$_{29}$ |
| J-42 S | 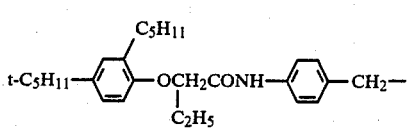 |
| J-43 S | 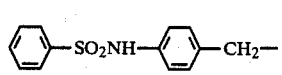 |
| J-44 S |  |
| J-45 S | 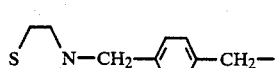 |
| | R$_{231}$ | R$_{232}$ |
|---|---|---|
| J-46 | C$_{12}$H$_{25}$ | C$_{12}$H$_{25}$ |
| J-47 | C$_{14}$H$_{29}$ | C$_{14}$H$_{29}$ |
| J-48 | C$_6$H$_5$CH$_2$ | C$_6$H$_5$CH$_2$ |
| J-49 | C$_{16}$H$_{33}$ | H |
| J-50 | C$_{16}$H$_{33}$ | CH$_3$CO |
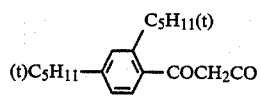
| | R$^1$ | R$^2$ |
|---|---|---|
| J-51 | C$_{16}$H$_{33}$ | C$_{16}$H$_{33}$ |
| J-52 | C$_{14}$H$_{29}$ | C$_{14}$H$_{29}$ |
| J-53 | C$_{12}$H$_{25}$ | C$_{12}$H$_{25}$ |
| J-54 | C$_{14}$H$_{29}$ | CH$_3$CO |
| J-55 | C$_{14}$H$_{29}$ | CF$_3$CO |
| J-56 | C$_2$H$_5$ | 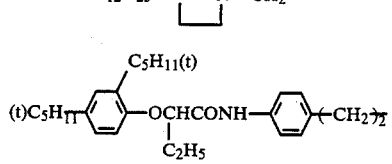 |
| J-57 | C$_{14}$H$_{29}$ | C$_2$H$_5$OCO |
| J-58 | C$_{14}$H$_{29}$ | CH$_3$NHCO |
| J-59 | C$_{14}$H$_{29}$ | C$_4$H$_9$SO$_2$ |
| J-60 | C$_{14}$H$_{29}$ | (CH$_3$)$_2$NSO$_2$ |
| J-61 | C$_{12}$H$_{25}$ | 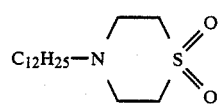 |
| J-62 | H | 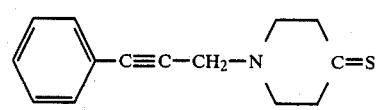 |
| | |
|---|---|
| J-63 | 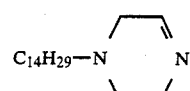 |
| J-64 | 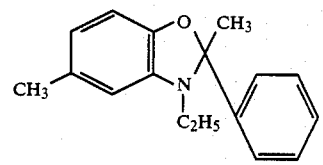 |
| J-65 | 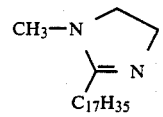 |
| J-66 | 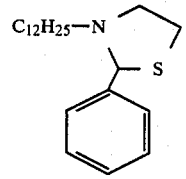 |
| J-67 | 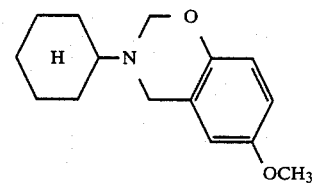 |
| J-68 | 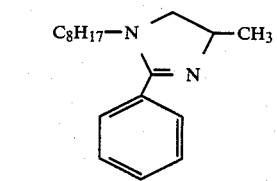 |
| J-69 | 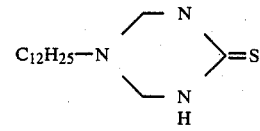 |
| J-70 | 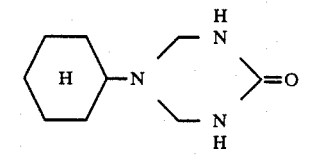 |
| J-71 | 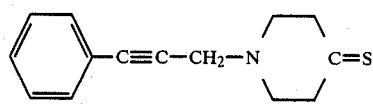 |
| J-72 | |
| J-73 | |

J-74

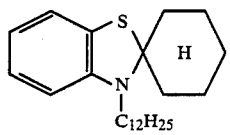

Among those compounds which are expressed in the general formula [J] mentioned above, a piperazine compound and a homopiperazine compound are specially preferable, and more preferable ones are thos compounds which are expressed by the general formula [J-1] or the general formula [J-2] given in the following:

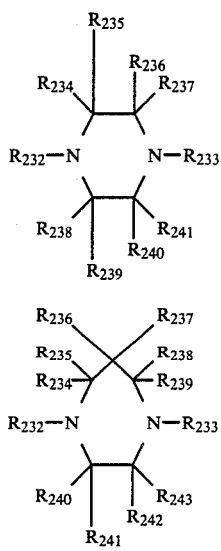

General formula [J-1]

General formula [J-2]

In these formulae, $R_{232}$ and $R_{233}$ respectively express a hydrogen atom, an alkyl group, or an aryl group. However, it does not occur that $R_{232}$ and $R_{233}$ are hydrogen atoms at the same time. $R_{234} \sim R_{243}$ respectively express an alkyl group or an aryl group.

In the general formula [J-1] and [J-2], $R_{232}$ and $R_{233}$ respectively express a hydrogen atom, an alkyl group, or an aryl group, and, as the alkyl group which is expressed by $R_{232}$ or $R_{233}$, a methyl group, an ethyl group, a butyl group, an octyl group, a dodecyl group, a tetradecyl group, a hexadecyl group, an octadecyl group, and so forth, for example, can be mentioned. As the aryl group which is expressed by $R_{232}$ or $R_{233}$, such groups as a phenyl group can be cited. The alkyl group and aryl group which are expressed by $R_{232}$ or $R_{233}$ may have substituents, and, for such substituents, a halogen atom, an alkyl group, and aryl group, an alkoxy group, an aryloxy group, a deterocyclic group and so on can be cited.

It is preferable that the sum total of the numbers of carbon atoms in $R_{232}$ (including the substituents) is in the range from 6 to 40.

In the general formula [J-1] or the general formula [J-2] mentioned above, $R_{234}$ and $R_{243}$ respectively express a hydrogen atom, an alkyl group, or an aryl group, and, as the alkyl group which is expressed by $R_{234}-R_{243}$, a methyl group, an ethyl group, and so on, for example, can be cited. As the aryl group which is expressed by $R_{234} \sim R_{243}$, a phenyl group, etc. can be mentioned.

The concrete examples of those compounds which are expressed by the general formula [J-1] or [J-2] mentioned above are as described in the examples of piperazine compounds in (J-1) through (J-30) or in the examples of homopiperazine compounds in (J-51) through (J-62).

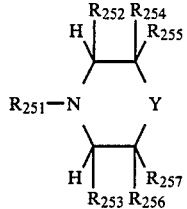

General formula [K]

In this formula, $R_{251}$ expresses an aliphatic group, a cycloalkyl group, or an aryl group, and Y expresses a mere bond necessary for forming a five- to seven-membered heterocycle, together with a nitrogen atom, or a bivalent hydrocarbon group. $R_{252}$, $R_{253}$, $R_{254}$, $R_{255}$, $R_{256}$, and $R_{257}$ respectively express a hydrogen atom, an aliphatic group, a cycloalkyl group, or an aryl group. However, $R_{252}$ and $R_{254}$, and $R_{253}$ and $R_{256}$ may form an unsaturated five- to seven-membered ring together with a nitrogen atom and Y, forming a mere bond by bonding with each other. Moreover, in case Y works as a mere coupler, $R_{255}$ and $R_{257}$ may form an unsaturated five-membered ring, together with Y, forming a mere bond by bonding with each other. Furthermore, in case Y is not a mere coupler, $R_{255}$ and Y, $R_{257}$ and Y, or Y and Y itself may form an unsaturated bond to form an unsaturated six- or seven-membered heterocycle, together with a nitrogen atom and Y.

As the aliphatic group expressed by $R_{251}$, a saturated alkyl group which may have a substituent and an unsaturated alkyl group which may have a substituent may be cited. As the saturated alkyl group, a methyl group, an ethyl group, a butyl group, an octyl group, a dodecyl grup, a tetradecyl group, a hexadecyl group, and so forth, for example, can be cited, and as the unsaturated alkyl group, an ethenyl group, a propenyl group, etc., for example, can be cited.

As the cycloalkyl group expressed by $R_{251}$, which is a five- to seven-membered cycloalkyl group that may ahve a substituent, such groups as a cyclopentyl group and a cyclohexyl group, for example, can be cited.

The aryl groups expressed by $R_{251}$ are a phenyl group and a naphthyl group which may have a substituent.

As the substituents for the aliphatic group, cycloalkyl group, and aryl group which are expressed by $R_{251}$, and alkyl group, an aryl group, an alkoxy group, a carbonyl group, a carbamoyl group, an acylamino group, a sulfamoyl group, a sulfonamido group, a carbonyloxy group, an alkylsulfonyl group, an arylsulfonyl group, a hydroxy group, a heterocyclic group, an alkylthio group, an arylthio group, and so forth can be cited, and these substituents may fruther have substituents.

In the general formula [K] mentioned above, Y expresses a mere bond, or a bivalent hydrocarbon group, which is necessary for the formation of a five- ro seven-membered heterocycle together with a nitrogen atom, and, in case Y is a mere bond, $R_{255}$ and $R_{257}$ may further form a bond with each other to make a mere bond, therewith forming an unsaturated five-membered heterocycle. Moreover, in case y is a bivalent hydrocarbon group, i.e. in case it is a methylene group, $R_{255}$ and Y or $R_{257}$ and Y may form an unsaturated bond with each other, thereby forming an unsaturated six-membered heterocycle, and, in the case of an ethylene group, $R_{255}$ and Y, $R_{257}$ and Y, or Y and Y itself may form an unsaturated bond, thereby forming an unsaturatedrated six-membered heterocycle, and, in the case of an ethylene group, $R_{255}$ and Y, $R_{257}$ and Y, or Y and Y itself may form an unsaturated bond, thereby forming an unsaturated seven-membered heterocycle. Moreover, the bivalent hydrocarbon group which is expressed by Y may have a substituent, for which an alkyl group, a carbamoyl group, an alkyloxycarbonyl group, an acylamino group, a sulfonamido group, a sulfamoyl group, an aryl group, a heterocyclic group, and so forth can be cited.

In the general formula [K] given above, $R_{252}$, $R_{253}$, $R_{254}$, $R_{256}$, and $R_{257}$ respectively express a hydrogen atom, an aliphatic group, a cycloalkyl gruop, or an aryl group, and, as the aliphatic groups which are expressed by $R_{252} \sim R_{257}$, an alkyl group which may have a substituent and an unsaturated hydrocarbon group which may have a substituent can be mentioend. As the alkyl groups, a methyl group, an ethyl group, a butyl group, an octyl group, a dodecyl group, a tetradecyl group, a hexadecyl group, and so forth, for example, can be cited, and, as the unsaturated hydrocarbon groups, an ethenyl group, a propenyl group, etc., for example, can be cited.

The cycloalkyl groups which are expressed by $R_{252} \sim R_{257}$ are five- to seven-membered cycloalky groups which may have substituents, and, as such groups, a cyclopentyl group, a cyclohexyl group, and so forth may be cited.

As the aryl groups which are expressed by $R_{252} \sim R_{257}$, a phenyl group, a nathphy group, etc. which may have substituents can be mentioned.

As the substituents for the aliphatic group, a cycloalkyl group, and aryl group which are expressed by $R_{252} \sim R_{257}$ given above, an alkyl group, an aryl group, an alkoxy group, a carbonyl group, a carbamoyl group, an acylamino group, an sulfamoyl group, a sulfonamide group, a carbonyloxy group, an alkylsulfonyl group, an arylsulfonyl group, a hydroxy group, a heterocyclic group, an alkylthio group, and so forth can be mentioned.

For the compounds which are expressed by the above-mentioned general formula [K], the case in which such a compound has a saturagted heterocycle with five- to seven-members is more preferable than such a compound with an unsaturated heterocycle.

The amount used of the compound which is expressed by the general formula [K] given above is preferably $5 \sim 300$ mol %, and more preferably $10 \sim 200$ mol %, for the magenta coupler of the present invention as expressed in the general formula [I] given above.

In the following part, representative concrete examples of the compounds expressed by the above-mentioned general formula [K] are presented.

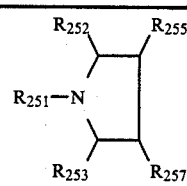

| | $R_{251}$ | $R_{252}$ | $R_{255}$ | $R_{257}$ | $R_{253}$ |
|---|---|---|---|---|---|
| K-1 | $C_8H_{17}$ | H | H | H | H |
| K-2 | CH$_3$CONH—⟨phenyl⟩— | H | H | H | H |
| K-3 | pyrrolidino-CH$_2$—⟨2,5-dihydroxyphenyl⟩—CH$_2$— | H | H | H | H |
| K-4 | $C_{12}H_{25}$ | H | H | H | H |
| K-5 | $C_{14}H_{29}$ | H | H | H | H |
| K-6 | $C_{16}H_{33}$ | H | H | H | H |
| K-7 | $C_{14}H_{29}$ | H | $C_{14}H_{29}$—N⟨ring⟩—(CH$_2$)$_2$— | H | H |
| K-8 | ⟨cyclohexyl-H⟩ | CH$_3$ | CH$_3$ | H | H |
| K-9 | $C_6H_5CH=CHCH_2$— | H | H | H | H |

-continued
| | | | | | | |
|---|---|---|---|---|---|---|
| K-10 | 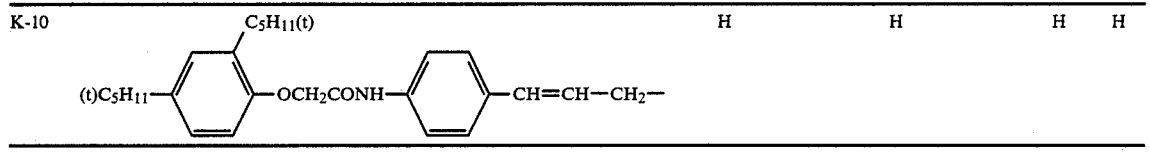 | | H | H | H | H |
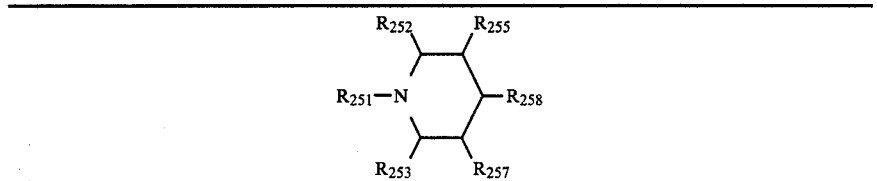
| | $R_{251}$ | $R_{252}$ | $R_{255}$ | $R_{258}$ | $R_{257}$ | $R_{253}$ |
|---|---|---|---|---|---|---|
| K-11 | (t)C$_8$H$_{17}$ | H | H | H | H | H |
| K-12 |  | H | H | H | H | H |
| K-13 | C$_{12}$H$_{25}$ | H | H | H | H | H |
| K-14 | C$_{14}$H$_{29}$ | H | H | H | H | H |
| K-15 | C$_{16}$H$_{33}$ | H | H | H | H | H |
| K-16 | C$_{14}$H$_{29}$ | CH$_3$ | H | H | H | H |
| K-17 | 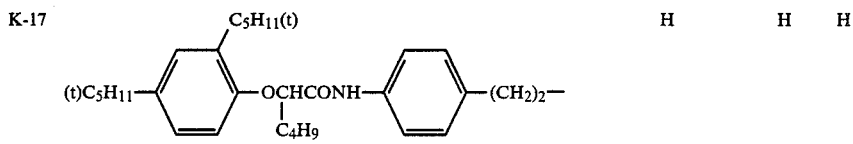 | | H | H | H | H |
| K-18 | C$_8$H$_{17}$ | CH$_3$ | CH$_3$ | H | CH$_3$ | CH$_3$ |
| K-19 | 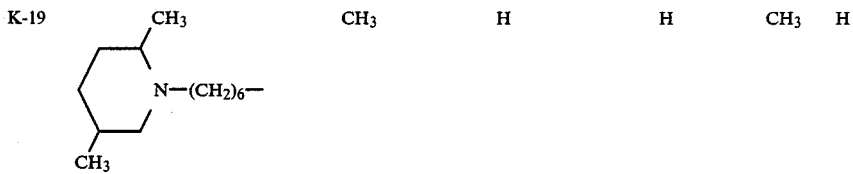 | CH$_3$ | H | H | CH$_3$ | H |
| K-20 | CH$_3$ | H | H | C$_{12}$H$_{25}$OCOCH$_2$— | H | H |
| K-21 | CH$_3$ | CH$_3$ | H | C$_{16}$H$_{33}$OCOCH$_2$— | H | CH$_3$ |
| K-22 | CH$_3$ | C$_{16}$H$_{33}$ | H | H | H | H |
| K-23 | C$_2$H$_5$ | H | H | C$_{12}$H$_{25}$OCO— | H | H |
| K-24 | CH$_3$ | C$_2$H$_5$ | H | H | H | H |
| K-25 |  | H | H | H | H | H |
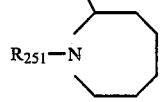
| | $R_{251}$ | $R_{252}$ |
|---|---|---|
| K-26 | C$_8$H$_{17}$ | H |
-continued
| | | |
|---|---|---|
| K-27 | 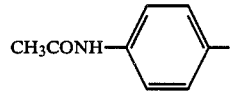 | H |
| K-28 | 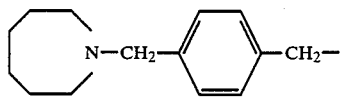 | H |
| K-29 | C$_{14}$H$_{29}$ | H |

-continued

| | | |
|---|---|---|
| K-30 | 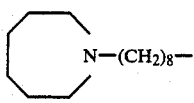 | H |
| K-31 | $C_{16}H_{33}$ | $CH_3$ |
| K-32 |  | H |
| K-33 | 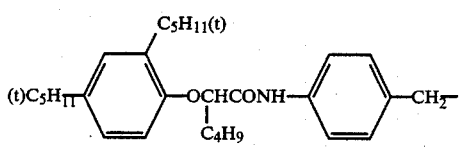 | H |

K-34
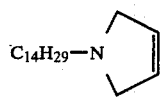

K-35
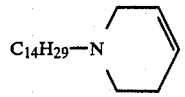

K-36
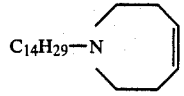

K-37
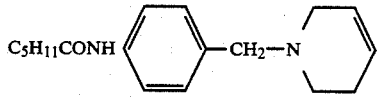

K-38
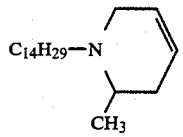

K-39
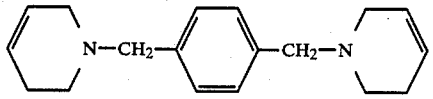

K-40
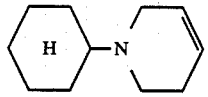

K-41
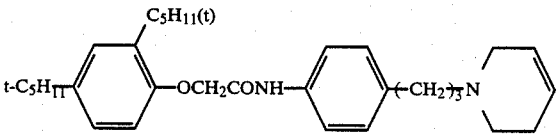

Silver halide photosensitive materials for photography can, for example, be negative and positive color films, photographic color printing paper, and so on. However, the effect of the present invention can be displayed effectively particularly in the use of photographic color printing paper, which is used directly for the appreciation with specially frequent exposures to light.

For the silver halide emulsion used for the silver halide photosensitive material for photography, any voluntarily selected silver halide emulsion, such as silver bromide, silver iodo bromide, silver iodochloride, silver chlorobromide, silver chloride, etc., which are used for the ordinary silver halide emulsion.

The silver halide particles used for the silver halide emulsion may be such particles as have a latent image formed primarily on their surface.

The silver halide emulsion is chemically sensitized by an ordinary manner.

The silver halide emulsion can be optically sensitized to the desired wave-length region by the use of those coloring matters known as sensitizing dye. Such sensitizing dyes may be used independently, or they may be used in a combination of two or more varieties. Together with a sensitizing dye, a coloring matter which does not have any spectral sensitizing effect in itself, or a color-reinforcing sensitizer which is a compound that actually does not absorb any visible light and yet strengthens the sensitizing effect of a sensitizing dye may be contained in the emulsion as a supersensitizer.

An ultraviolet ray absorbing agent may be contained in such hydrophilic colloid layers as the protective layer or the intermediate layer of the photosensitive material, for the purpose of preventing the fogging resulting from the electric discharge caused by the static electricity charge in the photosensitive material because of friction, etc. and preventing the picture from suffering its deterioration by the effect of the ultraviolet rays.

The photosensitive material in which silver halide emulsion is used may contain such auxiliary layers as a filter layer, a halation-preventing layer, and/or an irradiation-preventing layer can be provided.

An agent whose purpose is to prevent static electricity from charging may be added to the photosensitive material in which silver halide emulsion is used.

The silver halide photosensitive material for photography is capable of forming a picture by performing such color-development as is publicly known to this industry.

After the color-developing process is completed, the photosensitive material is treated with a processing solution which has a fixing ability, but, in case the processing solution having a fixing ability is a fixing solution, a bleaching treatment is performed before it.

EXAMPLES

In the subsequent part are given concrete examples, with reference to which the present invention is described in further detail. The manners in which the present invention is to be embodied, however, shall not be hereby limited.

Example 1

Organic coloring matter compound having the structure given below

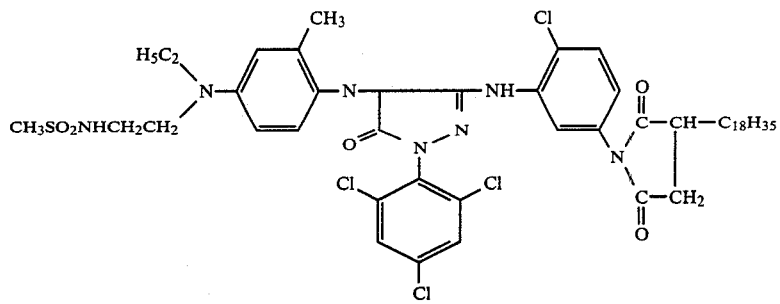

(Absorption maximum in methanol: 538 nm)

0.2 g of this compound was dissolved in 5 ml of dioctylphthalate and 10 ml of ethyl acetate. The resulting solution was dispersed in 10 ml of 10% aqueous solution of gelatin, and was then coated on a support made of polyethylene-coated paper in such a way that the amount of coating of the coloring matter attained 7 mg/dm².

The sample thus prepared was taken as Sample 1 (Reference).

Next, Sample 2 through 4, which were identical with Sample 1 except for the addition of 0.1 g of the metallic complex relevant to the present invention at the time of the emulsification and dispersion in the preparation of Sample 1, and Sample 5, which was identical with Sample 1 except for the addition of 0.1 g of 2,5-di-tert-octylhydroquinone, an anti-fading agent for reference, were prepared.

These Samples 1 through 5 were exposed to the sun light for a period of 40 days by means of an underglass outdoor exposure table, when the color light was measured with green light before and after the fading of color. The results are presented in Table 1.

TABLE 1

| Sample No. | Anti-fading agent | Density before Fading | Density after Fading |
|---|---|---|---|
| 1. (Reference) | — | 0.99 | 0.04 |
| 2. (This invention) | 4 | 0.98 | 0.57 |
| 3. (This invention) | 14 | 0.97 | 0.63 |
| 4. (This invention) | 15 | 0.99 | 0.68 |
| 5. (Reference) | Anti-fading agent for reference | 1.02 | 0.12 |

The results presented in Table 1 reveal that the conventional anti-fading agent produces a moderate effect though it is insufficient, but that the metallic complex of the present invention, in contrast to the former, is superior as it achieves a far greater effect in the prevention of color-fading under light.

Example 2

Sample 6, which was identical with Sample 1 except for the fact that the organic coloring matter compound mentioned below was coated, instead of the organic coloring matter compound on Sample 1, in such a way that the compound so coated attained 7 mg/dm², was prepared.

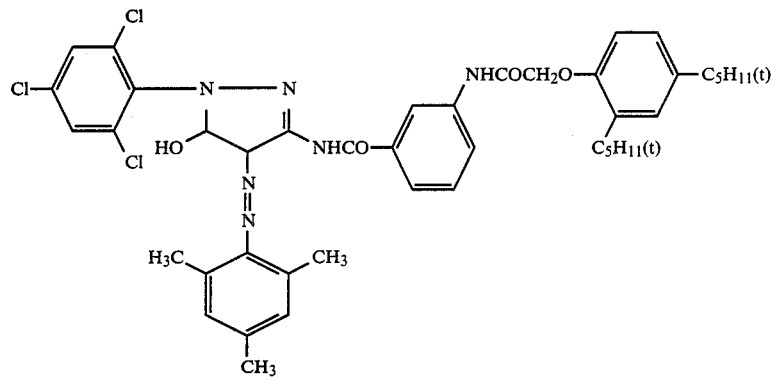

Furthermore, Sample 7 through 10, which were identical with Sample 6 except for the fact that the metallic complex relevant to the present invention, or the antioxidant for reference, i.e. 2,5-di-tert-octyl hydroquinone, was added in the amount of 0.1 g to each at the time of the dispersion in the preparation of Sample 6.

These Sample 6 through 10 were tested in the same manner as in Example 1 to determine their light-resistance.

The degree of color-fading by light (fading rate) was obtained in the manner described below, and the results are shown in Table 2.

$$\text{Fading rate} = \frac{Do - D}{Do} \times 100\ (\%)$$

Where,
Do = Density before fading by light
D = Density after facing by light

TABLE 2

| Sample No. | Anti-fading agent | Fading ratio (%) |
|---|---|---|
| 6 (Reference) | — | 98 |
| 7 (This invention) | 4 | 54 |
| 8 (This invention) | 14 | 51 |
| 9 (This invention) | 15 | 50 |

TABLE 2-continued

| Sample No. | Anti-fading agent | Fading ratio (%) |
|---|---|---|
| 10 (Reference) | Anti-fading agent for reference. | 91 |

As it is evident in Table 2, it is observed that the sample in which the metallic complex of the present invention was used suffered less color-fading under light.

Example 3

On a support made of polyethylene-coated paper were coated the magenta coupler MC-1 cited as example amounting to 4 mg/dm$^2$, green-sensitive silver chlorobromide emulsion amounting to 2 mg/dm$^2$ as converted into silver, dioctylphthalate amounting to 4 mg/dm$^2$, and gelatin amounting to 16 mg/dm$^2$, respectively in terms of the coated amount.

In a layer over it, moreover, gelatin was coated in such a way as to attain 9 mg/dm$^2$ in the coated amount.

The sample prepared in this manner was taken as Sample 11 (reference).

Then, Samples 12 through 24, which were identical with Sample 11 except for the fact that the combination of the coupler and the metallic complex was changed as shown in Table 3 in respect of the coupler-containing layer Sample 11 mentioned above, were prepared. In this regard the metallic complex was added to the solvent, together with the coupler. After wedgewise exposure in green-colored light was given to these samples by the use of an actinometer (Model KS-7 made by Konishiroku Photo Industry Co., Ltd.), the treatment described in the following was given:

| Standard Work-Processes for Treatment | | |
|---|---|---|
| (Processing temperature and processing time) | | |
| [1] Color development | 38° C. | 3 min. 30 sec. |
| [2] Bleaching and fixing | 33° C. | 1 min. 30 sec. |
| [3] Washing treatment | 25~30° C. | 3 min. |
| [4] Drying | 75~80° C. | Approx. 2 min. |
| [Color-developing solution] | | |
| Benzyl alcohol | | 15 ml |
| Ethylene glycol | | 15 ml |
| Potassium sulfite | | 2.0 g |
| Sodium bromide | | 0.7 g |
| Sodium chloride | | 0.2 g |
| Sodium carbonate | | 30.0 g |
| Hydroxylamine sulfate | | 3.0 g |
| Polyphosphoric acid (TPPS) | | 2.5 g |
| 3-methyl-4-amino-N—($\beta$-methanesulfonamide ethyl)aniline sulfate | | 5.5 g |
| Fluorescent bleaching agent (4,4'-diaminostylbenzsulfonic acid derivative) | | 1.0 g |
| Potassium hydroxide | | 2.0 g |
| The total amount is to be increased to one liter with the addition of water, and the pH is to be conditioned to 10.20. | | |
| [Bleaching and fixing solution] | | |
| Tetraferric ethylenediaminetetraacetate Ammonium dihydrate | | 60 g |
| Ethylele diamine tetraacetatic acid | | 3 g |
| Ammonium thiosulfate (70% solution) | | 100 ml |
| Ammonium sulfite (40% solution) | | 27.5 ml |
| The solution is to be conditioned to pH 7.1 with potassium carbonate or glacial acetic acid and its total amount is to be increased to one liter with the addition of water. | | |

After the treatment, a light-resistance test was conducted on the prepared samples in the same manner as in Example 2. Also, measurements of the coloring density and measurements of the fog on the silver halide emulsion and yellowish coloring (staining) were made in accordance with the particulars described in the following:

[Measurement of coloring density]

The reflection spectrum in the white-color area (the unexposed area) of each sample obtained was measured by the use of color analyzer Model 607 (made by Hitachi, Ltd.).

With the reflection density of sample 11 at 440 nm taken as the standard, the difference from the reflection density as recorded at 440 nm in the sample containing each anti-fading agent was taken as the coloring density.

[Fog value]

The area with no color image on the Samples obtained was measured in terms of the green light reflection density for the magenta fog, blue light reflection density for the yellow fog, and red light reflection density for the cyan fog, and the difference from the reflection density of the support was taken as the fog value.

[Measurement of yellowish coloring]

The individual samples obtained were preserved for a period of 20 days in a thermostat kept at 80° C. and at 15% in relative humidity (RH). Before and after the preservation, measurements were made of the difference in the blue light reflection density (i.e. incremental density) in the area with no color image on each sample. The results are presented in Table 3.

TABLE 3

| Sample No. | Coupler | Maximum absorption* wave-length (nm) | Anti-fading agent** | Fading ratio (%) | Coloring density | Fog | Stain |
|---|---|---|---|---|---|---|---|
| 11 (Reference) | MC-1 | 538 | None | 90 | — | 0.04 | 0.15 |
| 12 (Reference) | " | " | Anti-fading agent for reference | 88 | +0.000 | 0.04 | 0.16 |
| 13 (Reference) | " | " | Metallic complex for reference | 56 | +0.025 | 0.15 | 0.17 |
| 14 (This invention) | " | " | Metallic complex-15 | 23 | +0.004 | 0.04 | 0.15 |
| 15 (This invention) | " | " | Metallic complex-4 | 26 | +0.004 | 0.04 | 0.14 |
| 16 (This invention) | " | " | Metallic complex-5 | 23 | +0.004 | 0.04 | 0.15 |
| 17 (Reference) | YC-1 | 435 | None | 85 | — | 0.02 | 0.03 |
| 18 (Reference) | " | " | Anti-fading agent for reference | 86 | +0.000 | 0.02 | 0.03 |
| 19 (Reference) | " | " | Metallic complex for reference | 75 | +0.026 | 0.03 | 0.05 |
| 20 (This invention) | " | " | Metallic complex-15 | 52 | +0.004 | 0.02 | 0.03 |
| 21 (Reference) | CC-1 | 640 | None | 88 | — | 0.01 | 0.01 |
| 22 (Reference) | " | " | Anti-fading agent for reference | 89 | +0.000 | 0.01 | 0.01 |
| 23 (Reference) | " | " | Metallic complex for reference | 78 | +0.024 | 0.03 | 0.02 |

TABLE 3-continued

| Sample No. | Coupler | Maximum absorption* wave-length (nm) | Anti-fading agent** | Fading ratio (%) | Coloring density | Fog | Stain |
|---|---|---|---|---|---|---|---|
| 24 (This invention) | " | " | Metallic complex-15 | 54 | +0.004 | 0.01 | 0.01 |

*This indicates the maximum absorption wave-length obtained for coloring matter from the coupler used.
**The anti-fading agent was added in the ratio of 0.5 mol for one mol of the coupler.

Anti-fading agent for reference: 2,5-di-tert-octylhydroquinone

Metallic complex for reference

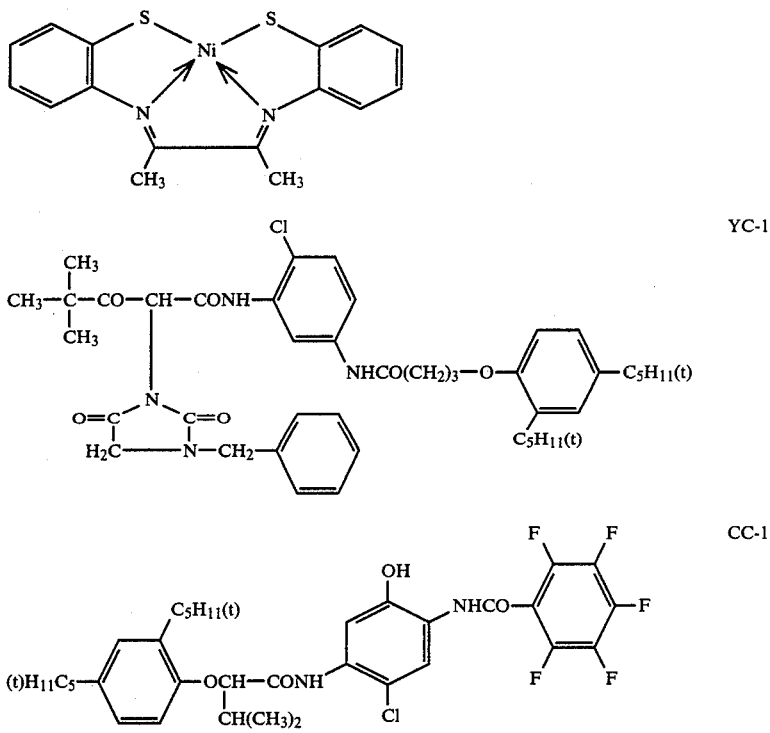

YC-1

CC-1

As it is evidently observed in Table 3, the metallic complexes of the present invention are excellent in light-resistant performance, and they leave little coloring attributable to themselves. Hence, distinct pictures could be obtained.

Example 4

On a support made of polyethylene-coated paper, the individual layers mentioned below were coated one after another in regular sequence, and silver halide photosensitive material for multichromatic photography was produced.

First Layer: Blue-sensitive sliver halide emulsion layer

As yellow coupler, α-pivalyl-α-(1-benzyl-2,4-dioxyimidalysine-3-yl)-2-chloro-5-[γ-(2,4-di-t-amylphenoxy)butylamido]-acetoanilide, amounting to 8 mg/dm$^2$, blue-sensitive silver chlorobromide emulsion amounting to 3 mg/dm$^2$ as converted into silver, 2,4-di-t-butylphenol-3',5'-di-t-amyl-4'-hydroxybenzoate amounting to 3 mg/dm$^2$, dioctylphthalate amounting to 3 mg/dm$^2$, and gelatin amounting to 16 mg/dm$^2$, each in terms of the amount of coating, were placed.

Second layer: Intermediate layer

Gelatin was coated in such a way as to attain 4 mg/dm$^2$ in the amount of coating.

Third layer: Green-sensitive silver chlorobromide emulsion layer

The magenta coupler (MC-1) cited in the example given above amounting to 4 mg/dm$^2$, green-sensitive silver chlorobromide emulsion amounting to 2 mg/dm$^2$ as converted into silver, dioctylphthalate amounting to 4 mg/dm$^2$, and gelatin amounting to 16 mg/dm$^2$, each in terms of the amount of coating, were placed.

Fourth layer: Intermediate layer

An ultraviolet absorbing agent, 2-hydroxy-3',5'-di-t-amylphenyl)-benzotriazole amounting to 3 mg/dm$^2$, 2-(2'-hydroxy-3',5'-di-t-butylphenyl)-benzotriazole amounting to 3 mg/dm$^2$, dioctylphthalate amounting to 4 mg/dm$^2$, and gelatin amounting to 14 mg/dm$^2$, each in the amount of coating, were placed.

Fifth layer: Red-sensitive silver chlorobromide emulsion layer

As cyan coupler, 2,4-dichloro-3-methyl-6-[α-(2,4-di-t-amylphenoxy)butylamide]-phenol amounting to 1 mg/dm$^2$, 2-(2-3,4,5,6-pentafluorophenyl)acylamino-4-cyloro-5-[α-(2,4-di-tert-aminophenoxy)pentylamide] amounting to 3 mg/dm$^2$, dioctylphthalate amounting to 2 mg/dm$^2$, and red-sensitive silver chlorobromide emulsion amounting to 3 mg/dm$^2$ as converted into silver, each in terms of the amount of coating, were placed.

Sixth layer: Intermediate layer

As ultraviolet absorbing agent, 2-(2'-hydroxy-3',5'-di-t-amylphenyl)-benzotriazole amounting to 2 mg/dm$^2$, 2-(2'-hydroxy-3',5'-di-t-butylphenyl)-benzotriazole amounting to 2 mg/dm², dioctylphthalate amounting to 2 mg/dm², and gelatin amounting to 6 mg/dm², each in the amount of coating, were placed.

Seventh layer: Protective layer

Gelatin was placed in such a way as to attain 9 mg/dm² in the amount of coating.

The sample which was prepared in this manner was taken as sample 25.

[Yellowish coloring (stain) test]

The samples obtained were preserved for a period of 20 days in a thermostat kept at 80° C. and at 15% in relative humidity. Before and after the preservation, the difference in the blue-colored light relection density, (incremental density) in the white-color area of each specimen was measured. The results are presented in Table 4.

TABLE 4

| Sample No. | Coupler | Anti-fading agent* | Fading ratio (%) | Coloring density | Fog | Stain |
|---|---|---|---|---|---|---|
| 25 (Reference) | MC-1 | None | 65 | — | 0.04 | 0.15 |
| 26 (Reference) | " | Anti-fading agent for reference | 62 | +0.000 | 0.04 | 0.16 |
| 27 (Reference) | " | Metallic complex for reference | 39 | +0.026 | 0.15 | 0.17 |
| 28 (This invention) | " | Metallic complex-5 | 20 | +0.005 | 0.04 | 0.15 |
| 29 (This invention) | " | Metallic complex-15 | 21 | +0.004 | 0.04 | 0.15 |
| 30 (This invention) | MC-3 | Metallic complex-15 | 21 | +0.004 | 0.04 | 0.15 |
| 31 (Reference) | 5 | None | 95 | — | 0.04 | 0.15 |
| 32 (Reference) | 5 | Anti-fading agent for reference | 89 | +0.000 | 0.04 | 0.05 |
| 33 (Reference) | 5 | Metallic complex for reference | 74 | +0.027 | 0.16 | 0.09 |
| 34 (This invention) | 5 | Metallic complex-15 | 35 | +0.004 | 0.04 | 0.06 |
| 35 (This invention) | 5 | Metallic complex-4 | 39 | +0.004 | 0.04 | 0.05 |
| 36 (This invention) | 5 | Metallic complex-5 | 35 | +0.004 | 0.04 | 0.05 |
| 37 (This invention) | 7 | Metallic complex-15 | 36 | +0.005 | 0.04 | 0.06 |
| 38 (This invention) | 41 | Metallic complex-15 | 27 | +0.004 | 0.04 | 0.05 |
| 39 (This invention) | 44 | Metallic complex-15 | 25 | +0.004 | 0.04 | 0.05 |
| 40 (This invention) | 48 | Metallic complex-15 | 23 | +0.004 | 0.04 | 0.05 |

*The anti-fading agent was added in the ratio of 0.5 mol per mol of coupler. Anti-fading agent for reference: 2.5-di-tert-octyl-hydroquinone.

Metallic complex:

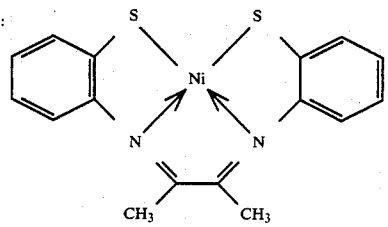

Next, Sample 26 through 40, which were identical to sample 25 except for the fact that the magenta coupler and the metallic complex (which was coated in the ratio of 0.5 mol per mol coupler were added, in the combinations shown in Table 4, to the third layer of Sample 25 mentioned above, were prepared.

The metallic complex, moreover, was added to the solvent, togehter with the coupler.

The sample thus prepared were given the same exposure and treatment as in the case of Example 3.

With respect to the individual samples obtained after the treatment, measurements were made to determine their light-resistance and coloring density in the same way as in Examples 2 and 3. Also, the fogging of the silver halide emulsion and the yellowish coloration due to heat were measured. For the fog value, the green light reflection density in the white-color area of each sample was measured, and the difference of the value from the reflection density of the support was taken as the fog value.

As it is clearly seen with reference to Table 4, those samples in which the metallic complex relevant to the present invention was used achieved a considerable light-resistance-improving effect and also could produce favorable colored pictures merely with a little of any of the coloration by the metallic complex, the fogging in the silver halide emulsion, and staining.

Furthermore, Sample 31 through 40, in which the magenta coupler expressed by the general formula [I] is used, had a less increase of yellow stain and is more suitable.

Example 5

Sample 41 through 54, which were identical with sample 38 in Example 4 except for the changes as shown in Table 5 in the metallic complex and organic solvent added to the magenta-containing layer and, in addition to this, the new addition of an anti-oxidant, were produced. These individual samples were treated in the same way as in Example 4, and measurements were made of them to determine their light-resistance, coloring density, fogging, and yellowish staining.

TABLE 5

| Sample No. | Metallic complex | Anti-oxidant | Organic solvent | Fading ratio (%) | Coloring density | Fog | Stain |
|---|---|---|---|---|---|---|---|
| 41 (Reference) | None | None | Dioctyl phthalate | 89 | — | 0.04 | 0.05 |
| 42 (Reference) | Metallic complex for reference | None | Dioctyl phthalate | 42 | +0.015 | 0.16 | 0.10 |
| 43 (This invention) | Metallic complex-4 | None | Dioctyl phthalate | 32 | +0.005 | 0.04 | 0.06 |
| 44 (This invention) | Metallic complex-5 | None | Dioctyl phthalate | 29 | +0.005 | 0.05 | 0.05 |
| 45 (This invention) | Metallic complex-14 | None | Dioctyl phthalate | 27 | +0.005 | 0.04 | 0.05 |
| 46 (This invention) | Metallic complex-15 | None | Dioctyl phthalate | 28 | +0.005 | 0.04 | 0.05 |

TABLE 5-continued

| Sample No. | Metallic complex | Anti-oxidant | Organic solvent | Fading ratio (%) | Coloring density | Fog | Stain |
|---|---|---|---|---|---|---|---|
| 47 (This invention) | Metallic complex-15 | None | Dinonyl phthalate | 27 | +0.005 | 0.04 | 0.05 |
| 48 (This invention) | Metallic complex-15 | None | Trinonyl phosphate | 29 | +0.005 | 0.04 | 0.05 |
| 49 (This invention) | Metallic complex-15 | A-8 | Dioctyl phthalate | 18 | +0.004 | 0.04 | 0.05 |
| 50 (This invention) | Metallic complex-15 | A-13 | Dioctyl phthalate | 16 | +0.004 | 0.04 | 0.05 |
| 51 (This invention) | Metallic complex-15 | J-1 | Dioctyl phthalate | 13 | +0.004 | 0.03 | 0.06 |
| 52 (This invention) | Metallic complex-15 | B-35 | Dioctyl phthalate | 13 | +0.005 | 0.04 | 0.05 |
| 53 (This invention) | Metallic complex-15 | None | Diethyl lauric acid amide | 35 | +0.005 | 0.04 | 0.05 |
| 54 (This invention) | Metallic complex-15 | None | Dimethyl phthalate | 34 | +0.005 | 0.04 | 0.05 |

The metallic complex and the anti-oxidant were added in the ratio of 0.5 mol each to one mol of the coupler.

As it is clearly seen in Table 5, Samples 43 through 48, in which the metallic salt relevant to the present invention is employed, have good resistance to light and produce favourable pictures with very little of any of coloring, fogging, or staining.

Furthermore, with Samples 49 through 52, in which an antioxidant is used in combination with the metallic complex of the present invention, the light-resistance property is improved synergistically, and it is found more preferable to use an anti-oxidant together (with the metallic complex).

Furhtermore, the results obtained in respect of Samples 46 through 48, 53 and 54 reveal that a high light-resistance-improving effect is achieved specially by the use of an organic solvent with a low dielectric constant.

Example 6

A multilayered color photosensitive element [I] was prepared by coating the layers mentioned below one after another in regular order on a support made of transparent polyethylene phthalate film with a thickness of 150 μm:

(1) An image-receiving layer with a dried film thickness of 2.5~3.0 μm and having a copolymer of styrene and N,N,N-trihexyl ammonium chloride (22 mg/100 cm$^2$) in the ratio of 1:1 and gelatin (22 mg/100 cm$^2$).

(2) a light-reflecting layer with a dried film thickness of 7~8 μm and having titanium dioxide (220 mg/100 cm$^2$) and gelatin (22 mg/100 cm$^2$), (3) a nontransparent layer 4 μm in dried film thickness and having carbon black (28 mg/100 cm$^2$) and gelatin (18 mg/100 cm$^2$), (4) a cyan coloring matter image-forming substance layer with a dried film thickness of 2.2 μm and containing a DRR compound (A) (8.63 mg/100 cm$^2$), DRR compound (B) (2.38 mg/100 cm$^2$), N,N-diethyllauroylamide (11 mg/100 cm$^2$) and gelatin (25.0 mg/100 cm$^2$), (5) a red-sensitive silver halide emulsion layer with a dried film thickness of approximately 1.5 μm and having red-sensitive internal latent image type direct positive silver bromide emulsion (14.3 mg/100 cm$^2$ as converted into silver), potassium 2-octadecylhydroquinone-5-sulfonate (0.9 mg/100 cm$^2$), formyl-4'-methylphenylhydrazide (0.13 mg/100 cm$^2$) and gelatin (16.5 mg/100 cm$^2$), (6) an intermediate layer with a dried film thickness of approximately 1.2 μm and having potassium 2-octadecylhydroquinone-5-sulfonate (6.0 mg/100 cm$^2$), and gelatin (12.0 mg/100 cm$^2$), (7) a magenta coloring matter image forming substance layer with a dried film thickness of 2.2 μm and having a DRR compound (C) (6.2 mg/100 cm$^2$), a DRR compound (D) (4.14 mg/100 cm$^2$), N,N-diethyl-lauroylamide (11 mg/100 cm$^2$), and gelatin (25.0 mg/100 cm$^2$), (8) a green-sensitive silver halide emulsion layer with a dried film thickness of approximately 1.5 μm and having green-sensitive internal latent image type direct positive silver bromide emulsion (14.0 mg/100 cm$^2$ as converted into silver), potassium 2-octadecylhydroquinone-5-sulfonate (1.0 mg/100 cm$^2$), formyl-4'-methylphenylhydrazide (0.13 mg/100 cm$^2$), and gelatin (16.5 mg/100 cm$^2$), (9) an intermediate layer with a dried film thickness of approximately 1.0 μm and having potassium 2-octadecylhydroquinone-5-sulfonate (6.0 mg/100 cm$^2$), and gelatin (12.0 mg/100 cm$^2$),

(10) a yellow coloring matter picture forming substance layer with a dried film thickness of 2.3 μm and having a DRR compound (E) (8.3 mg/100 cm$^2$), a DRR compound (F) (4.9 mg/100 cm$^2$), N,N-diethyl-lauroylamide (1.32 mg/100 cm$^2$), and gelatin (23.6 1 mg/100 cm$^2$),

(11) a blue-sensitive silver halide emulsion layer with a dried film thickness of approximately 1.5 μm and having blue-sensitive internal latent image type direct positive silver bromide emulsion (14.0 mg/100 cm$^2$), potassium 2-octadecylhydroquinone-5-sulfonate (1.0 mg/100 cm$^2$), formyl-4'-methylphenylhydrazide (0.13 mg/100 cm), and gelatin (16.5 mg/100 cm$^2$),

(12) a protective layer with a dried film thickness of 0.7 μm and having mucochloric acid (2.0 mg/100 cm$^2$) and gelatin (10.0 mg/100 cm$^2$).

Furthermore, Sample [II], which has a similar construction as that of the multi-layered color photosensitive element [I] and is identical with the element [I] except for containing the metallic complex 5 (5 mg/100 cm$^2$), which was cited as an example, in the picture-receiving layer, has been produced. Moreover, Sample [III], which is the same as the photosensitive element [I] except for containing the metallic complex 1 for reference (5 mg/100 cm$^2$) in the picture-receiving layer, has been produced.

DRR Compounds Used (A)
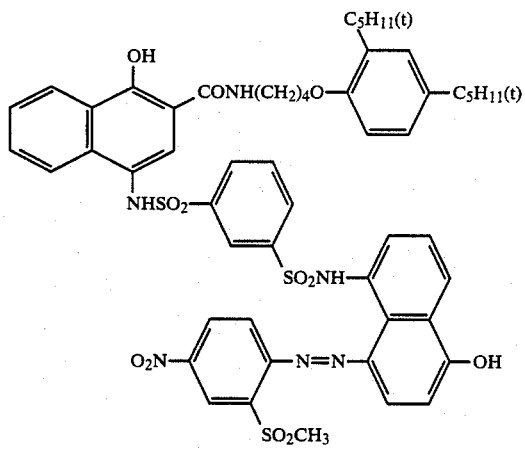
(B)
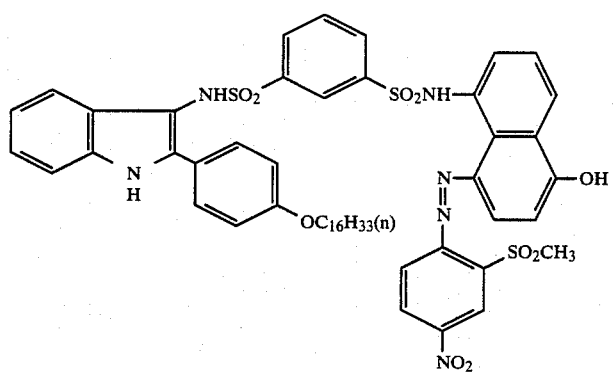
(C)
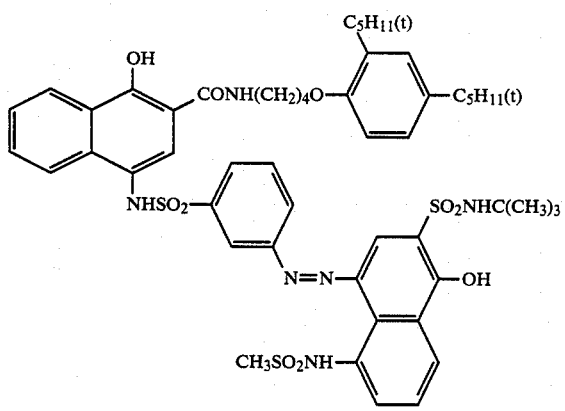
(D)
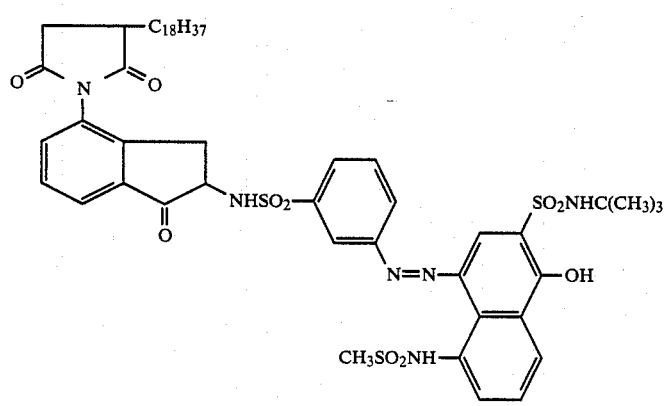

-continued

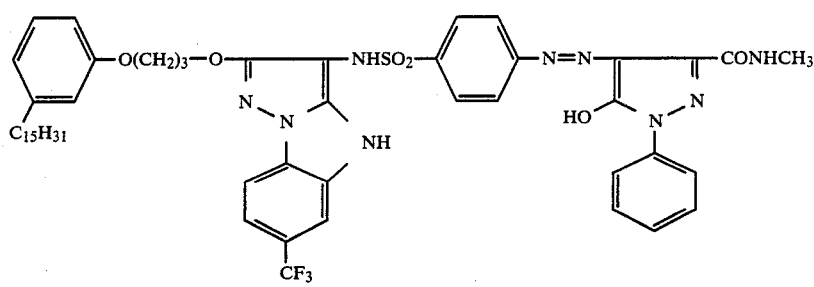
(E)

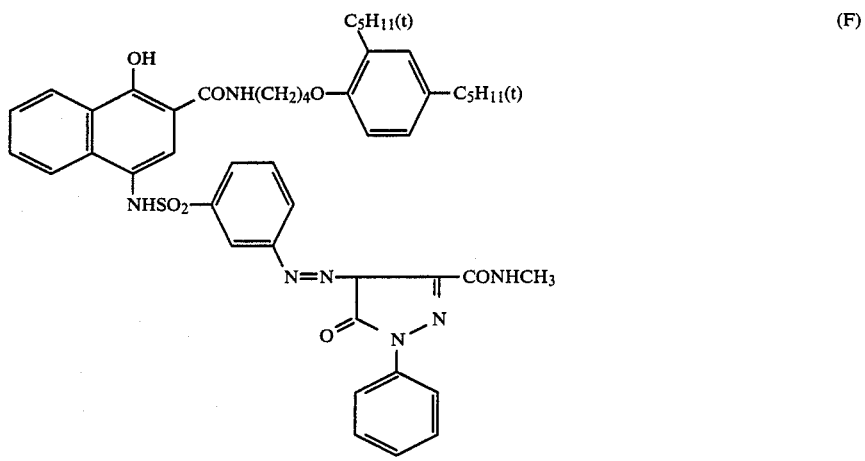
(F)

The prescribed exposure was given through the optical wedge, and thereafter the processing sheet described in the following placed for overlapping:

Processing sheet

The layers mentioned below were coated in regular order on the support made of transparent polyethylene phthalate film with a thickness of 100 μm, preparing the same for its use as a processing sheet:
(1) A neutralizing layer with a dried film thickness of 22.0 μm and having a copolymer of acrylic acid and ethyl acrylate (75/25 in weight %) (220 mg/100 cm²), and
(2) a timing layer with a dried film thickness of 5.0 μm and having cellulose diacetate (acetic acid ratio: 40%) (500 mg/100 cm²).

Furthermore, pods containing processing components with the content capacity of 1.0 ml were stuck between each multilayered color photosensitive element and the processing sheet, and the film unit was thereby produced.

The processing components were as described in the following:

| | |
|---|---|
| Potassium hydroxide | 56.0 g |
| Sodium sulfite | 2.0 g |
| 4-hydroxymethyl-4-methyl-1-phenyl-3-pyrazolydon | 8.0 g |
| 5-methylbenzothoriazole | 2.8 g |
| Carbon black | 150 g |
| Carboxymethyl cellulose sodium salt | 50.0 g |
| Benzyl alcohol | 1.5 ml |
| Total with addition of distilled water | 1.000 ml |

The pods were caused to be ruptured, the content substance being spread in the space between the above-mentioned photosensitive element and the covering sheet, by having the above-mentioned film unit pass through a pair of rollers positioned side by side with a clearance of approximately 340 μm in such a way as to exert pressure with them. A image in coloring matter could be obtained after approximately 8 to 10 minutes.

The green light reflecting density of the obtained image in coloring matter was measured, and the same light-resistance test as in Example 1 was conducted. The results are presented in Table 6.

TABLE 6

| Sample | Fading ratio (%) under light | Coloring degree |
|---|---|---|
| [I] (Reference) | 97 | — |
| [II] (This invention) | 49 | +0.003 |
| [III] (Reference) | 71 | +0.022 |

As is evidently seen in the Table given above, the metallic complex of the present invention has achieved a significant effect in securing color-fastness against light, even in the case of image with dispersed and transferred coloring matter, and favorable image merely with a little coloration could be obtained.

What is claimed is:

1. A method for increasing fastness of an organic coloring matter, making coexist the organic coloring matter having the absorption maximum within the wavelength region from 400 nm to 700 nm with a compound represented by the following general formula in a medium:

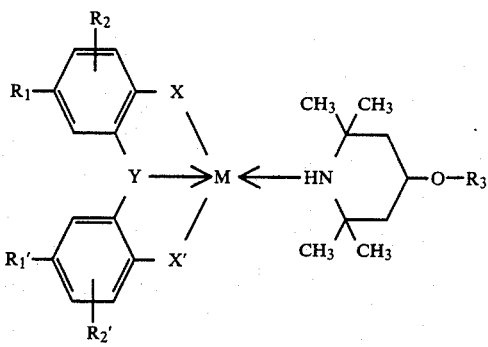

wherein $R_1$ and $R_1'$ are independently selected from a hydrogen atom, an alkyl group, a cycloalkyl group, a halogen atom, an alkoxy group, an aryloxy group, $-CO-O-R_4$,

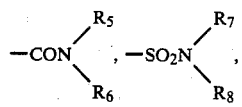

$-NHCOR_9$ and $-NHSO_2R_{13}$, $R_4$ is selected from an alkyl group and a cycloalkyl group, $R_5$ and $R_6$ are independently selected from a hydrogen atom, an alkyl group, an aryl group and a cycloalkyl group, and $R_5$ and $R_6$ may be bonded to form a five to seven membered ring, $R_7$ and $R_8$ are the same as $R_5$ and $R_6$, $R_9$ is selected from an alkyl group, an aryl group $-OR_{10}$ and

$R_{10}$ is selected from an alkyl group and a cycloalkyl group, $R_{11}$ and $R_{12}$ are the same as $R_5$ and $R_6$, $R_{13}$ is selected from an alkyl group, an aryl group and

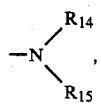

$R_{14}$ and $R_{15}$ are the same as $R_5$ and $R_6$, $R_2$ and $R_2'$ are independently selected from a hydrogen atom, a halogen atom, an alkyl group, an alkoxy group, an alkoxycarbonyl group, an alkenyl group and a cycloalkyl group, and $R_1$ and $R_2$, or $R_1'$ and $R_2'$ may be bonded to form a condensed benzene ring, respectively, M is a metal atom, X and X' is independently selected from an oxygen atom and a sulfur atom, Y is selected from an oxygen atom, a sulfur atom, $-SO$ and $-SO_2$, and $R_3$ is selected from a hydrogen atom, an alkyl group, an aryl group, a cycloalkyl group, $-CO-R_{16}$,

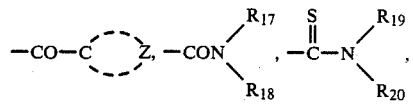

$-SO-R_{21}$ and $-SO_2R_{22}$, $R_{16}$ is selected from an alkyl group, an alkenyl group, an aryl group and a cycloalkyl group, Z is a group of atoms necessary to complete five or six membered heterocyclic ring, $R_{17}$ and $R_{18}$ are independently selected from a hydrogen atom, an alkyl group, an aryl group and a cycloalkyl group, $R_{17}$ and $R_{18}$ may be bonded to form a five to seven membered ring, $R_{19}$ and $R_{20}$ are the same as $R_{17}$ and $R_{18}$, $R_{21}$ is selected from an alkyl group and an aryl group and $R_{22}$ is the same as $R_{21}$.

2. The method of claim 1, wherein an amount of the compound represented by the general formula is from 0.01 to 1 mole per mole of said organic coloring matter.

3. The method of claim 1, wherein said medium is a layer contained in a silver halide photographic material.

4. The method of claim 1, wherein said medium is a receiving layer of a diffusion transfer photographic material.

5. The method of claim 1, wherein said compound represented by the general formula is dispersed in said medium together with a high boiling point solvent of which dielectric constant is from 1.9 to 6.0.

6. The method of claim 5, wherein said high boiling solvent is selected from the compounds represented by the general formula [a]:

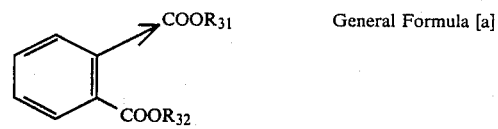

General Formula [a]

wherein $R_{31}$ and $R_{32}$ are independently selected from an alkyl group, an alkenyl group and an aryl group, and the total numbers of the carbon atoms contained in $R_{31}$ and $R_{32}$ is from 8 to 32.

7. The method of claim 5, wherein said high boiling point solvent is selected from the compounds represented by the general formula [b]:

General formula [b]

wherein $R_{33}$, $R_{34}$ and $R_{35}$ are independently selected from an alkyl group, an alkenyl group and an aryl group, and the total number of the carbon atoms contained in $R_{33}$, $R_{34}$ and $R_{35}$ is from 24 to 54.

8. The method of claim 1, wherein said organic coloring matter is a product by coupling a color forming coupler with the oxidation product of a color developing agent.

9. The method of claim 8, wherein said color forming coupler is a magenta forming coupler represented by the general formula [I]:

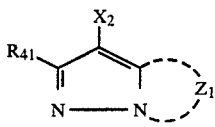

General formula [I]

wherein $Z_1$ is a group of non-metalic atoms necessary to form a nitrogen-containing heterocyclic ring which may have a substituent, $X_2$ is represents a hydrogen atom or a group which is, upon reaction with an oxidation product of a color developing agent, capable of being released from the coupler residue and $R_{41}$ represent a hydrogen atom or a substituent.

10. The method of claim 8, wherein said color forming coupler is a magenta forming coupler represented by the general formula [XIV]:

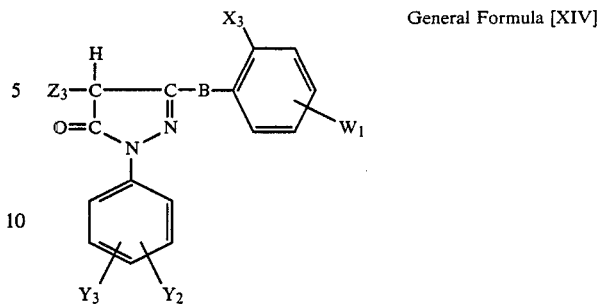

General Formula [XIV]

wherein $X_3$ is selected from a hydrogen atom, a halogen atom, an alkyl group, an aryl group, an alkoxy group, an aryloxy group, an amido group, a hydroxy group, an amino group and a nitro group, $Y_1$, $Y_2$ and $Y_3$ are independently selected from a hydrogen atom, a halogen atom, an alkyl group, an alkoxy group, a carboxy group, an alkoxycarbonyl group, a nitro group, an aryloxy group, a cyano group and an acylamino group, $W_1$ is selected from a hydrogen atom, a halogen atom and a monovalent organic group, $Z_3$ is represents an atom or a group which is, upon reaction with an oxidation product of a color developing agent, capable of being released from the coupler residue and B is selected from —NH—, —NHCO— and —NHCONH—.

* * * * *